(12) United States Patent
Costa-Mattioli et al.

(10) Patent No.: US 11,135,252 B2
(45) Date of Patent: Oct. 5, 2021

(54) PROBIOTIC THERAPIES FOR DEVELOPMENTAL DISORDERS AND OTHER NEUROLOGICAL DISORDERS

(71) Applicant: Baylor College of Medicine, Houston, TX (US)

(72) Inventors: Mauro Costa-Mattioli, Houston, TX (US); Shelly Alexandra Buffington, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 105 days.

(21) Appl. No.: 16/093,593

(22) PCT Filed: Apr. 15, 2017

(86) PCT No.: PCT/US2017/027827
§ 371 (c)(1),
(2) Date: Oct. 12, 2018

(87) PCT Pub. No.: WO2017/181158
PCT Pub. Date: Oct. 19, 2017

(65) Prior Publication Data
US 2019/0070226 A1 Mar. 7, 2019

Related U.S. Application Data

(60) Provisional application No. 62/322,946, filed on Apr. 15, 2016.

(51) Int. Cl.
| | | |
|---|---|---|
| *A61K 35/742* | (2015.01) |
| *A61K 9/02* | (2006.01) |
| *A61K 9/20* | (2006.01) |
| *A61K 35/747* | (2015.01) |
| *A23C 9/123* | (2006.01) |
| *A61K 9/00* | (2006.01) |
| *A61K 35/00* | (2006.01) |

(52) U.S. Cl.
CPC .......... *A61K 35/742* (2013.01); *A23C 9/1234* (2013.01); *A61K 9/0053* (2013.01); *A61K 9/02* (2013.01); *A61K 9/20* (2013.01); *A61K 35/747* (2013.01); *A23V 2002/00* (2013.01); *A23Y 2220/71* (2013.01); *A61K 2035/115* (2013.01)

(58) Field of Classification Search
CPC ...... A61K 35/742; A61K 35/747; A61K 9/20; A61K 9/02; A61K 9/0053; A61K 2035/115; A23C 9/1234; A23V 2002/00; A23Y 2220/71; A61P 25/28; A61P 25/20; A61P 25/00

See application file for complete search history.

(56) References Cited

U.S. PATENT DOCUMENTS

| 7,344,867 B2 | 3/2008 | Connolly |
| 2006/0105939 A1 | 5/2006 | Hollander |
| 2011/0091431 A1 | 4/2011 | Olmstead |
| 2012/0171165 A1* | 7/2012 | Buck ...................... A61P 29/00 424/93.4 |
| 2014/0187513 A1 | 7/2014 | Stahl et al. |
| 2014/0249103 A1 | 9/2014 | Buck et al. |
| 2014/0363410 A1* | 12/2014 | Bergonzelli Degonda ................. A61P 43/00 424/93.45 |
| 2017/0027996 A1 | 2/2017 | Cutcliffe et al. |

FOREIGN PATENT DOCUMENTS

| EP | 2609813 A1 | 7/2013 |
| WO | 2010/060722 A1 | 6/2010 |
| WO | 2013098033 A1 | 7/2013 |

OTHER PUBLICATIONS

Ibrahim, Y. M. et al. 2014. Maternal Gut Microbes Control Offspring Sex and Survival. J Prob Health. 2:1. (Year: 2014).*
Rivera, H. M. et al. 2015. The role of maternal obesity in the risk of neuropsychiatric disorders. Frontiers in Neuroscience. 9:194. (Year: 2015).*
BioGaia Gastrus. https://www.biogaia.com/product/biogaia-gastrus/ (Year: 2015).*
Kedar, N.P. 2003. Can we prevent Parkinson's and Alzheimer's disease?. J Postgrad Med. 49: 3. pp. 236-245 (Year: 2003).*
Rice, L. J. et al. 2015. The developmental trajectory of disruptive behavior in Down syndrome, fragile X syndrome, Prader-Willi syndrome and Williams syndrome. American Journal of Medical Genetics. 169: 2. pp. 182-187. (Year: 2015).*
Mental Illness. Mayo Clinic. Retrieved from: https://www.mayoclinic.org/diseases-conditions/mental-illness/symptoms-causes/syc-20374968 (Year: 2020).*
Autism Spectrum Disorder. Mayo Clinic. Retrieved from: https://www.mayoclinic.org/diseases-conditions/autism-spectrum-disorder/symptoms-causes/syc-20352928 (Year: 2020).*
Bipolar Disorder: Prevention. 2018. Cleveland Clinic. Retrieved from: https://my.clevelandclinic.org/health/diseases/9294-bipolar-disorder/prevention (Year: 2018).*

(Continued)

*Primary Examiner* — Ruth A Davis
(74) *Attorney, Agent, or Firm* — Norton Rose Fulbright US LLP

(57) ABSTRACT

Embodiments of the disclosure concern methods and compositions related to manipulation of the microbiome in an individual having at least one social behavior deficit. In particular embodiments, an individual has at least one social behavior deficit and was born from a mother who during pregnancy was obese, overweight, or on a high-fat diet during pregnancy or carries mutations associated with neurodevelopmental disorders. In specific embodiments, the individual having at least one social behavior deficit is provided an effective amount of *Lactobacillus reuteri* for the improvement of at least one symptom of a social behavior deficit.

8 Claims, 79 Drawing Sheets

(56) References Cited

OTHER PUBLICATIONS

Crawford, "Is it Time to Begin Prenatal/Neonatal Screening for Autism Risk?", Global J Pediatrics & Neonatal Care, vol. 1, Issue 3, 2019 (Year: 2019).*

Ibrahim et al., "Maternal Gut Microbes Control Offspring Sex and Survival", J Prob Health 2014, 2:1 (Year: 2014).*

Nadeem et al., "Multiple Risk Factors: A Challenge in the Management of Autism", Curr Pharm Des. 2020;26(7):743-754. (Year: 2020).*

Sgritta et al., "Mechanisms Underlying Microbial-Mediated Changes in Social Behavior in Mouse Models of Autism Spectrum Disorder", Neuron. Jan. 16, 2019;101(2):246-259 (Year: 2019).*

Lactobacillus reuteri MM4-1A, PTA-6475 Product Sheet, https://www.atcc.org/products/pta-6475 (Year: 2021).*

Adams et al., "Gastrointestinal flora and gastrointestinal status in children with autism-comparison to typical children and correlation with autism severity", BMC Gastroenterology, 2011, 11:22.

Galley et al., "Maternal Obesity is Associated with Alterations in the Gut Microbiome in Toddlers" PLOS ONE, Nov. 2014, vol. 9, Issue 11, e113026.

Hsiao, et al. "The microbiota modulates gut physiology and behavorial abnormalities associated with autism" Cell, Dec. 19, 2013, 155(7): pp. 1451-1463.

Konstantinidis et al., "Genomic insights that advance the species definition for prokaryotes", PNAS, Feb. 15, 2005, vol. 102, No. 7, pp. 2567-2572.

Krajmalnik-Brown et al., "Gut bacteria in children with autism spectrum disorders: challenges and promise of studying how a complex community influences a complex disease", Microbial Ecology in Health and Disease, 2015, 26:26914.

Ma et al., "High-fat maternal diet during pregnancy persistently alters the offspring microbiome in a primate model", Nat. Commun., Nov. 20, 2014, 5:3889.

Rhoads, J. Marc "Road to Discovery for Combination Probiotic BB-12 With LGG in Treating Autism Spectrum Disorder" Feb. 5, 2016, https://clinicaltrials.gov/ct2/show/NCT02674984.

Tomova, A. et al., "Gastrointestinal microbiota in children with autism in Slovakia", Physiology & Behavior, 2015, vol. 138, p. 179-187.

Yatawara et al., "The effect of oxytocin nasal spray on social interaction deficits observed in young children with autism: a randomized clinical crossover trial", Molecular Psychiatry (2016) 21, 1225-1231.

Buffington et al: "Microbial Reconstitution Reverses Maternal Diet-Induced Social and Synaptic Deficits in Offspring", CELL, vol. 165, No. 7, Jun. 16, 2016 (Jun. 16, 2016), pp. 1762-1775, Elsevier, Amsterdam, NL.

Scattoni, Maria Luisa, et al; "Unusual Repertoire of Vocalizations in the BTBR T+tf/J Mouise Model of Autism"; Plos One, Aug. 2008; vol. 3, Issue 8.

Penagarikano, Olga, et al.; "Absence of CNTNAP2 Leads to Epilepsy, Neuronal Migration Abnormalities, and Core Autism-Related Deficits"; Cell 147; Sep. 30, 2011; 235-246.

Sgritta, Martina, et al; Mechanisms Underlying Microbial-Mediated Changes in Social Behavior in Mouse Models of Autism Spectrum Disorder; Neuron 101; Jan. 16, 2019; 246-259.

McFarlane, H.G.,; Autism-like Behavioral Phenotypes in BTBR T +tf/J Mice; Genes, Brain and Behavior; 2008; 7: 152-163.

Buffington, Shelly A, et al; "Microbial Reconstitution Reverses Maternal Diet-Induced Social and Synaptic Deficits in Offspring"; Cell 165; Jun. 16, 2016; 1762-1775.

* cited by examiner

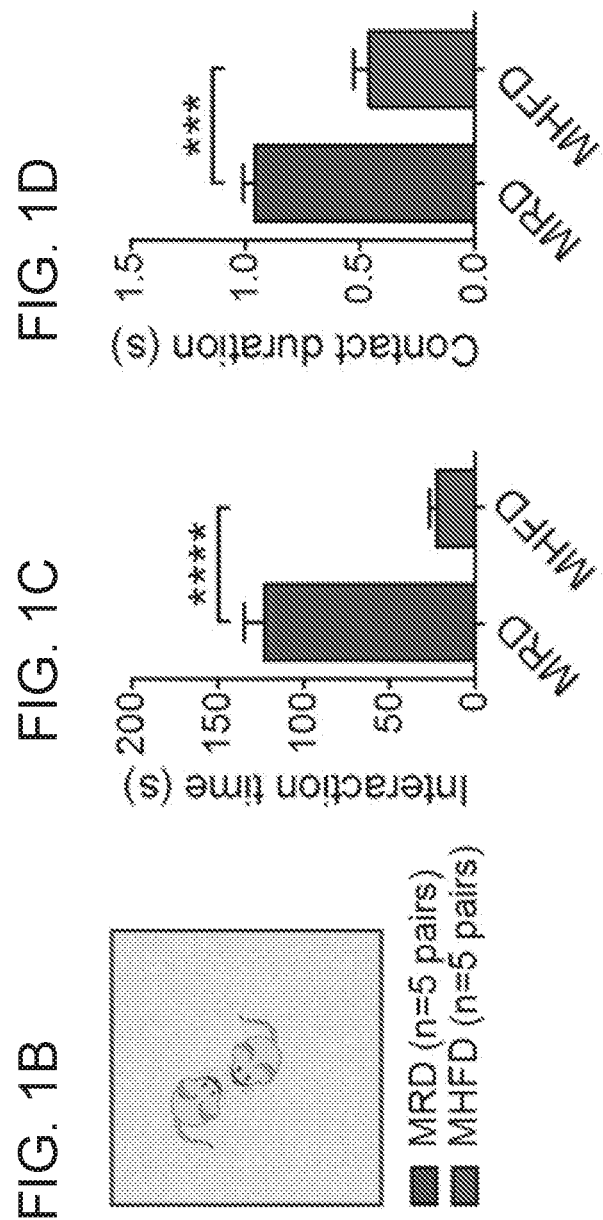

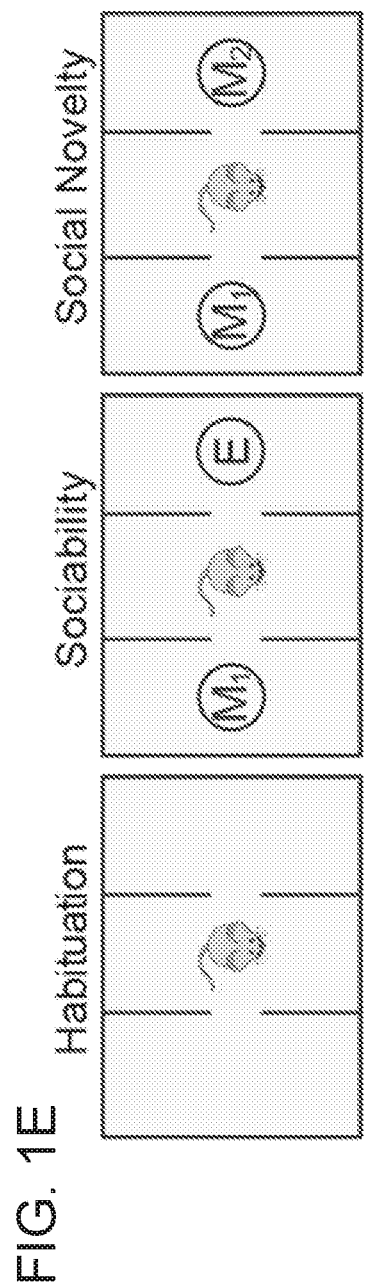

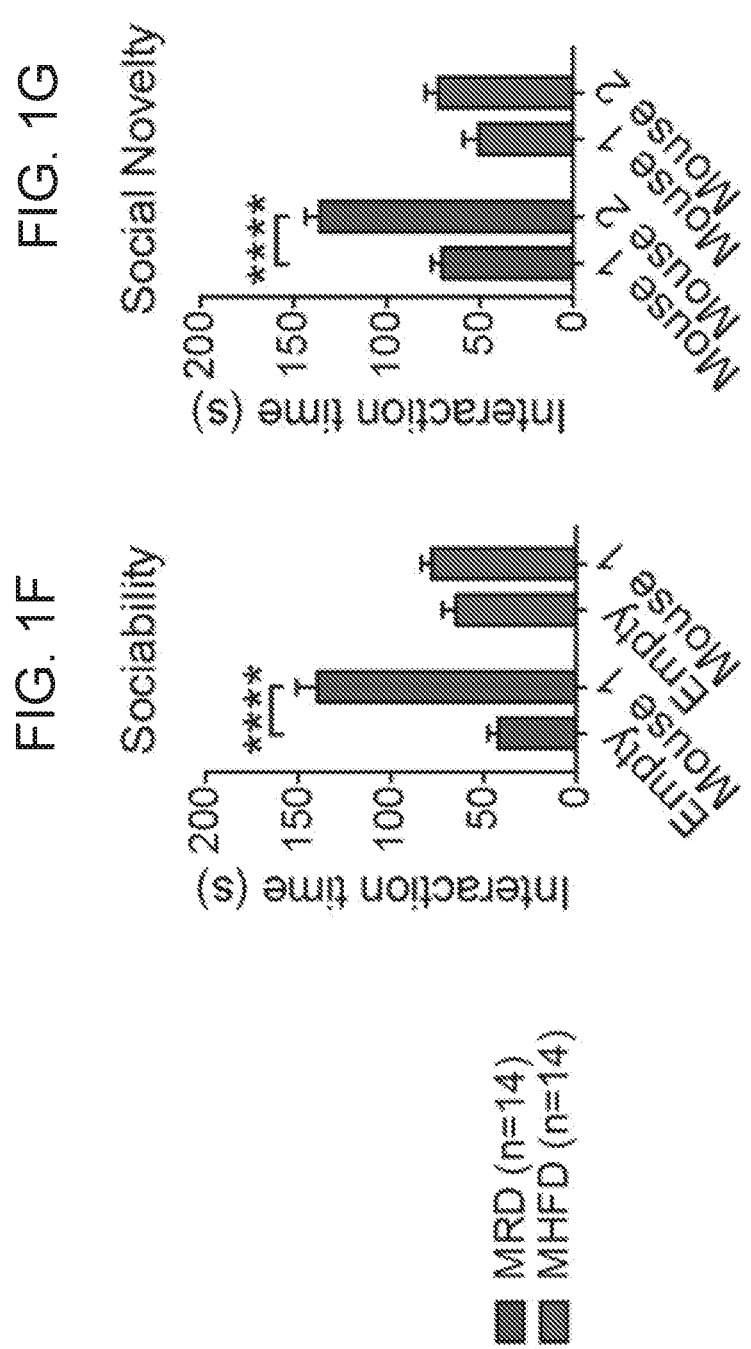

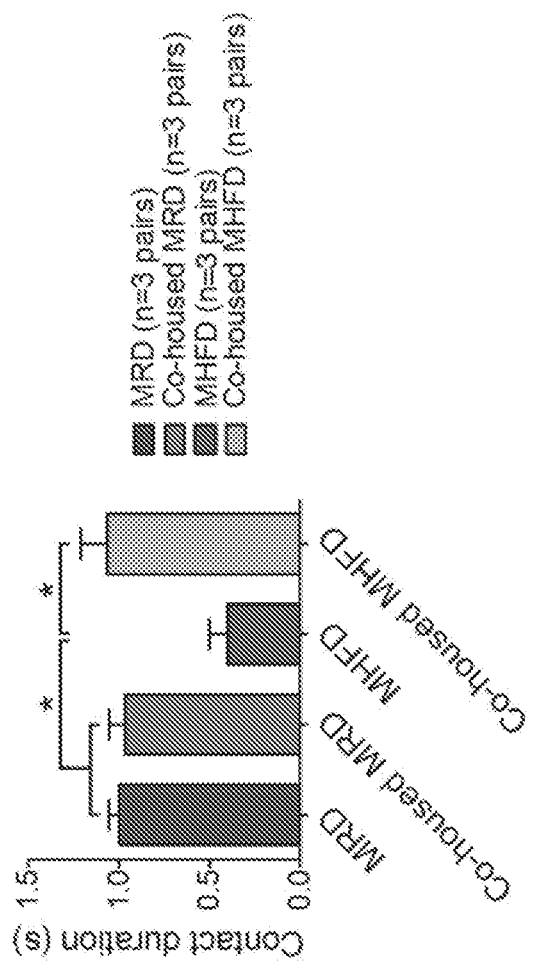
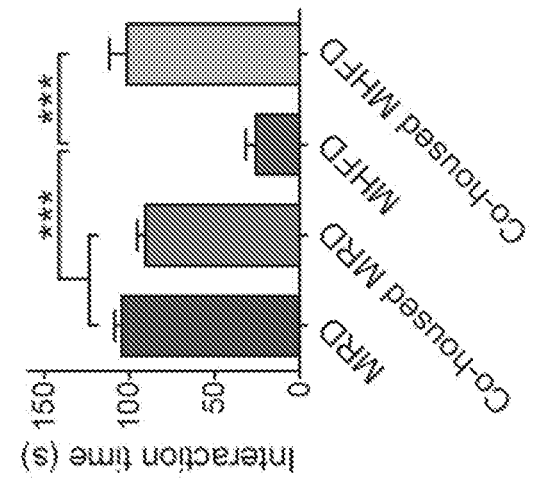
FIG. 2D
FIG. 2C

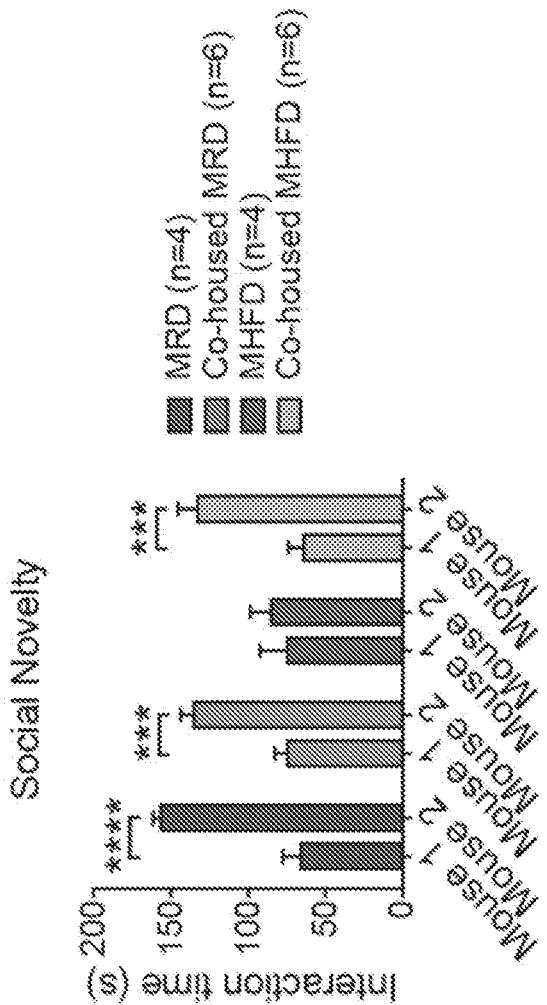
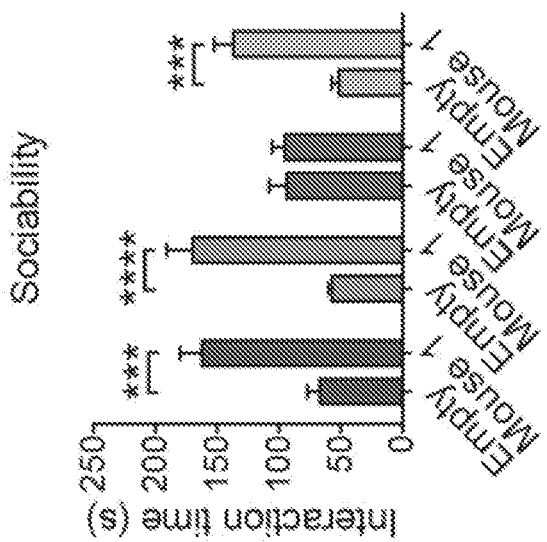
FIG. 2E Sociability
FIG. 2F Social Novelty

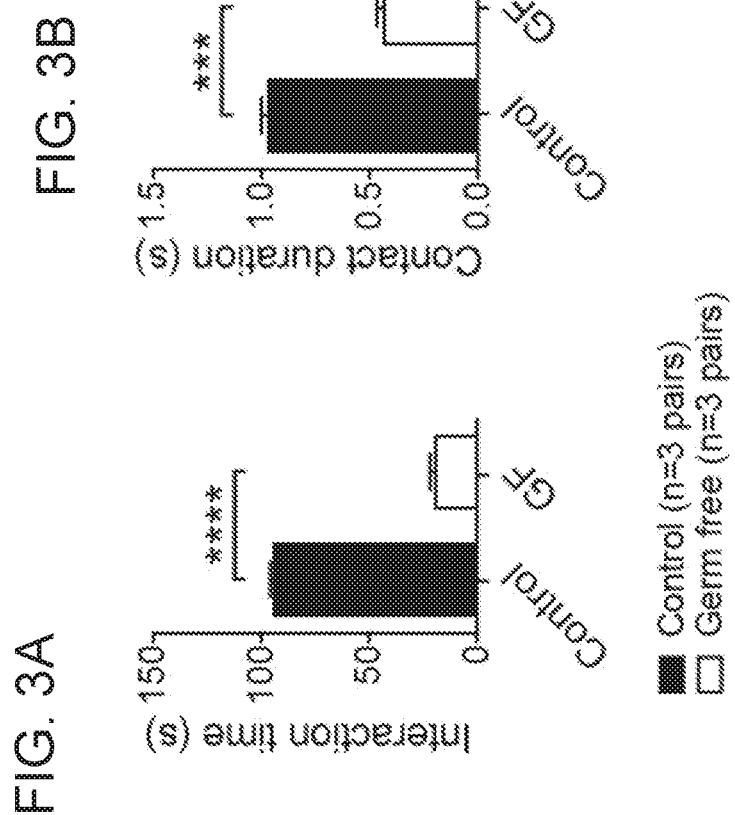

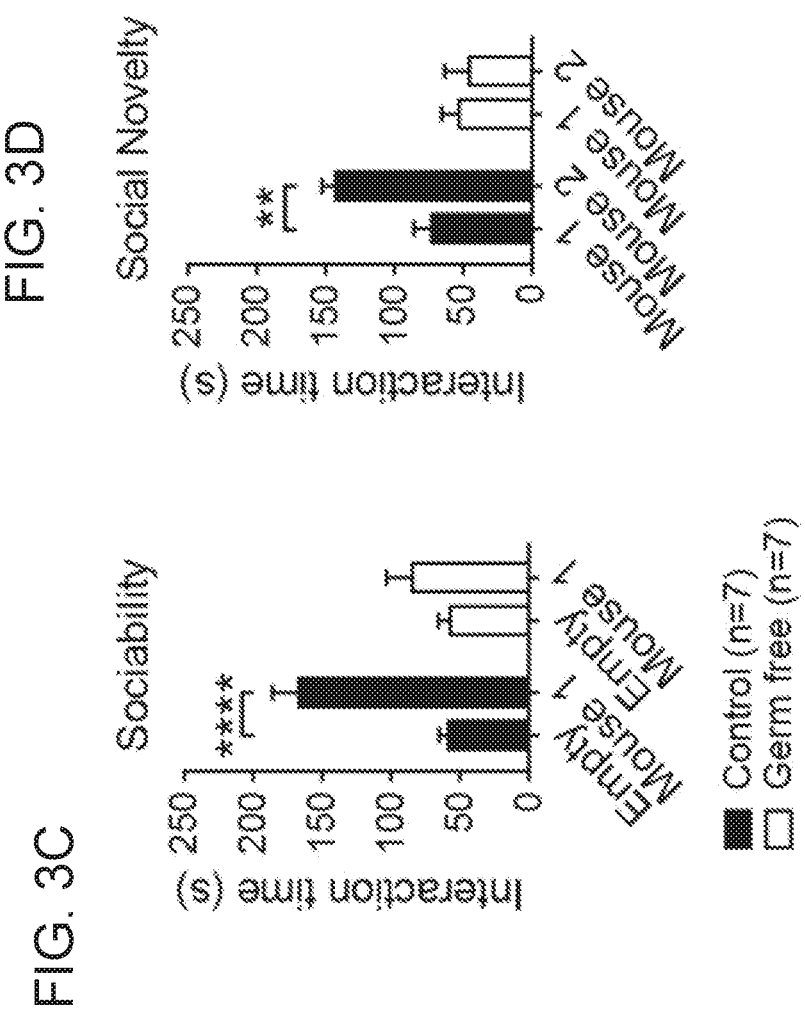

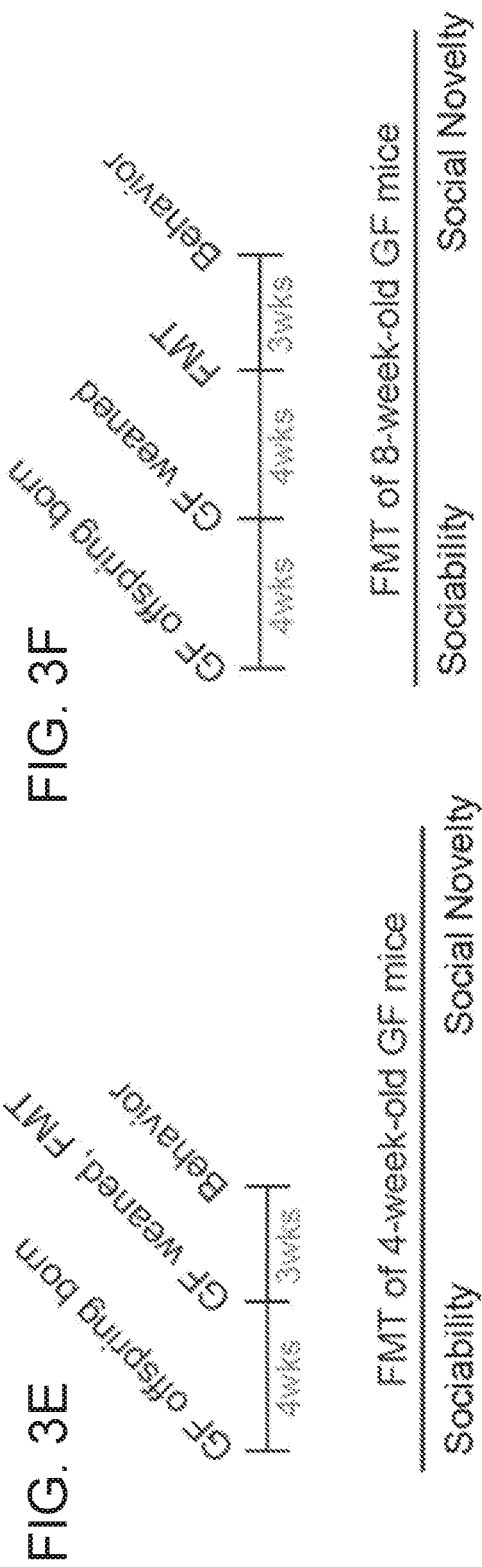

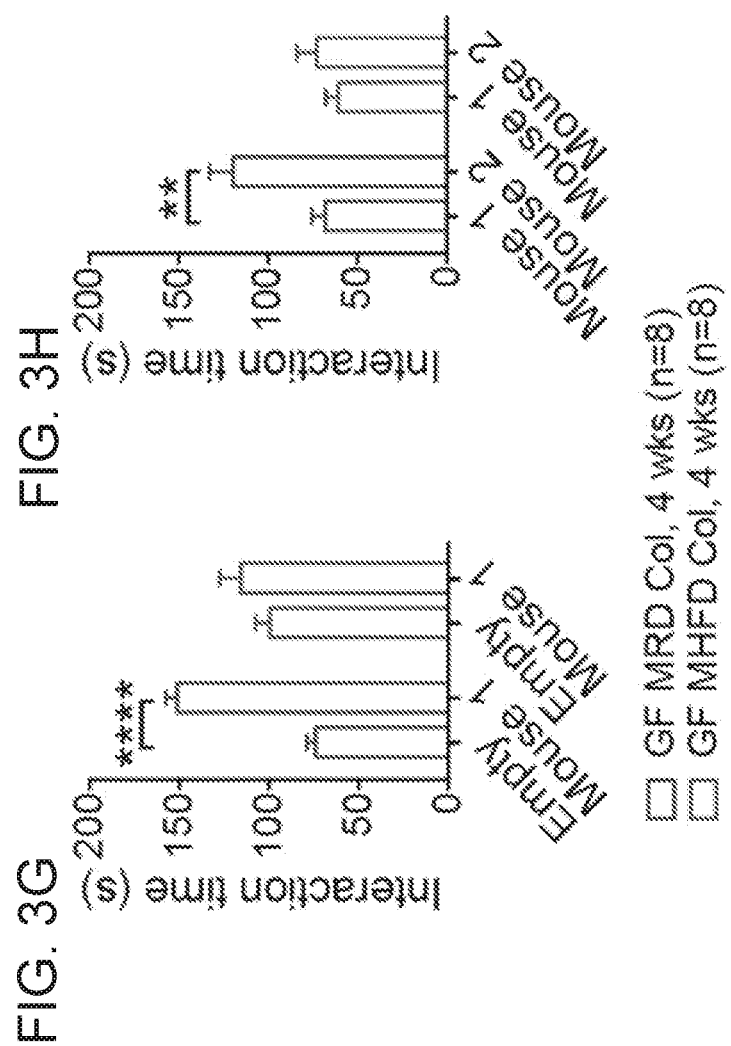

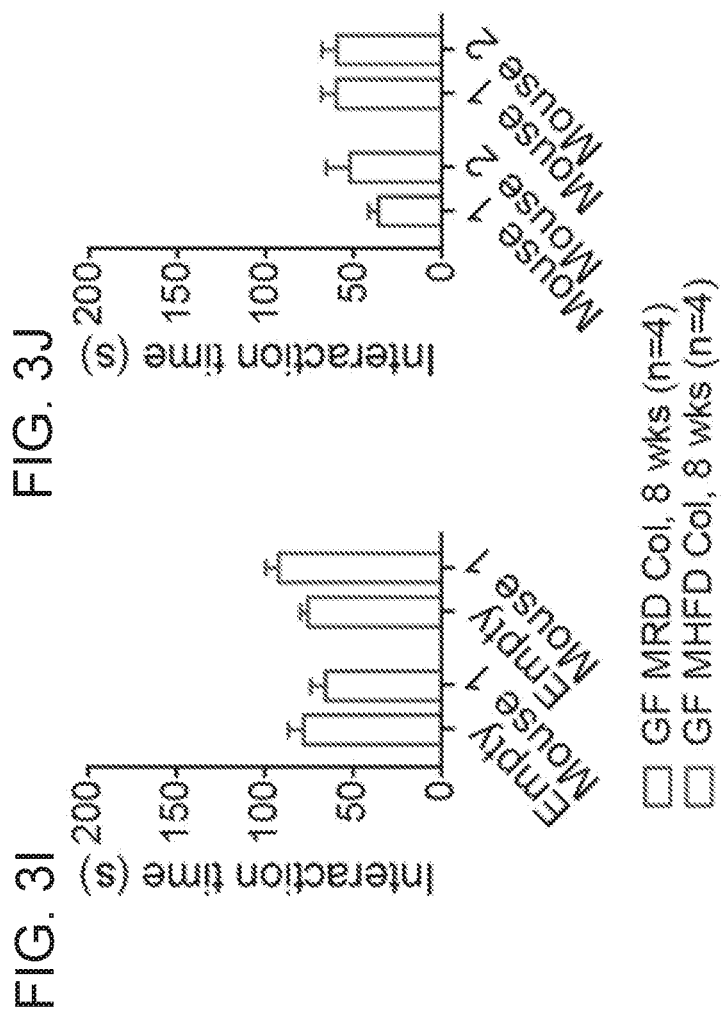

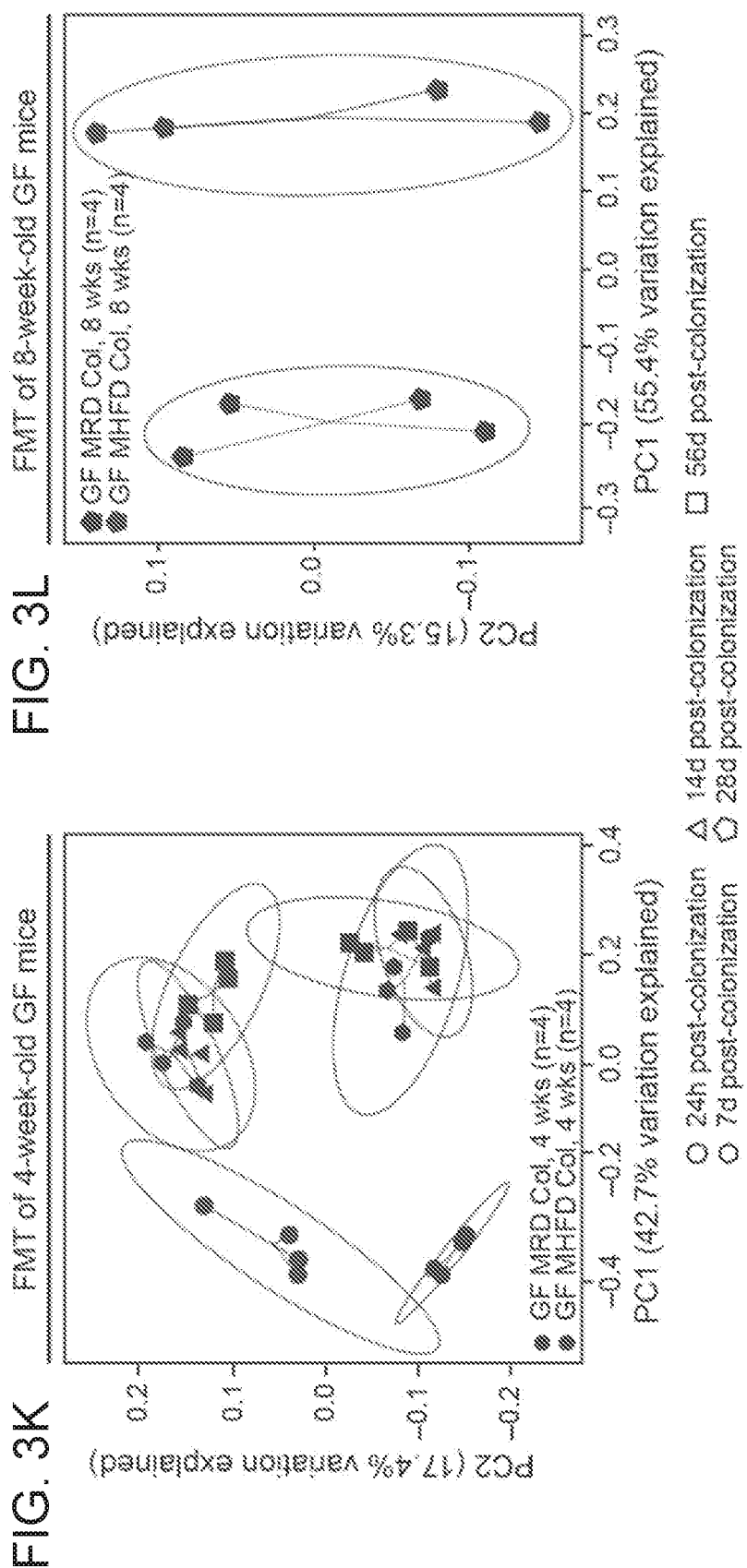

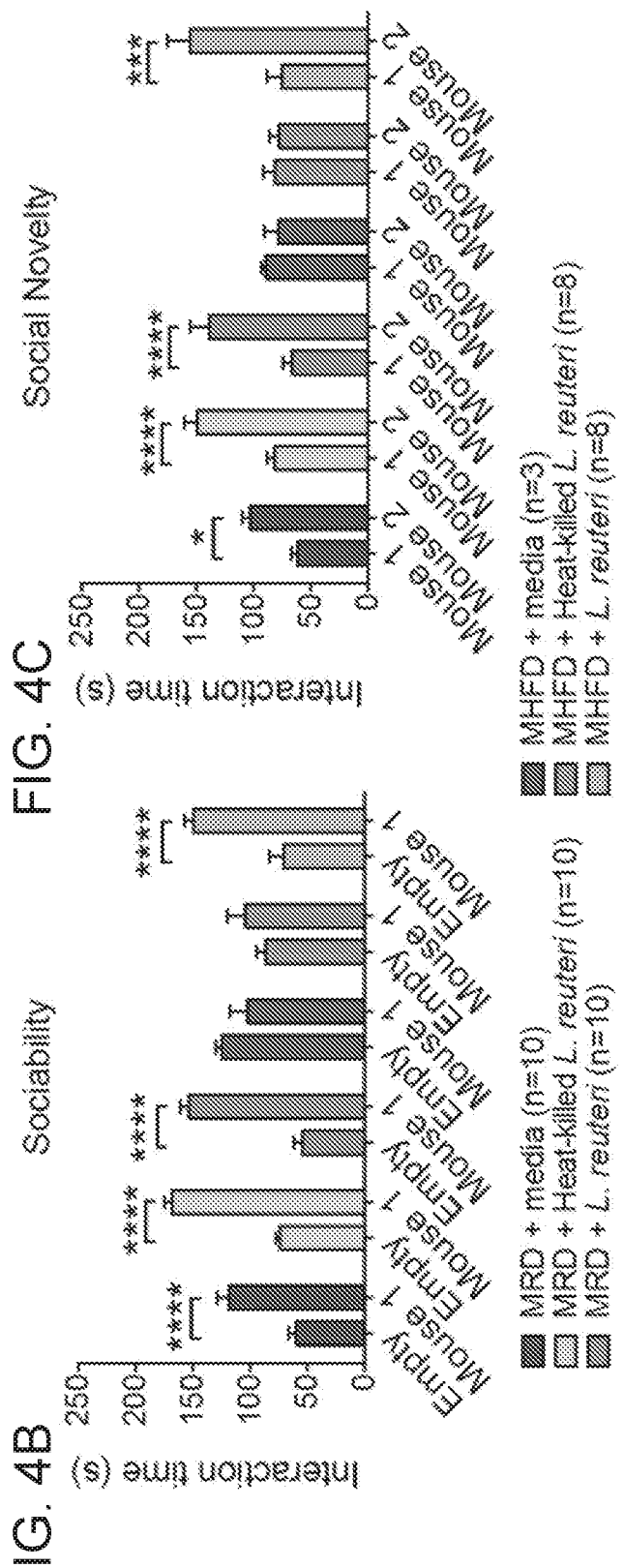

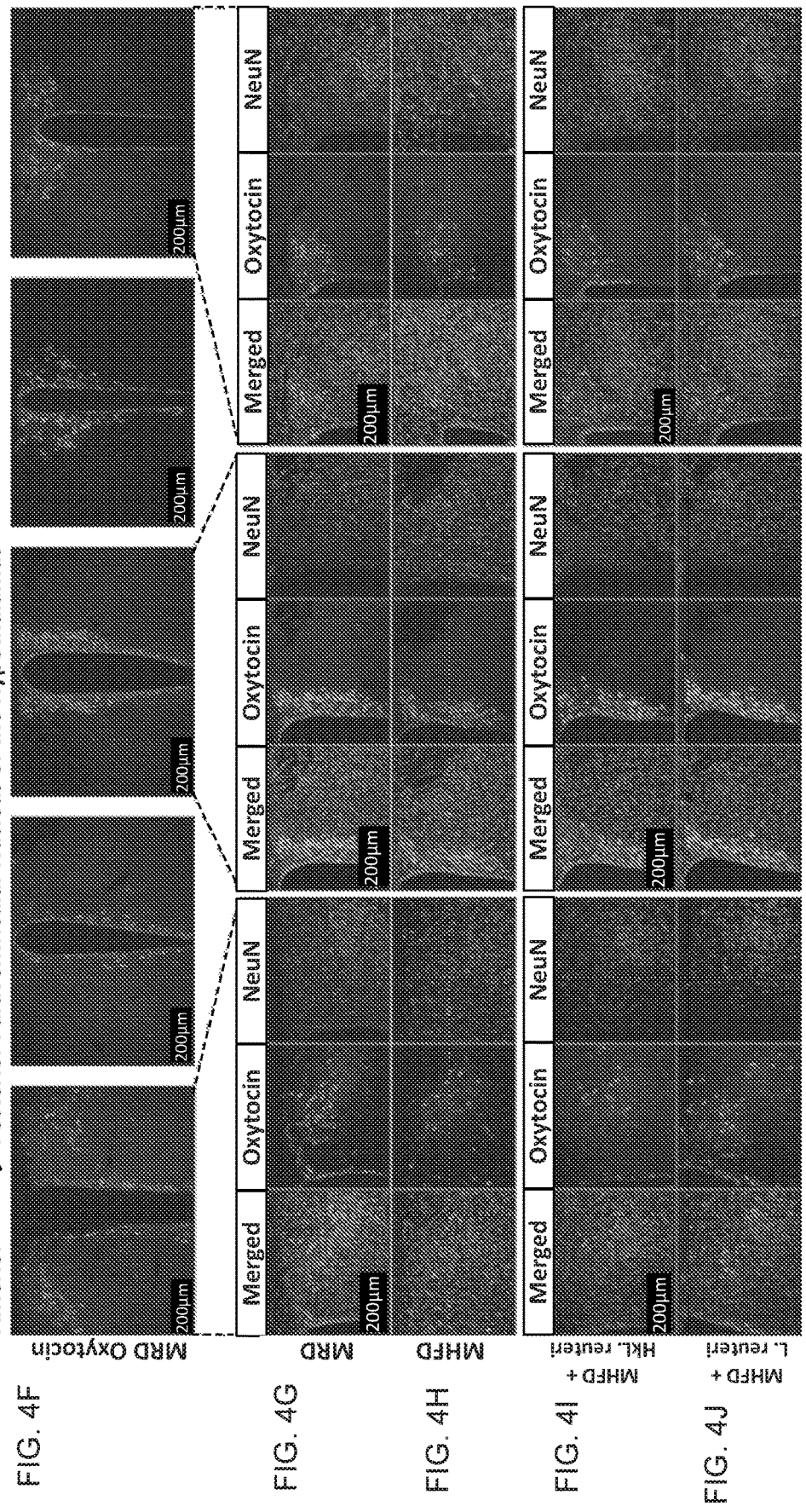

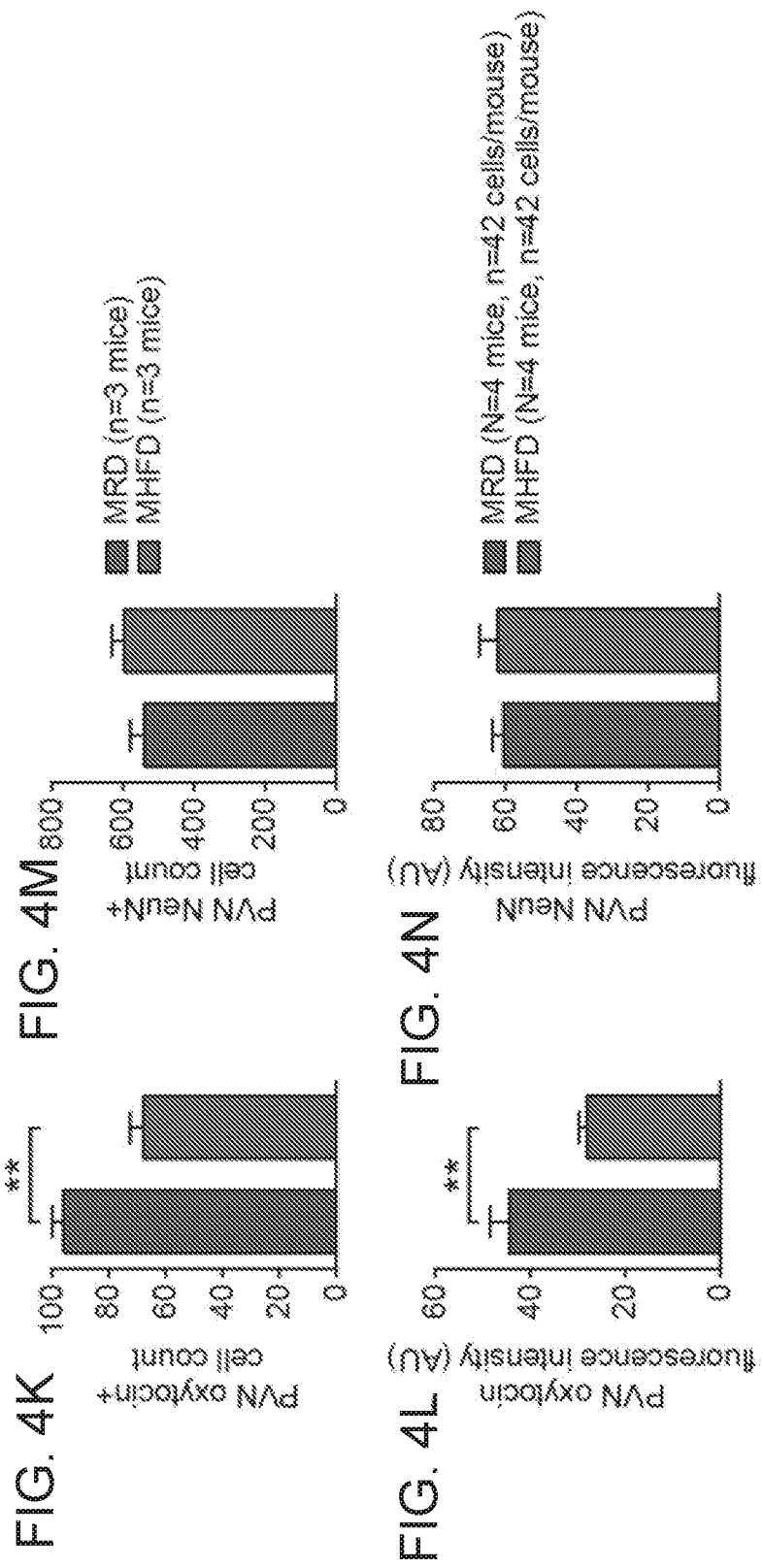

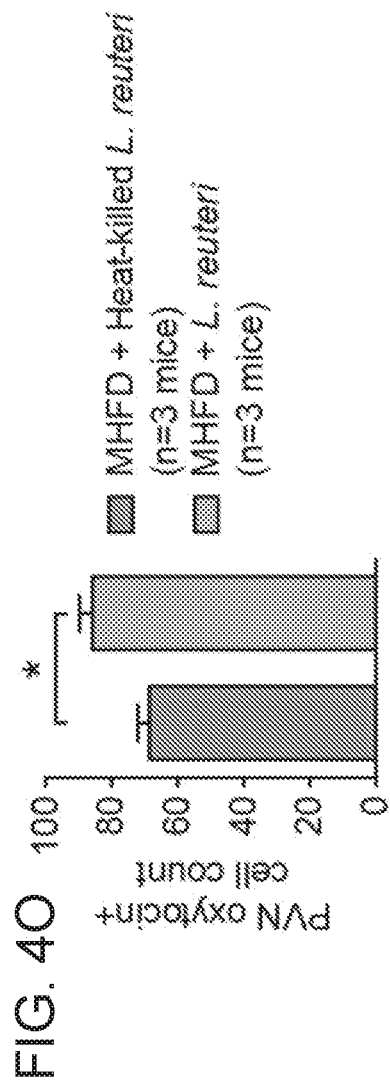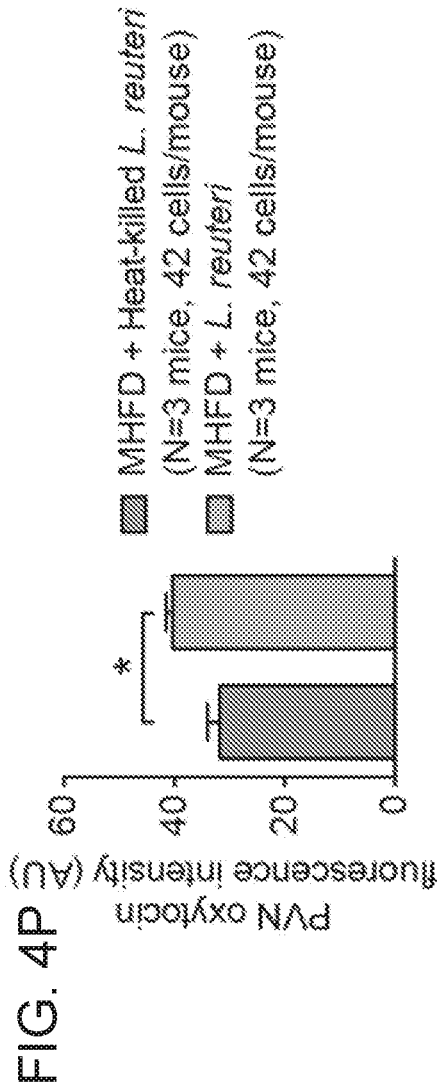

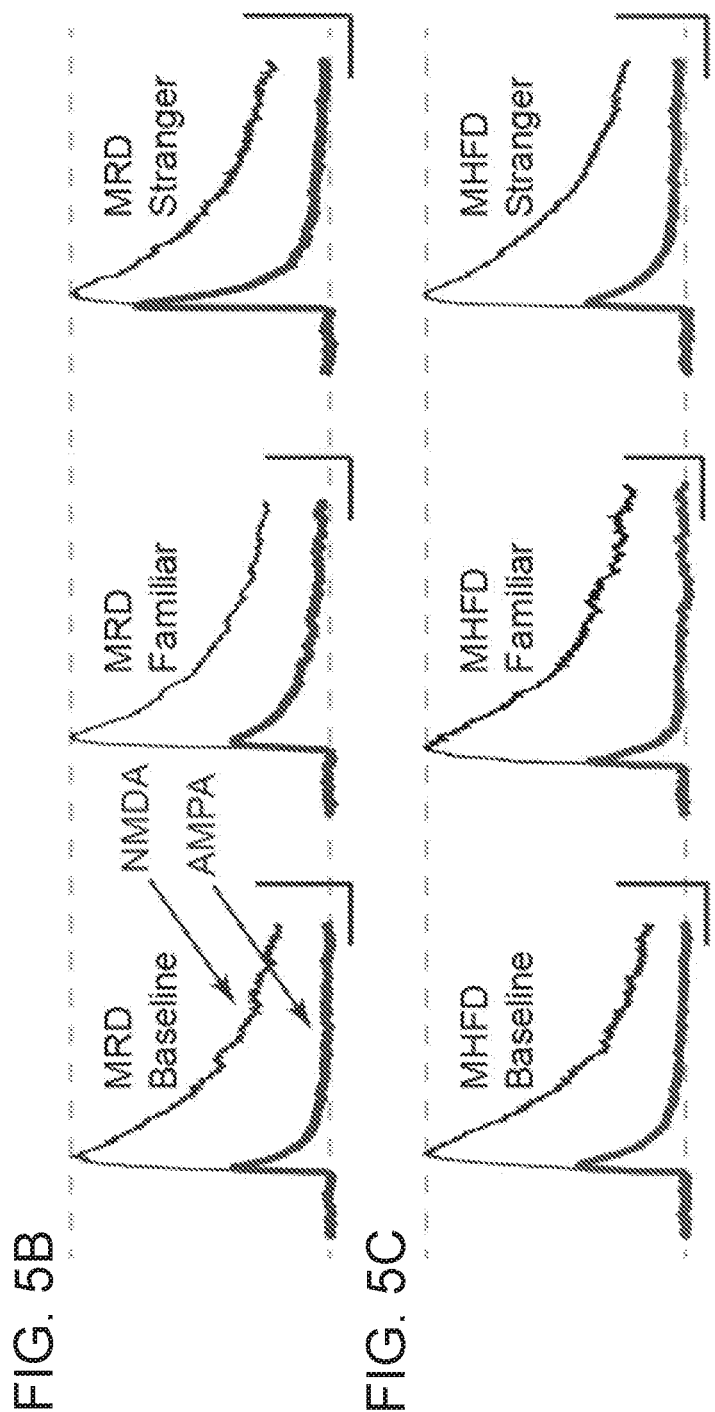

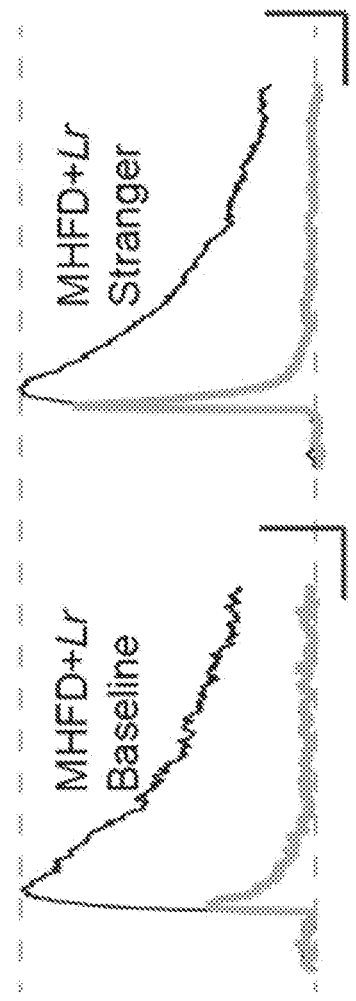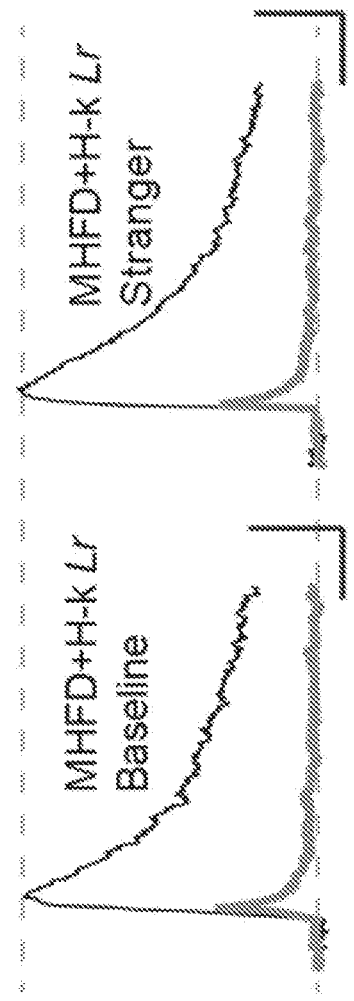
FIG. 5H
FIG. 5I

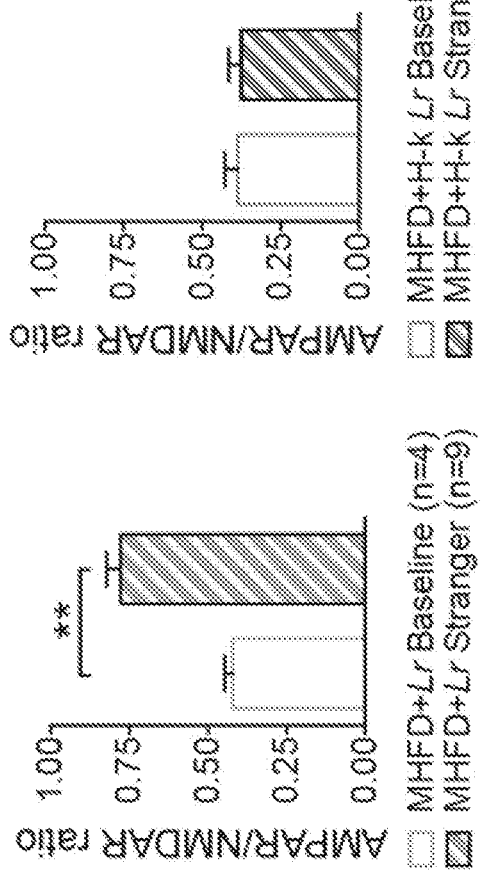
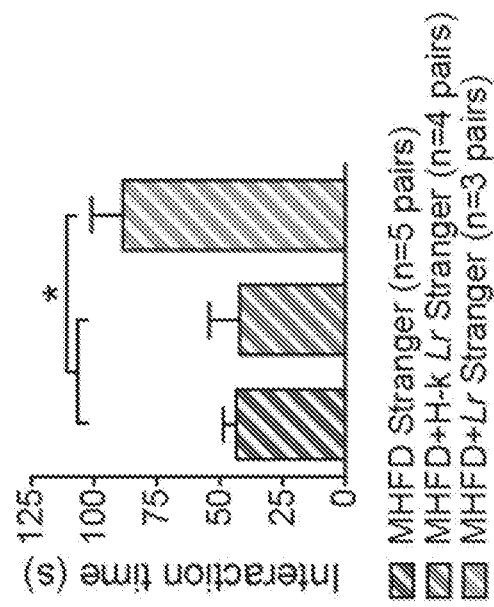

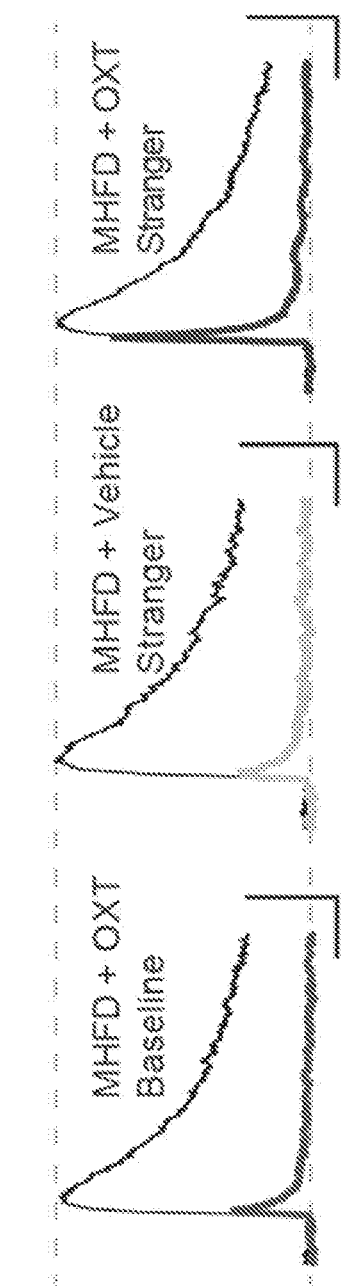

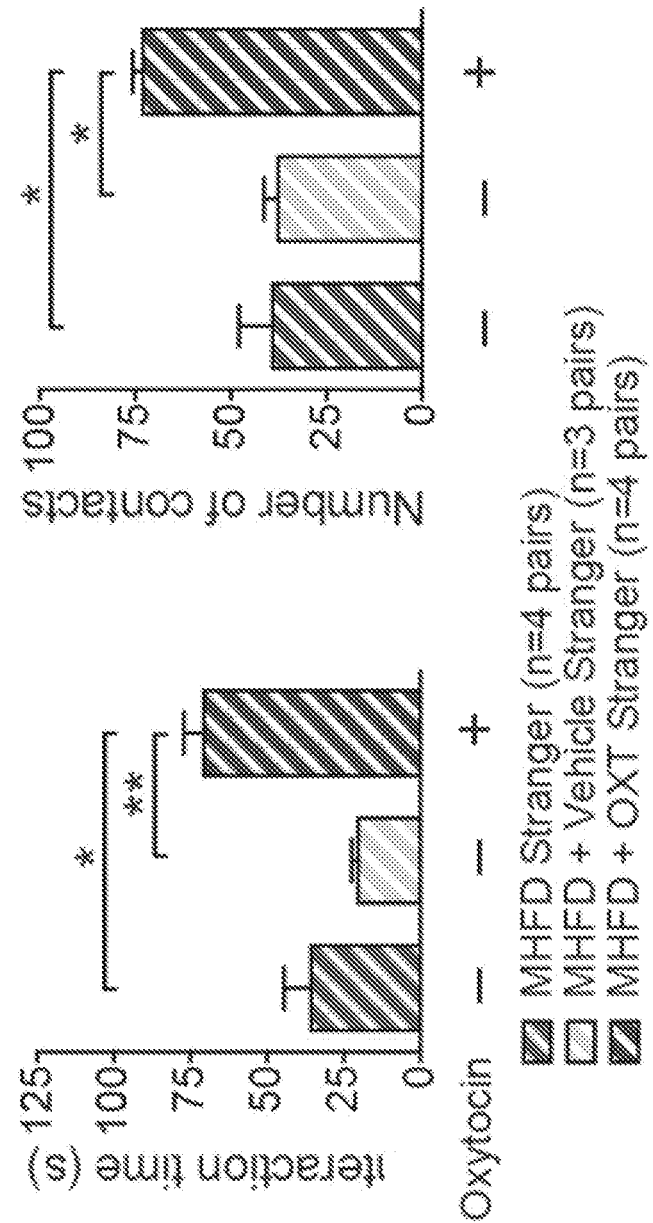

Table 1. Species whose abundance is reduced in the gut microbiota of MHFD offspring.

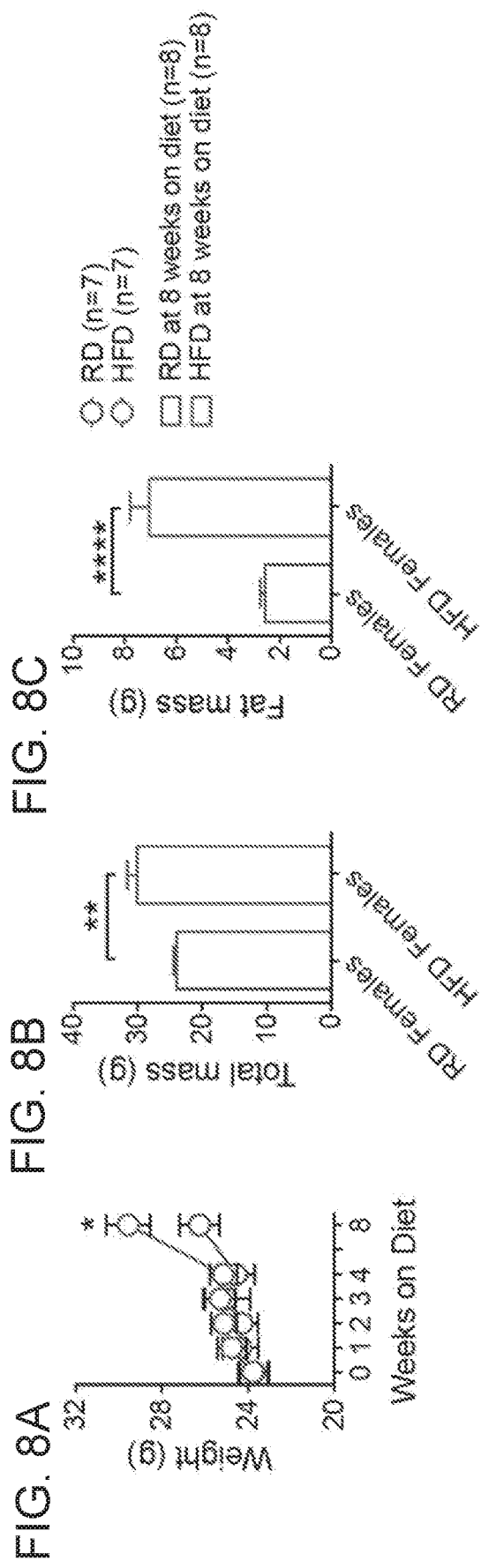

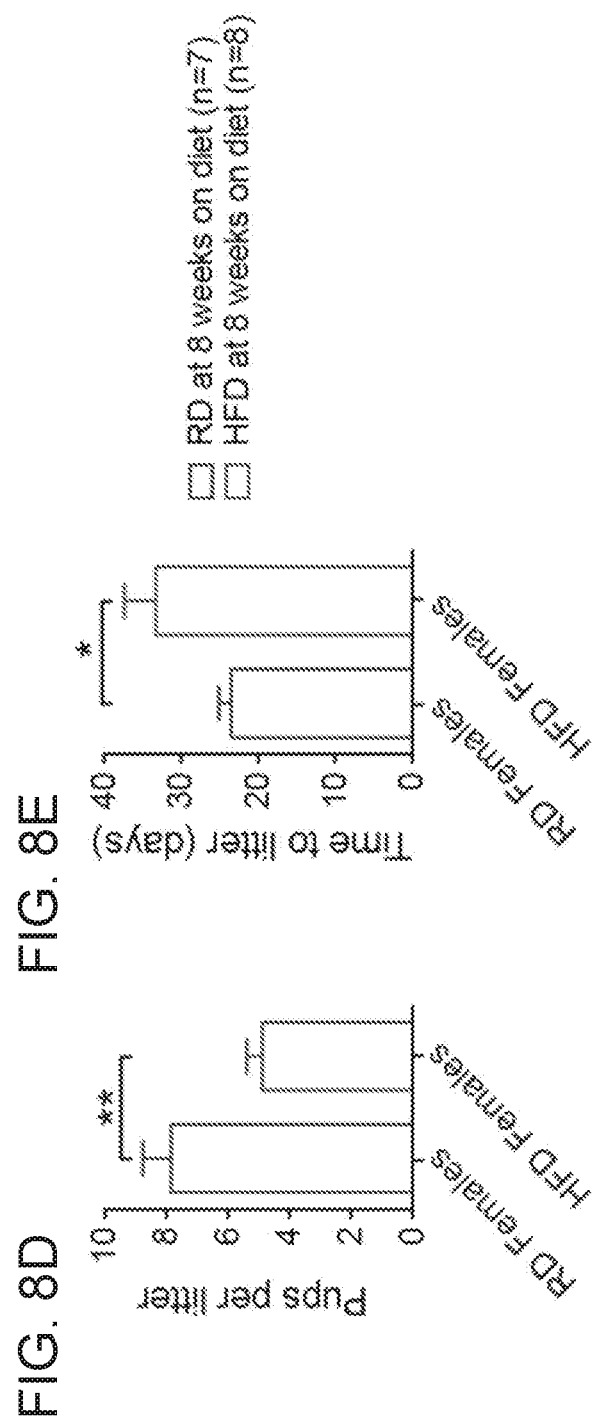

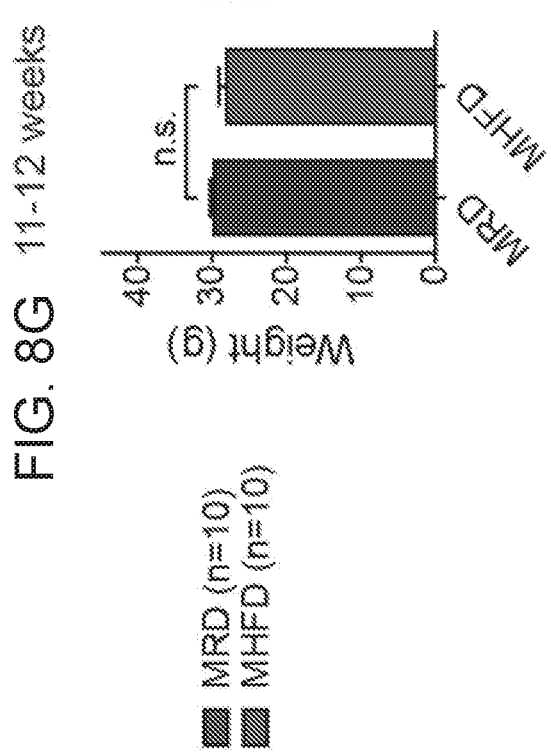
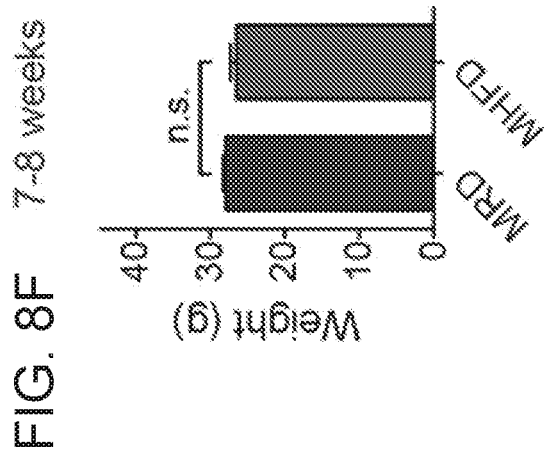

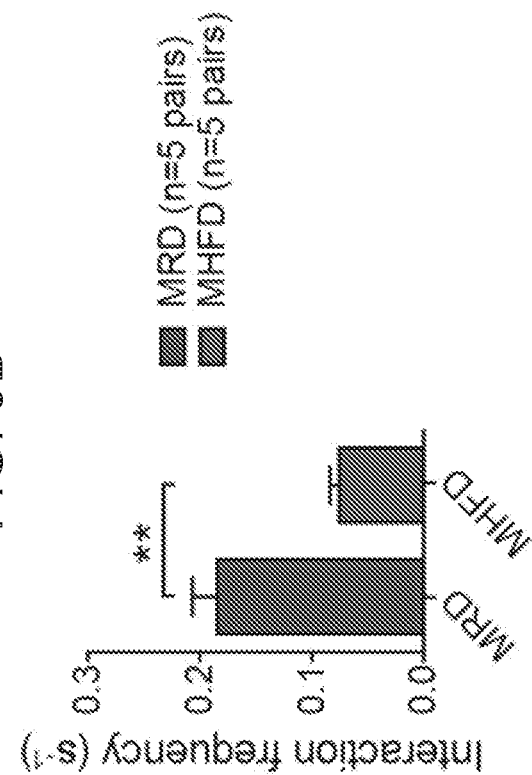
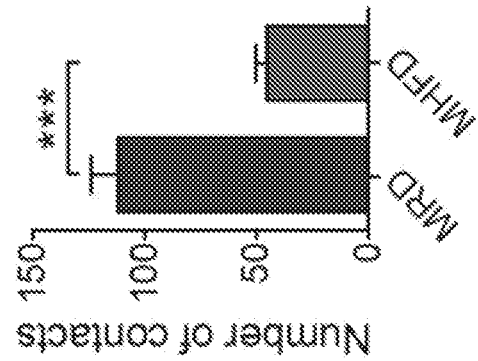
Reciprocal Social

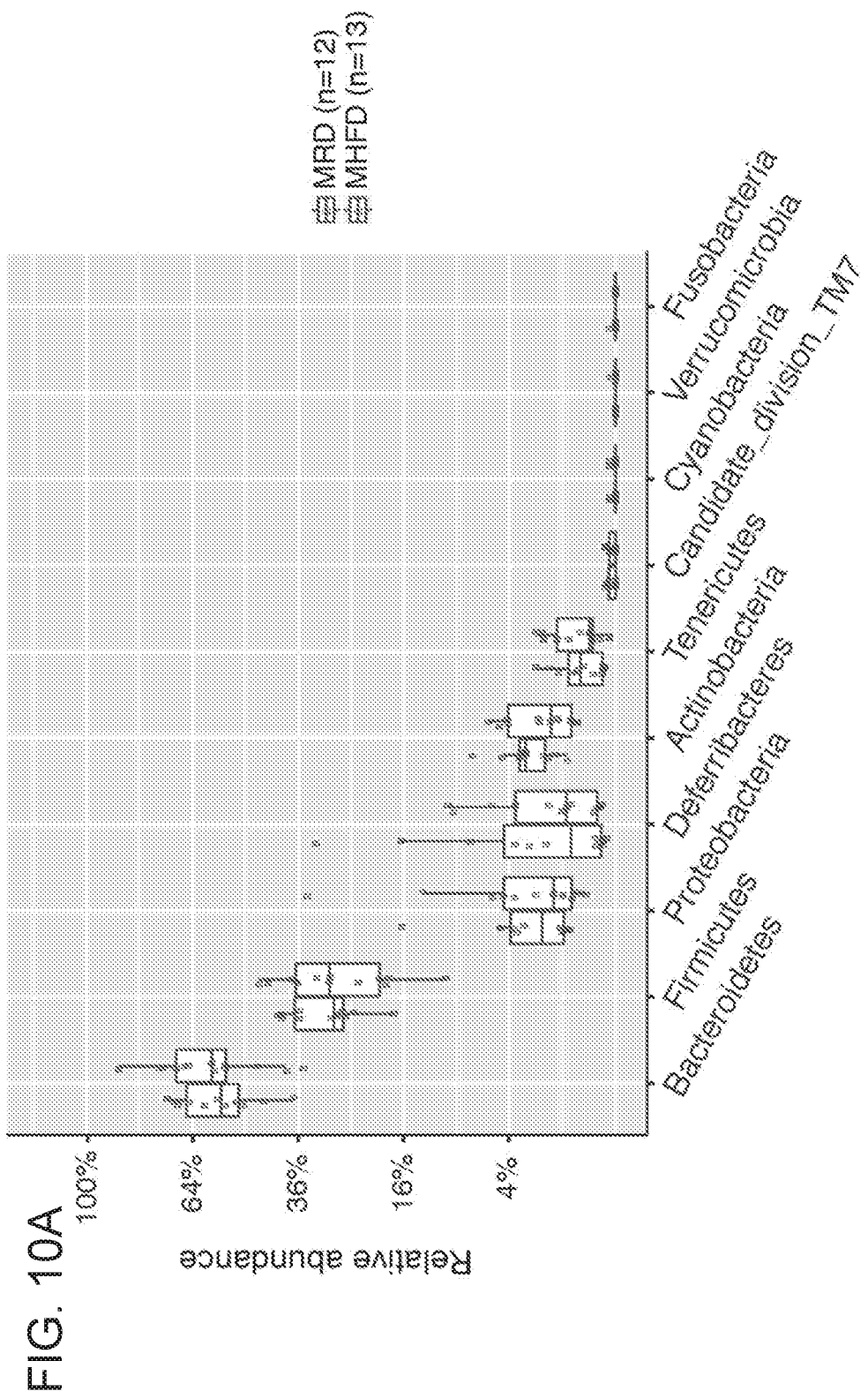

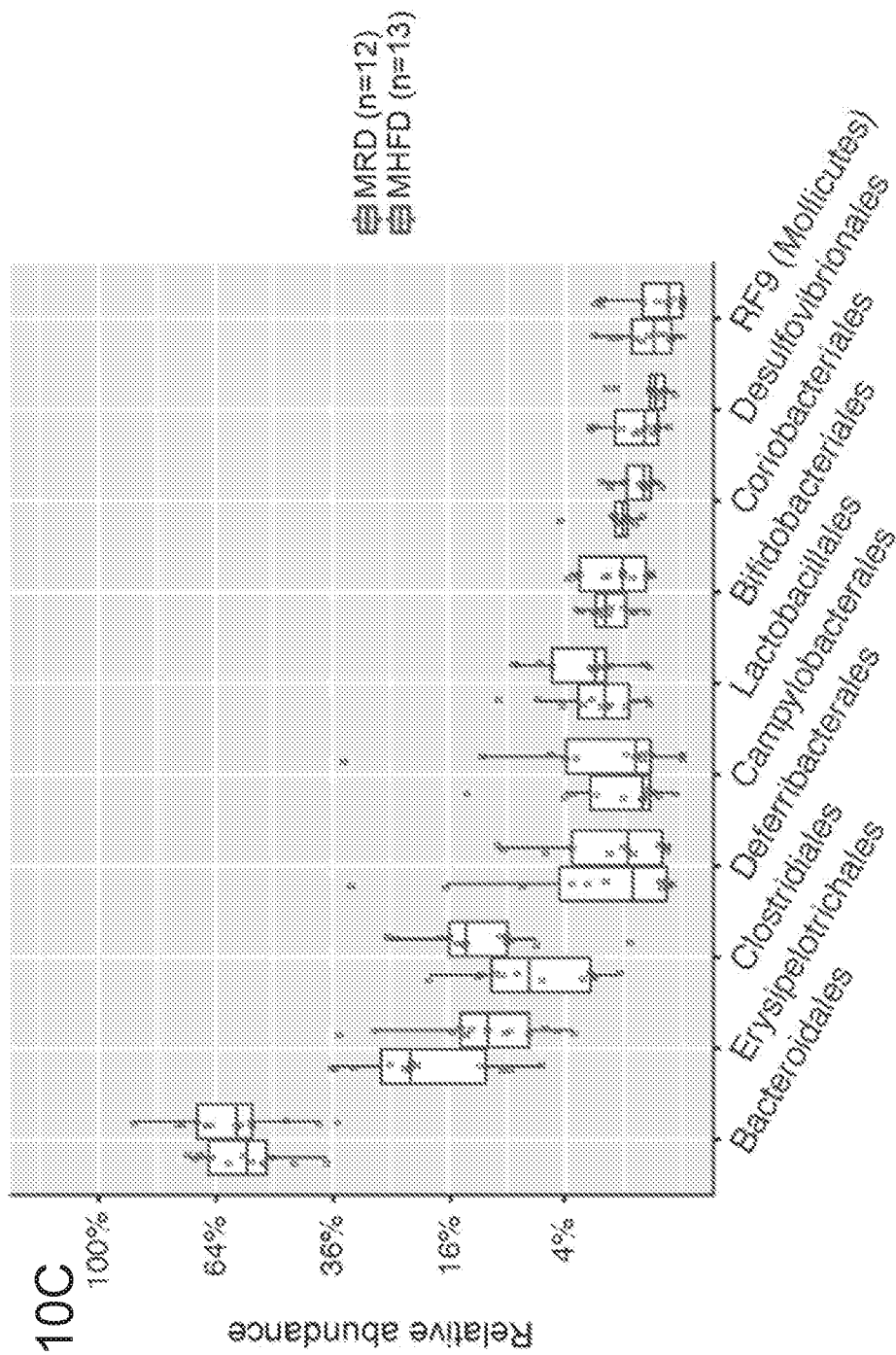

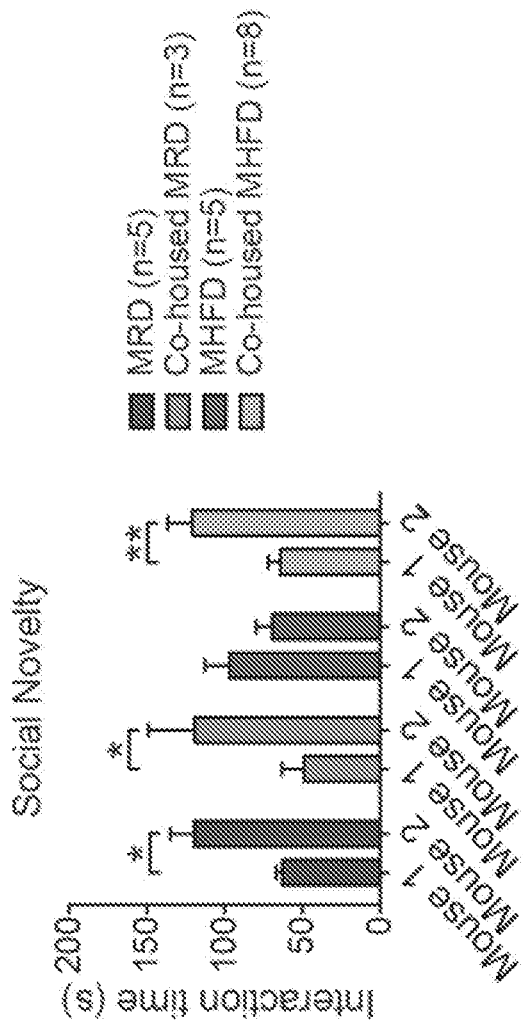
FIG. 13E
FIG. 13F
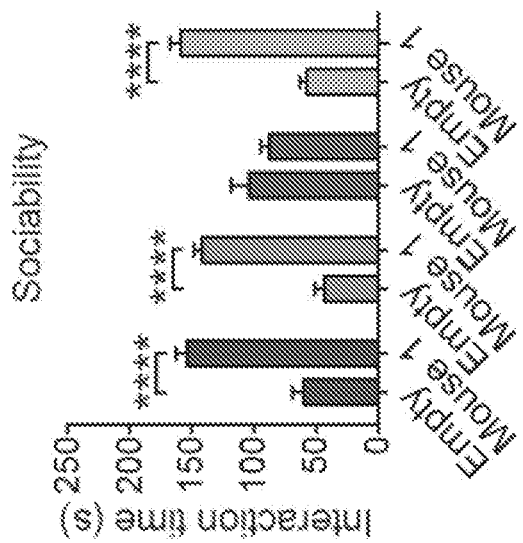

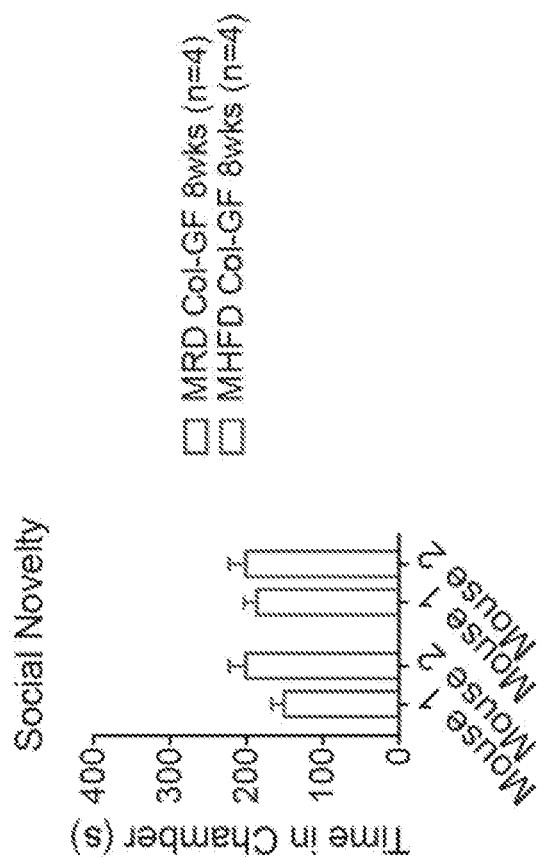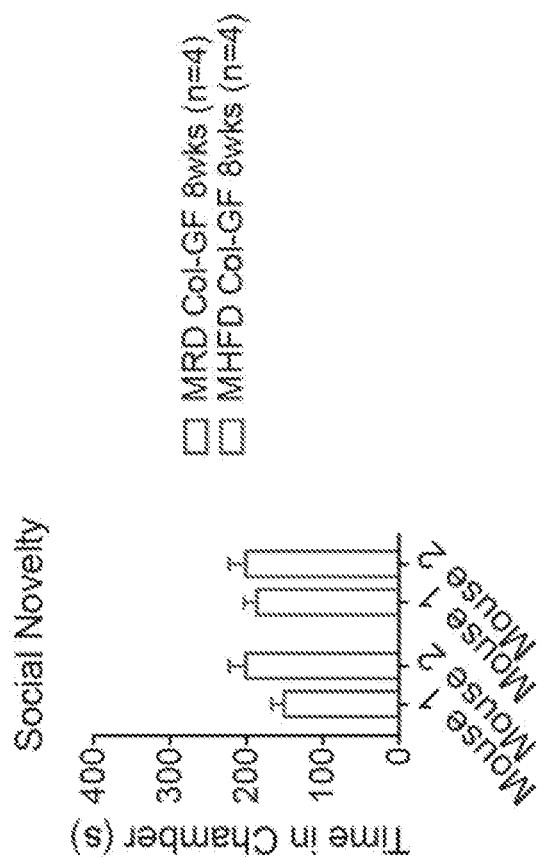
FIG. 14H
FIG. 14G

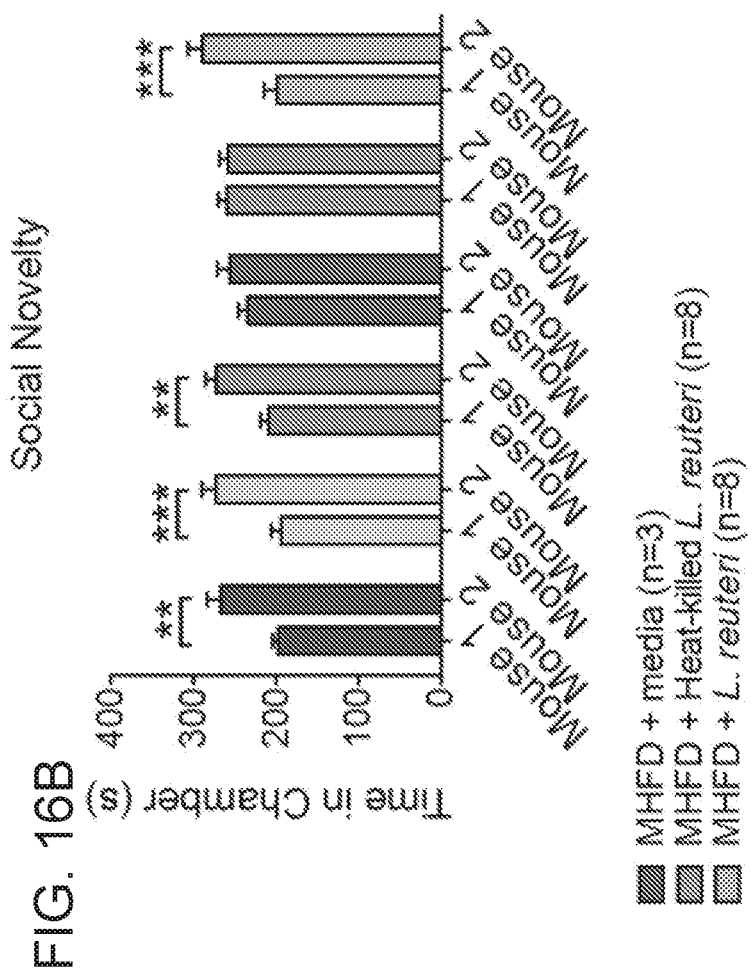

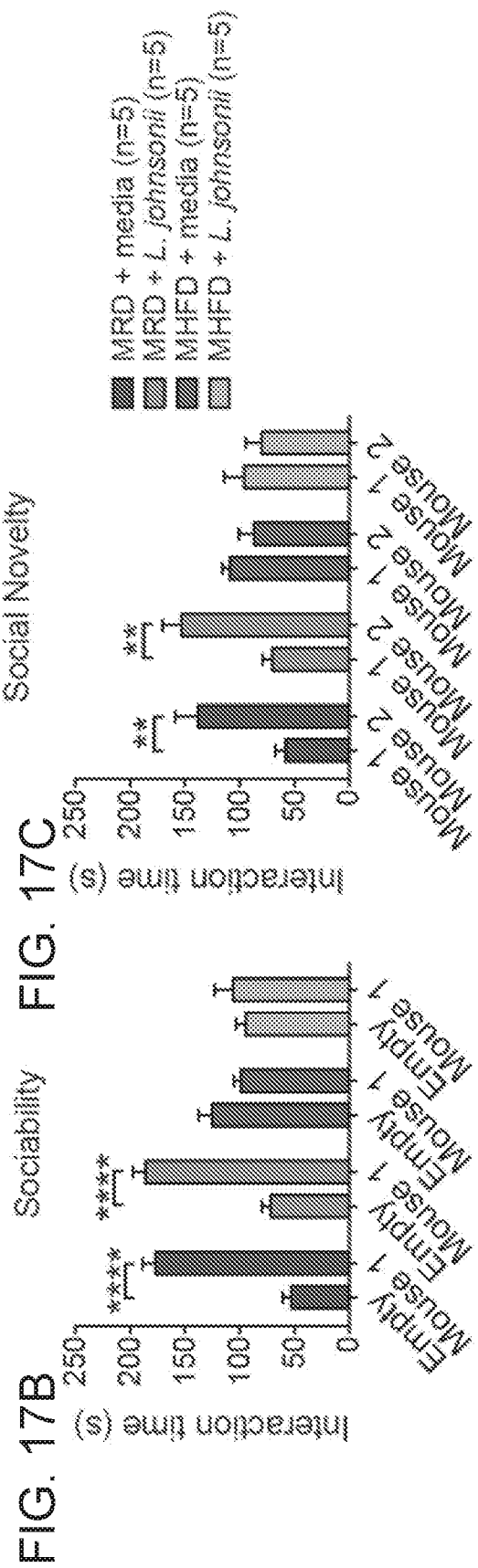

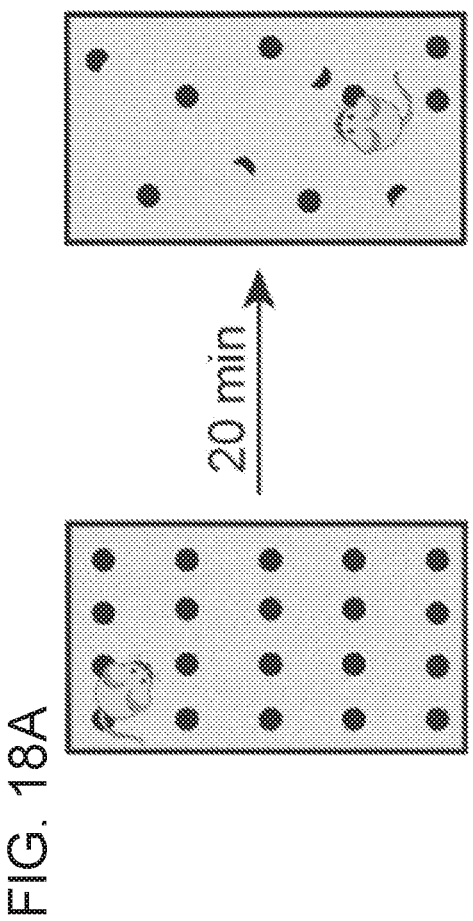

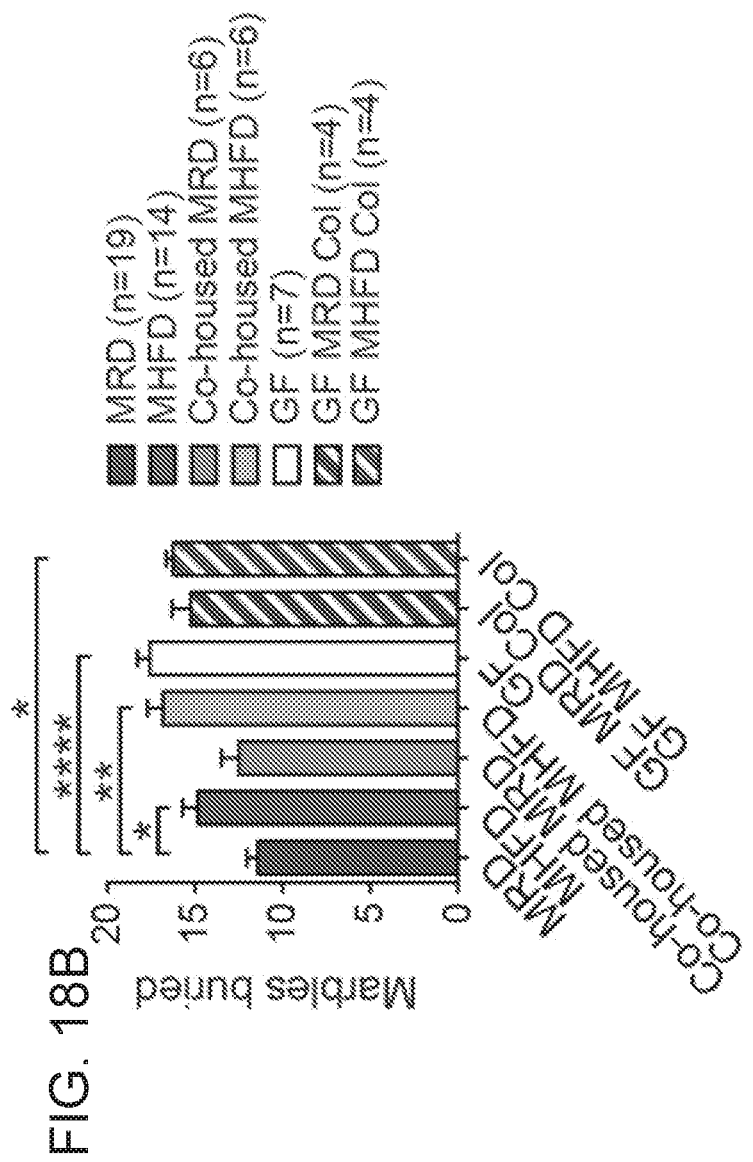

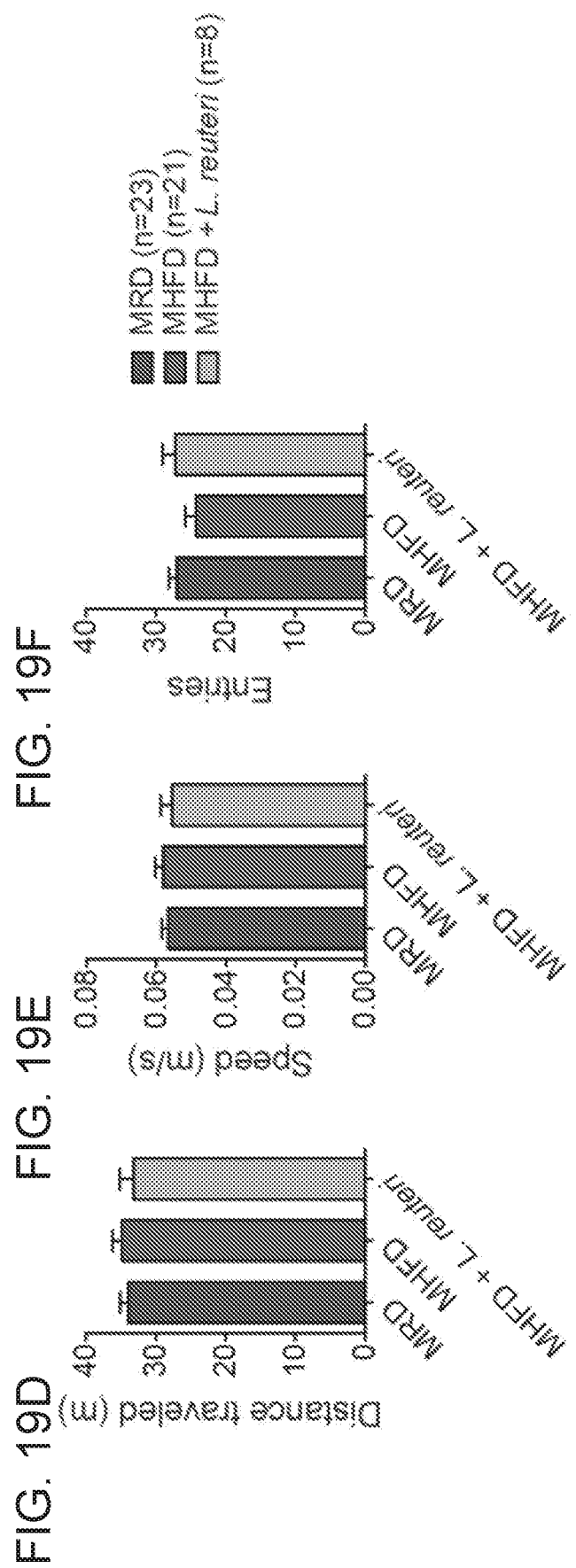

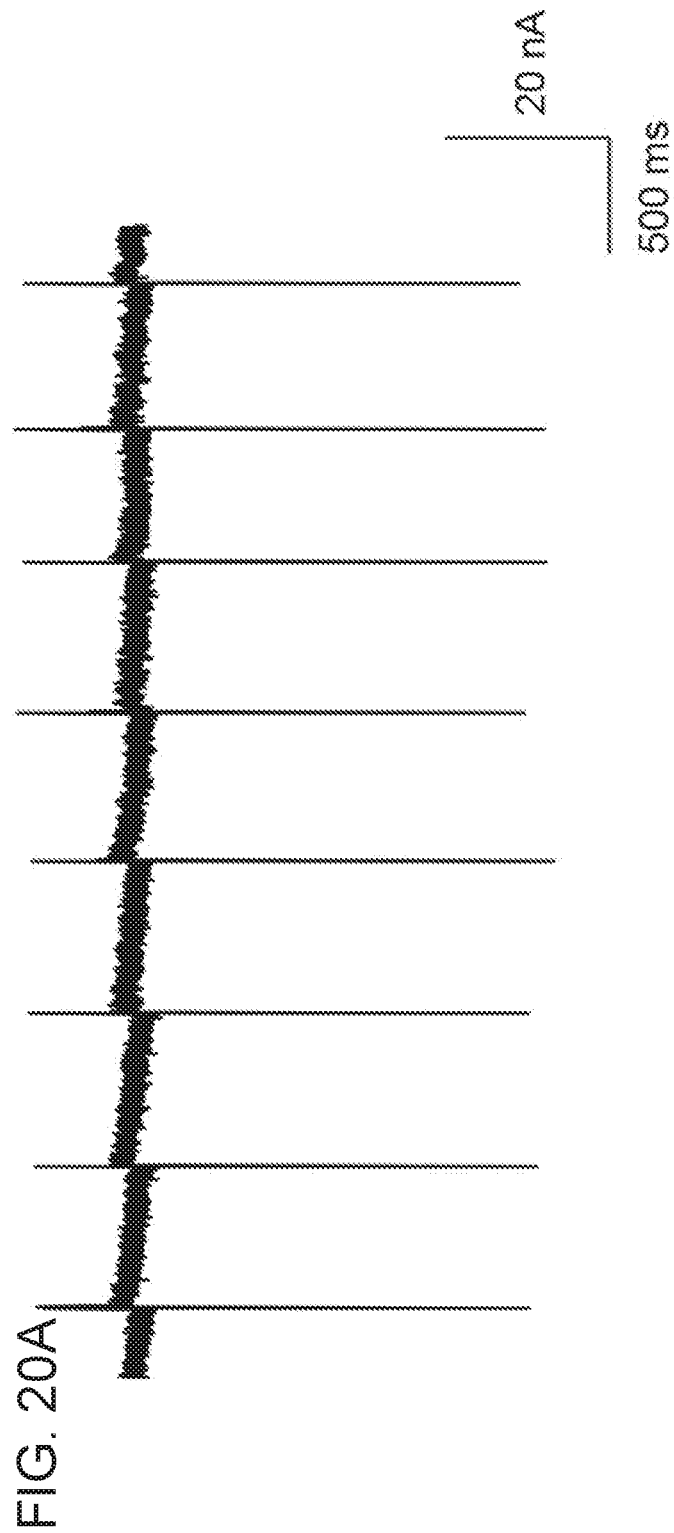

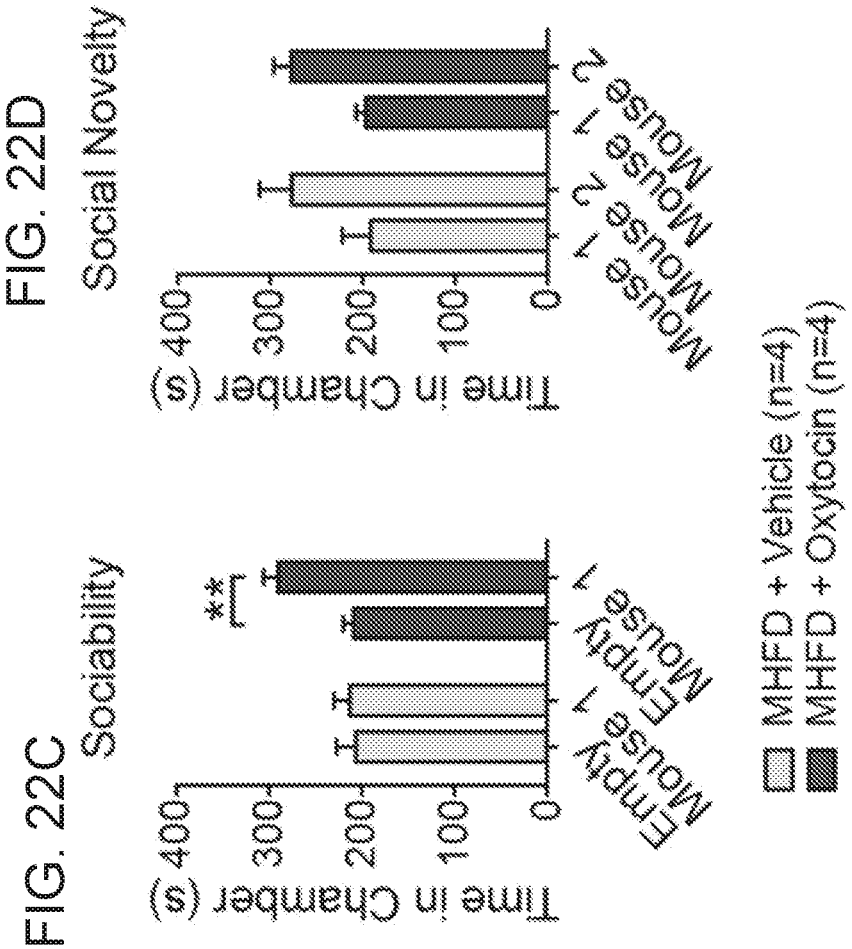

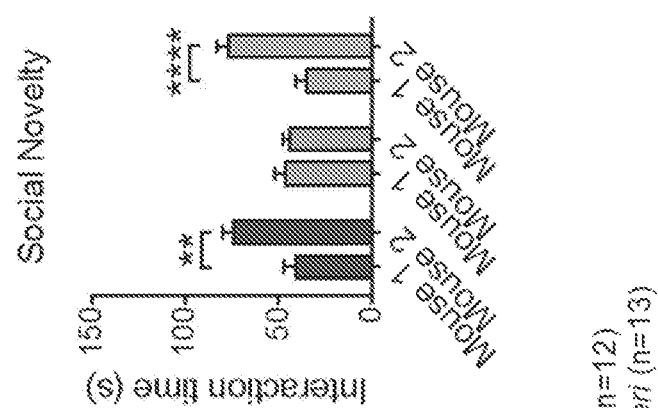
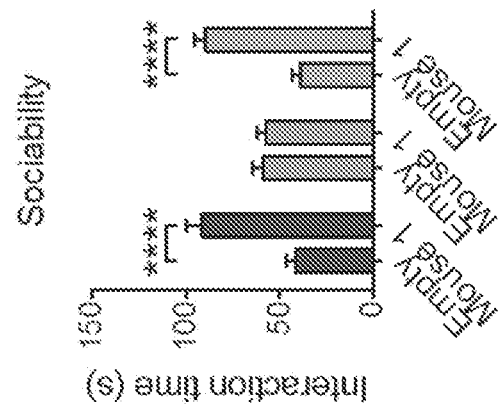
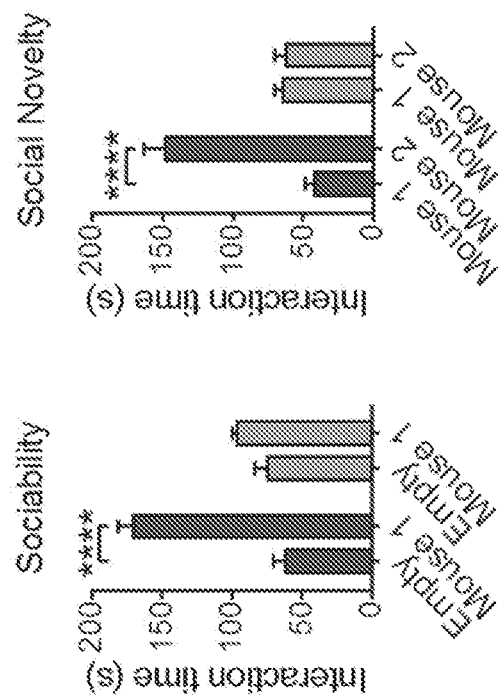
FIG. 24A, FIG. 24B, FIG. 24C, FIG. 24D

PROBIOTIC THERAPIES FOR DEVELOPMENTAL DISORDERS AND OTHER NEUROLOGICAL DISORDERS

This application is a national phase application under 35 U.S.C. § 371 that claims priority to International Application No. PCT/US2017/027827 filed Apr. 15, 2017, which claims priority to U.S. Provisional Patent Application Ser. No. 62/322,946, filed Apr. 15, 2016, all of which are incorporated herein by reference in their entirety.

C0020STATEMENT REGARDING FEDERALLY SPONSORED RESEARCH OR DEVELOPMENT

This invention was made with government support under NIMH 096816 and NINDS 076708 awarded by the National Institutes of Health. The government has certain rights in the invention.

TECHNICAL FIELD

Embodiments of the disclosure concern at least the fields of cell biology, molecular biology, biochemistry, neurology, behavior, gastroenterology, and medicine.

BACKGROUND

Recent evidence indicates that exposure to maternal obesity in utero negatively impacts the organization and maturation of the neural circuitry that is required for the development of a child's mental health. Indeed, maternal obesity and/or unhealthy maternal diets significantly increase the risk of neurodevelopmental disorders, including Autism Spectrum Disorder (ASD) in children (Bolton and Bilbo, 2014; Connolly et al., 2016; Krakowiak et al., 2012; Sullivan et al., 2014). Given the concomitant increase in the prevalence of both obesity (Skinner and Skelton, 2014) and ASD (Zablotsky et al., 2015), it is useful to understand the relationship between the two.

The amount and type of dietary macronutrients strongly influence the intestinal microbiota (Tremaroli and Backhed, 2012), which consists of a vast bacterial community that resides in the lower gut and lives in a symbiotic relationship with the host. Thus, maternal obesity is associated with alterations in the gut microbiome in offspring in both human and non-human primates (Galley et al., 2014; Ma et al., 2014). In addition, individuals with ASD often co-present with behavioral disorders, gastrointestinal problems and dysbiosis of the gut microbiota (Kohane et al., 2012; Mayer et al., 2014; Parracho et al., 2005). Given the large body of preclinical literature supporting the notion that a bidirectional communication system between the gut and the brain—known as the gut-brain axis—links gut and brain activities (Cryan and Dinan, 2012; Mayer et al., 2015), it has been speculated that changes in gut microbiome may result in ASD and related neurobehavioral disorders (Mayer et al., 2014). However, how changes in bacteria that inhabit in our intestine could influence brain development and function in ASD remains unknown.

The present disclosure satisfies a long-felt need in the art to treat neurological and neurobehavioral disorders.

BRIEF SUMMARY

Embodiments of the disclosure concern methods and compositions for treatment and/or prevention of a medical condition in which at least one symptom is a social behavior deficiency or wherein the condition is a neurodevelopmental, psychiatric and neurodegenartive disorders. Although any medical condition having a social behavior deficiency is encompassed for the disclosure, in specific embodiments the medical condition is a developmental disorder, including a neurodevelopmental disorder.

The individual may have impaired social behavior of any kind. In some cases, the neurodevelopmental disorder is autism spectrum disorder (ASD) either caused by environmental (diet, pathogen infection, exposure to toxin, pesticides, etc.) or genetic factors (mutations in genes associated with ASD and other neurological disorders), paternal/maternal age and prematurity, or any combination of these factors. In specific embodiments, the individual was born from a mother that is obese, overweight, and/or is on a high-fat diet, undergoes immune activation during pregnancy, although in some cases the individual was born from a mother that was not obese, not overweight, and/or not on a high-fat diet. In other cases, the individual (mother or parent) carries mutations associated with neurodevelopmental disorders. In other cases, the mother or individual exhibit an altered gut microbiota or show alternation in oxytocin levels.

In particular embodiments, an individual in need of treatment and/or prevention of a social behavior deficiency, neurodevelopmental, psychiatric and neurodegenartive disorders of any cause is provided an effective amount of one or more bacteria species to treat and/or prevent one or more social behavior deficiencies. In some cases the treatment results in improving the social behavior deficiency, and in specific cases results in improving the social behavior deficiency to within a normal spectrum.

Certain embodiments of the disclosure provide for modifying the gut microbiome of an individual to improve one or more social behavior deficiencies, neurodevelopmental, and/or psychiatric disorders in the individual. Other embodiments of the disclosure provide for modifying the gut microbiome of an individual to improve a neurodevelopmental disorder in an individual. In specific cases, the level of at least one microbe in the gut microbiome is altered to improve one or more social behavior deficiencies. In some cases, the individual may or may not have been born from a mother that was obese, overweight, and/or that was on a high-fat diet. In specific embodiments, the bacteria is from the *Lactobacillus* genus. In other cases the individual carries mutation(s) associated with neurodevelopmental disorders. In particular cases, the *Lactobacillus* species is *L. reuteri*, and the *L. reuteri* may be delivered as a single species or as one of multiple species of non-pathogenic bacteria. The individual whose mother or father is obese, overweight, and/or that was on a high-fat diet or individual carrying mutations associated with neurodevelopmental disorders, may be provided with an effective amount of *L. reuteri* before and/or after being born. In some cases, a pregnant female may be provided with an effective amount of *L. reuteri*, and in such cases her offspring may be provided with an effective amount of *L. reuteri* before and/or after being born. A fetus may have improvement of the gut microbiome upon receipt of one or more bacteria by the mother, for example through the placenta and/or blood circulation.

Embodiments of the disclosure provide that specific microbiome reconstitution reverses maternal diet-induced synaptic deficits in addition to or alternative to social behavioral deficits in the offspring. The offspring may be a singleton birth or birth of multiples. The individual may be of any race or gender, and the mother may be of any age, race, or gender.

In one embodiment there is provided a method of treating or preventing in an individual with one or more social behavioral deficiencies, neurodevelopmental, and/or psychiatric disorders, comprising the steps of providing to the individual and/or the mother during gestation of the individual a therapeutically effective amount of a formulation comprising *Lactobacillus*, and an example of *Lactobacillus* is *Lactobacillus reuteri*. In a specific embodiment, when providing the formulation to the individual, the mother of the individual was obese, overweight, and/or on a high-fat diet during the pregnancy with the individual. In some cases, a formulation is provided to the mother during gestation of the individual. In specific embodiments, the social behavioral deficiency comprises impaired sociability, preference for social novelty, difficulty in social use of verbal and nonverbal communication, or a combination thereof. The individual may have a neurodevelopment disorder. The individual may have autism spectrum disorder. In some cases, the method further comprises the step of identifying that the mother is or was obese, overweight, and/or on a high-fat diet during pregnancy with the individual and wherein the formulation is provided to the individual or mother intentionally to treat or prevent the social behavior deficiency in the individual. In specific cases, the individual that was born or is being carried by a mother that is or was obese, overweight, and/or on a high-fat diet may be specifically recognized as being in need of treatment with *Lactobacillus*, such as *L. reuteri*. In certain cases, the mother and/or child is administered *Lactobacillus* for treatment but the *Lactobacillus* is not *L. acidophilus* in the form of yogurt.

Any formulation encompassed by the disclosure may comprise an additional bacteria species or a yeast.

Methods of the disclosure include treatment or prevention of one or more disorders in which the oxytocinergic system is dysfunctional. Methods of the disclosure include prevention or treatment of one or more conditions in which the dopaminergic and reward system are usurped or dysfunctional.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

FIGS. 1A-1J: Social Deficits and Dysbiosis of the Gut Microbiota in MHFD Offspring. FIG. 1A, Schematic of the maternal diet regimen and breeding. FIG. 1B, Schematic of the reciprocal social interaction task. FIGS. 1C-1D, MHFD offspring showed reduced reciprocal interaction (1C, $P<0.0001$, $t=7.90$; D, $P<0.001$, $t=5.89$). FIG. 1E, Schematic of the three-chamber social interaction task. FIGS. 1F-1G, In the sociability test, MRD offspring spent more time interacting with a mouse than with an empty wire cage (FIG. 1F, $P<0.0001$, $t=8.817$), whereas MHFD offspring showed no preference for the mouse (FIG. 1F, $P=0.48$, $t=1.19$; Maternal diet effect $F1,52=6.08$, $P<0.05$). In the social novelty test, unlike MRD (FIG. 1G, $P<0.0001$, $t=6.68$), MHFD offspring had no preference for interacting with a novel versus a familiar mouse (FIG. 1G, $P=0.086$, $t=2.08$; Maternal diet effect $F1, 52=34.96$, $P<0.0001$). FIGS. 1H-1I, Representative exploratory activity of MRD (FIG. 1H) and MHFD (FIG. 1I) offspring in the three-chamber test. FIG. 1J, Principal coordinates analysis (PCoA) of unweighted UniFrac distances from the averaged rarefied 16S rRNA gene dataset (n=1,000 rarefactions; 7,617 reads/sample) showed that MRD samples clustered separately from MHFD samples ($P<0.001$, $R2=0.37$). Plots show mean±SEM. See also FIGS. 8A-8G-11A-11B.

FIGS. 2A-2G: Co-housing MHFD with MRD Offspring Rescues both Social Dysfunction and the Microbiota Phylogenetic Profile of MHFD Mice. FIG. 2A, Schematic of the cohousing experiment. FIG. 2B, MRD and MHFD offspring were weaned into one of three cage compositions. FIGS. 2C-2G, Social interaction time (FIG. 2C, MRD vs. MHFD $P<0.001$, $t=9.30$; MRD vs. co-housed MHFD $P>0.99$, $t=0.31$; MHFD vs. co-housed MHFD $P<0.001$, $t=7.99$; $P<0.0001$, $F3,8=30.51$) and contact duration (FIG. 2D, MRD vs. MHFD $P<0.05$, $t=4.13$; MRD vs. co-housed MHFD $P>0.99$, $t=0.46$; MHFD vs. co-housed MHFD $P<0.05$, $t=4.59$; $P<0.001$, $F3,8=9.01$) in the reciprocal interaction test; social interaction times in the sociability (FIG. 2E, MRD $P<0.001$, $t=4.36$; MHFD $P>0.99$, $t=0.078$; Co-housed MRD $P<0.0001$, $t=6.33$; Co-housed MHFD $P<0.001$, $t=4.78$; Maternal diet/Housing/Interaction effect $F3,32=6.13$, $P<0.01$) and social novelty tests (FIG. 2F, MRD $P<0.0001$, $t=5.12$; MHFD $P>0.99$, $t=0.60$; Co-housed MRD $P<0.001$, $t=4.20$; Co-housed MHFD $P<0.001$, $t=4.76$; Maternal diet/Housing/Interaction effect $F3,32=4.37$, $P<0.01$), as well as UniFrac-based phylogenetic clustering (FIG. 2G, $P<0.001$, $R2=0.552$; n=1,000 rarefactions; 3,390 reads/sample), are all restored in MHFD offspring co-housed with MRD mice. Plots show mean±SEM. See also FIGS. 12A-12D and FIGS. 13A-13G.

FIGS. 3A-3L: Fecal Microbiota from MRD, but not MHFD, Offspring Improves Germ-Free (GF) Recipient Social Behavior. FIGS. 3A-3D, GF mice show reduced reciprocal social interaction (FIG. 3A, $P<0.0001$, $t=22.73$; FIG. 3B, $P<0.001$, $t=11.31$) and deficits in sociability (FIG. 3C, Control $P<0.0001$, $t=5.30$, GF $P>0.99$, $t=0.39$; Main group effect $F1,24=21.98$, $P<0.0001$) and preference for social novelty (FIG. 3D, Control $P<0.01$, $t=3.64$, GF $P=0.39$, $t=1.33$; Main group effect $F1,24=5.29$, $P<0.05$). Schematic of fecal microbiota transplant (FMT) at four (FIG. 3E) and eight weeks of age (FIG. 3F). FIGS. 3G-3H, FMT from MRD, but not MHFD, offspring at weaning restored both GF sociability (FIG. 3G, GFMRDCol $P<0.0001$, $t=6.66$; GFMHFDCol $P=0.35$, $t=1.40$; Donor effect $F1,28=32.44$, $P<0.0001$) and preference for social novelty (FIG. 3H, GFMRDCol $P<0.01$, $t=3.60$; GFMHFD-Col $P=0.81$, $t=0.84$; Donor effect $F1,28=9.86$, $P<0.01$). FIGS. 3I-3J, At eight weeks, FMT from either MRD or MHFD donors failed to improve sociability (FIG. 3I, GFMRDCol $P=0.51$, $t=1.20$; GFMHFDCol $P=0.28$, $t=1.58$; Donor effect $F1,12=0.07$, $P=0.79$) or preference for social novelty in GF mice (FIG. 3J, GFMRDCol $P=0.48$, $t=1.23$;

GFMHFDCol P>0.99, t=0.043; Donor effect F1,12=0.71, P=0.42). FIGS. 3K-3L, PCoA of unweighted UniFrac distances based on the 16S rRNA gene sequencing dataset from GF recipients of stools from either MRD or MHFD donors at four (3K, P=0.001, R2=0.83; n=1,000 rarefactions; 4,628 reads/sample) or eight (3L, P<0.001, R2=0.77; n=1,000 rarefactions; 4,805 reads/sample) weeks of age. Plots show mean±SEM. See also FIGS. 14A-14H and 15A-15F.

FIGS. 4A-4P: Selective Treatment with Lactobacillus (L.) reuteri Restores Social Deficits and Oxytocin Levels in MHFD Offspring. FIG. 4A, Schematic of L. reuteri-treatment. FIGS. 4B,4C, Unlike resuspension media (FIG. 4B, P>0.99, t=1.03; c, P>0.99, t=0.40) or heat-killed L. reuteri (FIG. 4B, P>0.99, t=1.35; c, P>0.99, t=0.21), administration of live L. reuteri in the drinking water rescued sociability (FIG. 4B, P<0.0001, t=5.98) and preference for social novelty (FIG. 4C, P<0.001, t=5.01) in MHFD offspring (FIG. 4B, Treatment effect F1,86=87.53, P<0.0001; FIG. 4C, Treatment effect F1,86=30.24, P<0.0001). FIG. 4F, Representative images of control oxytocin immunoreactivity at different anteroposterior levels of the PVN. FIGS. 4G-4J, Oxytocin immunoreactivity in the PVN of MRD (FIG. 4G), MHFD (FIG. 4H), heat-killed L. reuteri-treated MHFD (FIG. 4I), and live L. reuteri-treated MHFD offspring (FIG. 4J). FIGS. 4K-4N, Oxytocin immunoreactive cell number (FIG. 4K, P<0.01, t=4.76) and oxytocin immunofluorescence intensity (FIG. 4L, P<0.01, t=3.80) were reduced in the PVN of MHFD versus MHFD mice. In the PVN of MRD and MHFD offspring, NeuN cell number immunoreactivity (FIG. 4M, P=0.34, t=1.09) and immunofluorescence intensity (FIG. 4N, P=0.79, t=0.28) were similar. FIGS. 4O-4P, Relative to treatment with heat-killed L. reuteri, treatment with live L. reuteri significantly increased oxytocin-positive cell number (FIG. 4O, P<0.05, t=2.93) and oxytocin immunofluorescence intensity (FIG. 4P, P<0.05, t=3.09) in the PVN of MHFD offspring. AU: arbitrary units. Plots show mean±SEM. See also FIGS. 16A-16C-FIGS. 19A-19F.

FIGS. 5A-5L: Reciprocal Social Interaction and Social Interaction-Induced LTP in MHFD Offspring VTA DA Neurons are Restored by L. reuteri. FIG. 5A, Schematic of the experimental design. FIGS. 5B-5E, Only interaction with a stranger mouse induced LTP in MRD VTA DA neurons, as determined by increased AMPAR/NMDAR ratios (FIGS. 5B,5D, Baseline vs. Familiar P>0.99, t=0.12, Baseline vs. Stranger P<0.01, t=3.79; Familiar vs. Stranger P<0.05, t=3.03; 5F=8.03, P<0.01). In MHFD offspring, neither stranger nor familiar reciprocal interaction evoked LTP in VTA DA neurons (FIGS. 5C,5E, Baseline vs. Familiar P>0.99, t=0.035, Baseline vs. Stranger P=0.64, t=1.30; Familiar vs. Stranger P=0.50, t=1.45; F2,15=1.47, P=0.26). FIGS. 5F-5G, Whereas MRD mice spent more time interacting with a stranger than a familiar mouse (Familiar vs. Stranger; FIG. 5F, P<0.001, t=4.88; FIG. 5G, P<0.0001, t=5.87), MHFD mice did not (Familiar vs. Stranger; FIG. 5F, P=0.47, t=1.87; FIG. 5G, P=0.40, t=1.96) (FIG. 5F, F3,19=13.8, P<0.0001; FIG. 5G, F3,19=18.54, P<0.0001). FIGS. 5H-5K, Live (FIGS. 5H,5J, P<0.01, t=4.95), but not heat-killed L. reuteri (FIGS. 5I,5K, P=0.84, t=0.20), restored stranger interaction-evoked LTP in the VTA of MHFD offspring. FIG. 5L, Unlike heat-killed L. reuteri (MHFD vs. MHFD+Hk-Lr P>0.99, t=0.099), live L. reuteri restored reciprocal social interaction (MHFD vs. MHFD+Lr P<0.05, t=3.24; F2,9=6.45, P<0.05). Plots show mean±SEM. See also FIGS. 20A-20C-FIGS. 22A-22D.

FIGS. 6A-6F: Oxytocin Restores Social Interaction-Induced VTA Plasticity and Social Behavioral Deficits in MHFD Offspring. FIGS. 6A-6B, Intranasal oxytocin administration rescued LTP in the VTA of MHFD offspring (FIG. 6B, MHFD+OXT Alone vs. MHFD+OXT Stranger P<0.01, t=3.66; MHFD+Vehicle Stranger vs. MHFD+OXT Stranger P<0.05, t=2.86; F2,15=7.97, P<0.01). FIGS. 6C-6F, Oxytocin also restored reciprocal social interaction (FIG. 6C, MHFD vs. MHFD+Vehicle P=0.55, t=1.46; MHFD vs. MHFD+OXT P<0.05, t=3.62; MHFD+Vehicle vs. MHFD+OXT P<0.01, t=4.81; F2,8=12.82, P<0.01; FIG. 6D, MHFD vs. MHFD+Vehicle P>0.99, t=0.16; MHFD vs. MHFD+OXT P<0.05, t=4.075; MHFD+Vehicle vs. MHFD+OXT P<0.05, t=3.94; F2,8=10.97, P<0.01), sociability (FIG. 6E, MHFD+Vehicle P>0.99, t=0.44; MHFD+Oxytocin P=0.24, t=1.74; Treatment effect F1,8=2.37, P=0.16) and preference for social novelty in MHFD offspring (FIG. 6F, MHFD+Vehicle P=0.65, t=1.05; MHFD+Oxytocin P<0.05, t=3.54; Treatment effect F1,8=10.54, P<0.05). Plots show mean±SEM. See also FIGS. 22A-22D.

FIGS. 8A-8G: High Fat Diet Increases the Weight of Mothers but not Offspring, Related to FIGS. 1A-1J. FIGS. 8A-8B, Female mice fed a high fat diet (HFD) showed a >25% increase in weight compared to regular diet (RD)-fed females after 8 weeks on diet (FIG. 8A, P<0.05, t=2.42; FIG. 8B, P<0.01, t=3.90). FIG. 8C, HFD-fed females showed increased fat mass relative to RD dams (FIG. 8C, P<0.0001, t=5.80). FIGS. 8D-8E, Compared to RD-, HFD-fed female litter size was decreased (FIG. 8D, P<0.01, t=3.18) and time to first litter increased (FIG. 8E, P<0.05, t=2.26). FIGS. 8F-8G, Offspring weight did not differ between maternal diet cohorts at either seven-eight (FIG. 8F, P=0.12, t=1.63) or eleven-twelve weeks of age (FIG. 8G, P=0.10, t=1.80), the age range during which behavioral tests were performed. Plots show mean±SEM.

FIGS. 9A-9D: Impaired Social Behaviors in MHFD Offspring, Related to FIGS. 1A-1J. FIGS. 9A-9B, MHFD offspring showed reduced contact number (FIG. 9A, P<0.001, t=5.10) and frequency (FIG. 9B, P<0.01, t=4.73) in the reciprocal social interaction test. FIGS. 9C-9D, In the three-chamber test, MHFD mice show impaired sociability (FIG. 9C, MRD P<0.01, t=3.67, MHFD P=0.15, t=1.81; Maternal diet effect F1,52=15.00, P<0.001) and preference for social novelty (FIG. 9D, MRD P<0.001, t=4.28, MHFD P=0.053, t=2.29; Maternal diet effect F1,52=21.53, P<0.0001). Plots show mean±SEM.

FIGS. 10A-10F: MHFD Offspring Gut Microbiome Show no High Level Taxonomic Changes, but Bacterial Diversity is Reduced, Related to FIGS. 1A-1J. FIGS. 10A-10D, Relative abundance of the top 10 most abundant Phyla, as identified by 16S rRNA gene analysis, did not significantly differ between maternal diet cohorts (FIGS. 10A,10B, Bacteroidetes P=0.50; Firmicutes P=0.94; Proteobacteria P=0.64; Deferribacteres P=0.91; Actinobacteria P=0.20; Tenericutes P=0.83; Candidate_division_TM7 P=0.73; Cyanobacteria P=0.97; Verrucomicrobia P=0.38; Fusobacteria P=0.37) and Orders (FIGS. 10C,10D, Bacteroidales P=0.67, Erysipelotrichales P=0.32, Clostridiales P=0.32; Deferribacterales P=1; Campylobacterales P=1; Lactobacillales P=0.68; Bifidobacteriales P=0.78; Coriobacteriales P=0.23; Desulfovibrionales P=0.49; RF9 P=0.56). FIG. 10E, PCoA of weighted UniFrac distances from the averaged, rounded rarefied MRD and MHFD 16S rRNA gene dataset (n=1,000 rarefactions; 7,617 reads/sample). Weighted assessment of community structure showed overlap between the two maternal diet cohorts (FIG. 10E, P=0.18, R2=0.063). FIG. 10F, Substantially fewer operational taxonomic units (OTUs) were identified among the MHFD versus MRD offspring samples, indicating reduced microbial diversity in MHFD offspring (P<0.01, t=3.41). Plot shows mean±SEM.

FIG. 11A, PCoA of unweighted UniFrac distances generated from the averaged, rounded rarefied 16S rRNA gene dataset (n=1,000 rarefactions; 2,397 reads/sample). The microbial composition of maternal fecal samples clustered together immediately prior to diet administration, but within four weeks on diet, HFD-fed maternal fecal samples clustered separately from controls. This shift in microbial composition was maintained after eight weeks on diet, when breeding started (P<0.001, R2=0.79). FIG. 11B, While bacterial diversity did not differ prior to diet onset (P=0.61, t=1.30), it was significantly reduced in HFD-fed females after four (P<0.05, t=2.82) and eight weeks on diet (P<0.0001, t=5.78). Plots show mean±SEM.

FIGS. 12A-12B, Co-housing with MRD offspring improved MHFD offspring reciprocal social interaction contact number (FIG. 12A, MRD vs. MHFD P<0.01, t=5.92; MRD vs. Co-housed MHFD P=0.32, t=2.27; MHFD vs. Co-housed MHFD P<0.05, t=3.65; F3,8=12.10, P<0.01) and frequency of interaction (FIG. 12B, MRD vs. MHFD P<0.01, t=5.89; MRD vs. Co-housed MHFD P=0.32, t=2.26; MHFD vs. Co-housed MHFD P<0.05, t=3.63; F3,8=11.99, P<0.01). FIGS. 12C-12D, Co-housing with MRD improved MHFD offspring sociability (FIG. 12C, MRD P<0.01, t=3.97; Co-housed MRD P<0.01, t=3.53; MHFD P=0.79, t=1.31; Co-housed MHFD P=0.086, t=2.42; Maternal diet/Housing effect F1,32=13.42, P<0.001) and preference social novelty (FIG. 12D, MRD P<0.01, t=3.66; Co-housed MRD P<0.05, t=2.91; MHFD P=0.67, t=1.41; Co-housed MHFD P<0.01, t=3.83; Maternal diet/Housing effect F1,32=47.73, P<0.0001). Plots show mean±SEM.

FIGS. 13A-13G: Co-housing Three MHFD with a Single MRD Offspring Rescues Social Deficits and Phylogenetic Profile of the MHFD Mice, Related to FIGS. 2A-2G. FIG. 13A, Schematic of the co-housing experiment. FIG. 13B, MRD and MHFD offspring were weaned into one of three cage compositions, as shown. FIGS. 13C-13G, Social interaction time (FIG. 13C, MRD vs. MHFD P<0.0001, t=10.21; MRD vs. co-housed MHFD P>0.99, t=1.41; MHFD vs. cohoused MHFD P<0.0001, t=8.53; P<0.0001, F3,8=38.88) and contact duration (FIG. 13D, MRD vs. MHFD P<0.0001, t=7.18; MRD vs. co-housed MHFD P>0.99, t=0.59; MHFD vs. cohoused MHFD P<0.001, t=6.29; P=0.0001, F3,8=19.14) in the reciprocal interaction test; sociability (FIG. 13E, MRD P<0.0001, t=7.37; MHFD P=0.802, t=1.31; Co-housed MRD P<0.0001, t=6.02; Co-housed MHFD P<0.0001, t=9.46; Maternal diet/Housing/Interaction effect F3,32=18.62, P<0.0001) and preference for social novelty (FIG. 13F, MRD P<0.05, t=2.82; MHFD P=0.723, t=1.37; Co-housed MRD P<0.05, t=2.72; Cohoused MHFD P<0.01, t=3.34; Maternal diet/Housing/Interaction effect F3,32=4.55, P<0.01) as well as UniFrac phylogenetic clustering (FIG. 13G, P<0.001, R2=0.681; n=1,000 rarefactions; 12,600 reads/sample), are all restored in MHFD offspring co-housed with MRD mice in a 3 MHFD:1MRD configuration. Plots show mean±SEM.

FIGS. 14A-14G: Social Deficits of Germ Free (GF) Mice are Rescued by Fecal Microbiota Transplant from MRD, but not MHFD, Donors at 4 Weeks of Age, Related to FIGS. 3A-3L. FIGS. 14A-14B, During the reciprocal social interaction test, number of contacts (FIG. 14A, P<0.001, t=10.10) and frequency of interaction (FIG. 14B, P<0.001, t=10.19) were reduced in GF offspring. FIGS. 14C-14D, In the three chamber test, GF mice showed impaired sociability (FIG. 14C, Control P<0.01, t=3.87; GF P=0.95, t=0.73; Group effect F1,24=10.58, P<0.01) and preference for social novelty (FIG. 14D, Control P<0.05, t=2.54; GF P>0.99, t=0.30; Group effect F1,24=2.51, P=0.13). FIGS. 14E-14F, Results from the three-chamber test show fecal microbiota transplant from MRD, but not MHFD offspring at weaning (four weeks), restored both GF sociability (FIG. 14E, MRD-colonized GF P<0.01, t=3.39; MHFD-colonized GF P>0.99, t=0.67; Donor/Interaction option effect F1,28=8.25, P<0.01) and preference for social novelty (FIG. 14F, MRD-colonized GF P<0.05, t=2.89; MHFD-colonized GF P=0.69, t=0.96; Donor effect F1,28=7.42, P<0.05). FIGS. 14G-14H, At eight weeks, neither MRD- nor MHFD-fecal microbiota transplant improved the social deficits in GF mice (FIG. 14G, MRD-colonized GF P=0.55, t=1.15; MHFD-colonized GF P=0.41, t=1.35; Donor effect F1,12=0.020, P=0.89; FIG. 14H, MRD-colonized GF P=0.18, t=1.85; MHFD-colonized GF P>0.99, t=0.53; Donor effect F1,12=2.85, P=0.12). FMT=fecal microbiota transplant. Plots show mean±SEM.

FIGS. 15A-15E, Bacterial diversity in GF MRD and MHFD recipients over time displayed as a local regression with 95% confidence interval (FIG. 15A). Compared to GF mice transplanted with MRD fecal matter, the number of OTUs observed in GF mice transplanted with MHFD fecal matter was similar at 24 h post-transplant (FIG. 15A, 15B, P=0.57, t=0.61), but was reduced at one (FIGS. 15A, 15C, P<0.05, t=3.27), two (FIGS. 15A, 15D, P<0.05, t=3.12), and eight weeks (FIGS. 15A, 15E, P<0.05, t=0.298). FIG. 15F, The number of observed OTUs was reduced in GF mice that received fecal microbiota from MHFD versus MRD offspring (FIG. 15F, P<0.05, t=2.98). Plots show mean±SEM.

FIG. 16A-16C: *L. reuteri* Treatment Reverses MHFD Social Deficits, Related to FIGS. 4A-4P and Table 1. All MRD offspring groups preferred the chamber containing a mouse in the sociability test (FIG. 16A, MRD+media P<0.05, t=2.84; MRD+heat-killed *L. reuteri*, P<0.001, t=4.12; MRD+live *L. reuteri* P<0.0001, t=5.71) and the chamber containing Mouse 2 in the social novelty test (FIG. 16B, MRD+media P<0.01, t=3.90; MRD+heat-killed *L. reuteri*, P<0.001, t=4.44; MRD+live *L. reuteri* P<0.01, t=3.57). Unlike media alone (FIG. 16A, MHFD+media P>0.99, t=0.56; FIG. 16B, MHFD+media P>0.99, t=0.64) or heat-killed *L. reuteri* (FIG. 16A, MHFD+Heat-killed *L. reuteri* P=0.085, t=2.50; FIG. 16B, MHFD+Heat-killed *L. reuteri* P>0.99, t=0.053), administration of live *L. reuteri* in the drinking water improved MHFD offspring sociability and preference social novelty (FIG. 16A, MHFD+*L. reuteri* P<0.0001, t=5.06; Treatment effect F1, 86=55.61, P<0.0001; FIG. 16B, MHFD+*L. reuteri* P<0.001, t=4.55; Treatment effect F1, 86=37.12, P<0.0001). FIG. 16C, Pre- and post-treatment plating revealed that most of *L. reuteri* survived over the 24 h treatment period but none did after the heat-killing procedure. Plots show mean±SEM.

FIGS. 17A-17G: Treatment with another *Lactobacillus*, (*L.*) *johnsonii*, Failed to Reverse Social Deficits in MHFD Offspring, Related to FIGS. 4A-4P and FIG. 7. FIG. 17A, Schematic of *L. johnsonii* treatment. FIGS. 17B,17C, Neither resuspension media (FIG. 17B, P=0.38, t=1.72; FIG. 17C, P>0.99, t=0.40) nor *L. johnsonii* administration in the drinking water (FIG. 17B, P>0.99, t=0.78; FIG. 17C, P>0.99, t=0.21) improved sociability (FIG. 17B) or preference for social novelty (FIG. 17C) in MHFD offspring (FIG. 17B, Treatment effect F3, 32=23.94, P<0.0001; FIG. 17C, Treatment effect F3, 32=6.13, P<0.001). FIGS. 17D-17G, Representative track plots of mice during each stage of the 3-chamber task, cohorts as noted. Plots show mean±SEM.

FIGS. 18A-18B: Exaggerated Repetitive Behavior in MHFD and Germ Free (GF) mice is not Mediated by Changes in the Microbiome, Related to FIGS. 4A-4P. FIG. 18A, Schematic of the marble-burying task, a measure of repetitive behavior in mice. FIG. 18B, MHFD offspring buried more marbles than MRD offspring (P<0.05, t=3.64). More marbles were buried by GF mice compared to conventionally colonized MRD offspring (P<0.0001, t=5.20). Co-housing failed to reverse the increased marble-burying behavior in MHFD offspring (Co-housed MHFD vs. MRD, P<0.01, t=4.32; Co-housed MHFD vs. MHFD, P>0.99, t=1.51) and colonization of GF mice with MRD microbiota at 4 weeks of age did not reverse the exaggerated repetitive behavior (MRD-colonized GF vs. MRD, P=0.25, t=2.60; MRD-colonized vs. GF, P>0.99, t=1.38). Plot shows mean±SEM.

FIGS. 19A-19F: *L. reuteri*-treatment Failed to Reverse the Anxiety-related behavior of MHFD Offspring, Related to FIGS. 4A-4P. FIG. 19A, Schematic of the open field test. FIG. 19B, Compared to MRD, MHFD offspring spent less time exploring the center of the open field arena (P<0.05, t=3.61) and *L. reuteri* treatment did not significantly affect this behavior (MHFD vs. MHFD+*L. reuteri*, P>0.99, t=0.13; MRD vs. MHFD+*L. reuteri*, P<0.05, t=2.79; F2, 49=7.82, P<0.01). FIG. 19C, Representative plots of exploratory activity. FIGS. 19D-19F, Measures of locomotor activity during arena exploration did not differ between maternal diet or treatment groups (FIG. 19D, F2, 49=0.26, P=0.77; 19E, F2, 49=0.25, P=0.78; 19F, F2, 49=1.30, P=0.28). Plots show mean±SEM.

FIGS. 20A-20C: Identification of DA Neurons in the Lateral VTA in Midbrain Slices from Mice, Related to FIGS. 5A-5L and 6A-6F. FIG. 20A, Representative recording from a neuron in the lateral VTA showing stable pacemaker firing at 1-5 Hz in cell-attached mode. FIG. 20B, Spike width was measured from the start of the inward deflection to the outward peak at a holding potential of −55 mV. Neurons displaying spike widths >1.0 ms were taken as dopaminergic. FIG. 20C, Only ventrolateral VTA neurons were studied with a large (>150 pA) hyperpolarization-activated current (Ih) and a large (>150 pA) leak current.

FIG. 21A, Evoked EPSC (eEPSC) amplitude as a function of stimulation intensity is plotted as input/output curves (recorded in voltage clamp at −70 mV with cesium-containing pipettes and in the presence of 100 µM picrotoxin) was similar in VTA slices from MRD and MHFD offspring (t=0.16, p=0.88, n=5). FIG. 21B, Paired EPSC were recorded at 50, 100, 200 and 400 ms inter-timulus intervals and paired-pulse ratios of EPSC2/EPSC1 show no difference between MRD and MHFD offspring (t=0.2, p=0.84, n=5). FIGS. 21C-21E, Sample traces (top) of miniature spontaneous EPSCs and summary data (bottom) show similar frequency (FIG. 21D, t=0.24, p=0.81, n=6) and amplitude (FIG. 21E, t=0.07, p=0.94, n=6) in VTA slices from MRD and MHFD offspring. Plots show mean±SEM.

FIGS. 22A-22D: Oxytocin Administration Improves MHFD Offspring Social Behavior, Related to FIGS. 6A-6F. FIGS. 22A-22B, In the reciprocal social interaction test, intranasal oxytocin administration improved MHFD offspring contact duration (FIG. 22A, P=0.052, t=2.99; Treatment effect F2, 8=5.87, P<0.05) and interaction frequency (FIG. 22B, P<0.05, t=3.43; Treatment effect F2, 8=14.58, P<0.01), whereas intranasal vehicle administration alone had no effect (FIG. 22A, P>0.99, t=0.11; 22B, P=0.20, t=2.11). FIGS. 22C-22D, In the three-chamber task, intranasal oxytocin improved sociability (FIG. 22C, MHFD+Vehicle P>0.99, t=0.29; MHFD+Oxytocin P<0.01, t=3.50; Treatment effect F1, 12=5.16, P<0.05) and preference for social novelty (FIG. 22D, MHFD+Vehicle P=0.50, t=1.25; MHFD+Oxytocin P=0.096, t=2.34; Treatment effect F(1,8)=6.41, P<0.05) in MHFD offspring. Plots show mean±SEM.

FIGS. 24A-24D: Treatment with *L. reuteri* rescues social behavioral Cntnap2-deficient mice. (FIGS. 24A-24B) Mice lacking Cntnap2 showed impaired sociability and social novelty. (FIGS. 24C-24D) Addition of *L. Reuteri* into the drinking water reverses the deficient sociability (FIG. 24C) and social novelty (FIG. 24D) in mice lacking Cntnap2.

DETAILED DESCRIPTION

Figure 1A:
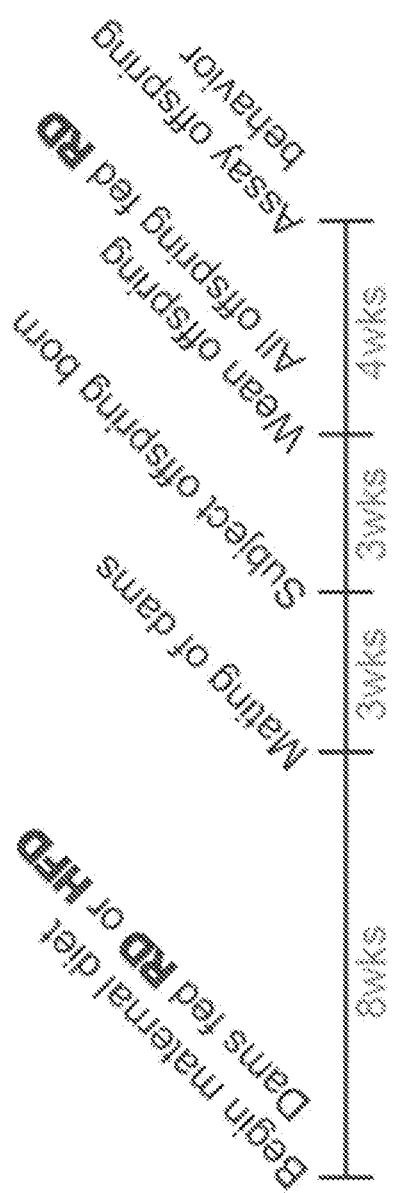
Figure 1H:
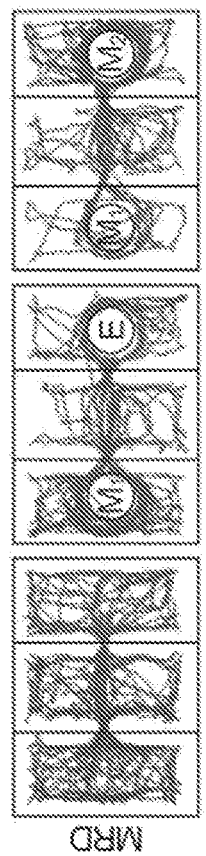
Figure 1I:
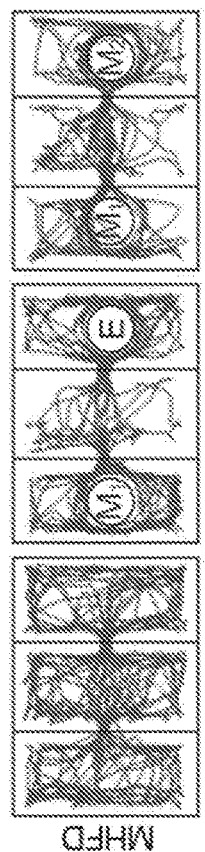

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the invention may "consist essentially of" or "consist of" one or more elements of the invention, for example. Some embodiments of the invention may consist of or consist essentially of one or more elements, method steps, and/or methods of the invention. It is contemplated that any method or composition described herein can be implemented with respect to any other method or composition described herein. Embodiments discussed in the context of methods and/or compositions of the invention may be employed with respect to any other method or composition described herein. Thus, an embodiment pertaining to one method or composition may be applied to other methods and compositions of the invention as well. The scope of the present application is not intended to be limited to the particular embodiments of the process, machine, manufacture, composition of matter, means, methods and steps described in the specification.

Embodiments of the disclosure concern methods and compositions for treating or preventing social behavior deficiencies or medical conditions wherein one or more social behavior deficiencies are at least one symptom. In some cases the individual has a neurodevelopmental disorder. In particular cases, an individual in need thereof is provided an effective amount of one or more particular bacteria for a therapeutic or preventative purpose, and in some cases the individual has autism spectrum disorder (ASD), for example.

I. Probiotics and Formulations

Embodiments of the disclosure provide for treatment or prevention of a medical condition in which at least one symptom is a social behavioral deficiency, including in some cases a neurodevelopmental disorder. In particular embodiments an individual that has a social behavioral deficiency or that is at risk for having a social behavioral deficiency, or an individual that is pregnant with an individual that is at risk for having a social behavioral deficiency, is provided an effective amount of a formulation comprising an effective amount of *Lactobacillus*, such as *L. reuteri*. Any strain of *L. reuteri* may be utilized. Examples of strains of *L. reuteri* include at least ATCC PTA 6475, DSM17938, ATCC PTA4659, ATCC PTA 5289, ATCC 55730, CRL1324, DSM20016, CF4-6G, ATCC55730, CF48-3A1, M27U15, and other strains listed in Frese et al., 2011; Spinler et al., 2014; Oh et al., 2010, and combinations thereof. The *L. reuteri* may be obtained from any suitable source, including commercially, from a research laboratory, as a gift, or isolated from nature. Isolation methods for *L. reuteri* are known in the art, including at least those described in U.S. Pat. Nos. 5,439,678 and 5,849,289 (both incorporated by reference herein in their entirety), for example.

Compositions comprising the bacteria selected using the methods described above are provided. The compositions may include a pharmaceutically acceptable carrier, diluent and/or excipient, in some cases. The composition may include more than one bacterial isolate. The compositions may be formulated for delivery in food, water, via oral gavage, via an aerosol or sprayable product, drops, powder freeze-dried, extract, pill and/or via suppository, in specific cases.

The strains or compositions encompassed herein may be administered in a variety of ways known or available to those skilled in the art. The strains or compositions may be administered in the form of a pharmaceutical, nutraceutical, added to food and/or water, and/or provided in aerosolized or sprayable form for administration by inhalation. In addition, the strains and compositions described herein may be provided as liquid suspensions, lyophilized or freeze dried powders or frozen concentrates for addition to target regions other than a subject, as examples.

In specific embodiments, the *L. reuteri* composition and related methods of the present disclosure utilize particular formulation methods. In some examples, the carrier may further comprise a disintegrant, a glidant, and/or a lubricant, such as is described in U.S. Pat. No. 9,084,434, for example, to facilitate having a greater shelf life and/or half-life of the formulation. The disintegrant may be any suitable disintegrant such as, for example, a disintegrant selected from the group consisting of sodium croscarmellose, crospovidone, gellan gum, hydroxypropyl cellulose, starch, and sodium starch glycolate. The glidant may be any suitable glidant such as for example, a glidant selected from the group consisting of silicon dioxide, colloidal silicon dioxide, and talc. The lubricant may be any suitable lubricant such as for example, a lubricant selected from the group consisting of calcium stearate, magnesium stearate, stearic acid, sodium stearyl fumerate, and vegetable based fatty acids. In the composition and method of the present invention, the carrier, is present in the composition in a range of approximately 30% w/w to approximately 98% w/w; this weight percentage is a cumulative weight percentage taking into consideration all ingredients present in the carrier. The composition of the present invention may be an oral dosage form, a powder that is mixed into a liquid, or a chewing gum. Where the composition is an oral dosage form, the oral dosage form may be selected from the group consisting of tablets, caplets, and capsules, wherein the tablets and caplets may be solid or chewable. Where the composition is a powder, it may be mixed into a liquid that is selected from the group consisting of water, milk, juice, and yogurt. Where the composition is a chewing gum, the gum may be soft gum or hard chewing gum tablets. By combining probiotic species with sugar alcohols, such as mannitol, sorbitol, alone or together with the additional sugar alcohol lactitol and/or a phytonutrient, such as oligomeric proanthocyanidins (OPC), the stability of probiotic formulations is increased under various storage conditions.

In particular aspects, the probiotic compositions of the present disclosure may be prepared as a powder that is intended to be dissolved in a liquid, such as water, milk, juice, and yogurt. It is understood that individual liquids may be mixed together where appropriate. For example, the probiotic formulation may be combined with fruit juice and yogurt or milk and yogurt to make probiotic yogurt shakes. The probiotic formulation may also be combined with milk and ice cream to make probiotic milk shakes. Flavorings for the probiotic liquid formulations contemplated in the disclosure are known to those of ordinary skill in the art.

In particular cases the *L. reuteri* formulation (as an example of *Lactobacillus*) comprises one or more excipients. Examples of excipients that may be used to formulate appropriate dosage forms include binders, disintegrants, lubricants, coatings, plasticizers, compression agents, wet granulation agents, and sweeteners, all of which are known to those of ordinary skill in the art to which the invention pertains. All of the following examples are provided by way of illustration and not limitation. Binders are used where appropriate to help the dosage form ingredients still together. Examples of binders include carbopol, povidone, and xanthan gum. Lubricants are generally always used in the manufacture of dosage forms by direct compression in order to prevent the compacted powder mass from sticking to the equipment during the tabletting or encapsulation process. Examples of lubricants include calcium stearate, magnesium stearate, stearic acid, sodium stearyl fumerate, and vegetable based fatty acids. Disintegrants aid in the break-up of the compacted mass when placed in a fluid environment. Examples of disintegrants include sodium croscarmellose, crospovidone, gellan gum, hydroxypropyl cellulose, starch, and sodium starch glycolate. Coatings are used to control the solubility of the drug. Examples of coatings include carrageenan, cellulose acetate phthalate, ethylcelulose, gellan gum, matodextrin, methacrylates, methylcellulose, microcrystalline cellulose, and shellac. Plasticizers are used to control the release rate of the drug from the dosage form. Examples of plasticizers include citrate esters, dibutyl sebacate, diethyl phthalate, polyvinylacetate phthalate, and triacetin. Compression agents include calcium carbonate, dextrose, fructose, guar gum, honey, lactose, maltodextrin, maltose, mannitol, microcrystalline cellulose, molasses, sorbitol, starch, and sucrose. Wet granulation agents include calcium carbonate, lactose, maltodextrin, mannitol, microcrystalline cellulose, povidone, and starch. Sweeteners include aspartame, dextrose, fructose, honey, lactose, maltodextrin, maltose, mannitol, molasses, monoammonium glycyrrhizinate, sorbitol, sucralose, and sucrose. Excipients that are generally used in the manufacture of chewable tablets include by way of illustration and not limitation, dextrose, fructose, guar gum, lactose, maltodextrin, maltose, mannitol, microcrystalline cellulose, and sorbitol. As is evident from the foregoing list, many of the same ingredients may be used for various different purposes in various different dosage forms.

A *L. reuteri* composition may be provided as a formulation to the individual in any suitable form, and in particular embodiments they are live although in certain embodiments they are dead. In particular cases, the *L. reuteri* formulation is formulated to target a region in the gastrointestinal tract, including any portion of the gastrointestinal tract. The *L. reuteri* formulation is formulated to be delivered to any portion of the gastrointestinal tract.

The formulation may be provided in food and/or beverage, in specific embodiments. Particular examples include dairy products and/or probiotic-fortified foods. However, tablets, capsules, gums, or powders containing the bacteria in freeze-dried form are also available. In specific embodiments, the *L. reuteri* is provided in a pill or in yogurt, for example. The formulation may be provided in infant formula and/or cereal (infant or otherwise), in some cases.

In particular embodiments, each dose of the *L. reuteri* composition may comprise a certain range of bacterial cells. In specific cases, the *L. reuteri* composition comprises a range of about $10^3$ cells to about $10^{13}$ cells. In certain cases, each dose is in the range of about $10^5$ cells to about $10^{11}$ cells, about $10^5$ to about $10^{10}$ cells, about $10^7$ cells to about $10^{10}$ cells, and so forth. In other cases, each dose is in the range of about 10 cells to about $10^1$ cells.

In some cases, the probiotic microorganisms are preferably not freeze- or spray-dried in a ready-to-use product, because the microorganisms preferably should be as robust as possible when entering the intestines in order to successfully compete with the pro-inflammatory part of the microflora already present in the intestines. However, some strains may be sufficiently robust and/or some protocols sufficiently gentle to allow spray- or freeze-dried probiotic microorganisms in a ready-to-use product.

Embodiments of the disclosure include one or more formulations that comprise a *L. reuteri* strain suitable for delivery to an individual in need thereof. In some cases, the formulation further comprises a prebiotic material, which is a food ingredient that promotes the growth of the *L. reuteri*, such as simple sugars, complex carbohydrates, fibers, fats, proteins or natural products, such as viatmains, minerals and polyphynols that stimulate the survival, growth or activity of *L. reuteri* or promote its persitance in the gastrointestinal track. In some cases, the formulation comprises an ingestible carrier, which may be a pharmaceutically acceptable carrier such as a capsule, tablet or powder. In specific embodiments, the ingestible carrier is a food product such as acidified milk, yogurt (frozen or non-frozen), milk powder, milk concentrate, cheese spreads, dressings and/or beverages. In some cases, the formulation further comprises a protein and/or peptide, in particular proteins and/or peptides that are rich in glutamine/glutamate, a lipid, a carbohydrate, a vitamin, mineral and/or trace element, for example. the formulation may further comprise an adjuvant, a drug, a biological compound, or a mixture thereof. The formulation may be a food stuff or a medicament, in certain embodiments.

An effective amount of *L. reuteri* may be provided to an individual in need thereof and may or may not be provided with one or more additional probiotics, such as one or more additional probiotic bacteria and/or yeast. The additional probiotic bacteria and/or yeast may be in the same composition as the *L. reuteri*, or the additional probiotic bacteria and/or yeast may be in a different composition as the *L. reuteri*. The additional probiotic bacteria and/or yeast may or may not be given to the individual at the same time as the *L. reuteri*. The additional probiotic bacteria and/or yeast may assist in treating and/or preventing at least one social behavioral deficiency and/or the additional probiotic bacteria may be useful for treating and/or preventing at least one symptom of another medical condition. Other medical conditions that may be treated and/or prevented at the same time with other probiotics include at least anxiety, cognition, schizophrenia, bipolar disorder, mood disorder, seasonal affective disorder, irritable bowel syndrome, inflammatory bowel disease (IBD), infectious diarrhea (caused by viruses, bacteria, or parasites), antibiotic-related diarrhea, skin conditions (such as eczema), urinary and vaginal health, preventing allergies and colds, and oral health.

The additional probiotic bacteria and/or yeast may be of any kind, so long as it is not pathogenic in the amount provided to the individual. In specific embodiments, the additional probiotic bacteria and/or yeast may be *Lactobacillus acidophilus, L. bulgaricus, L. casei, L. fermentum, L. paracasei, L. plantarum, L. rhamnosus, L. salivarius, Bifidobacterium bifidum, B. infantis, B. animalis* subsp. *lactis, B. longum, Streptococcus thermophilis, Enterococcus faecalis, E. faecium, Bifidobacterium, Saccharomyces boulardii*, and *Lactobacillus bifidus, Parabacteroides distasonis, Helicobacter hepaticus, Bacteroides uniformis, Olsenella* unclassified, *Collinsella* unclassified, *Bifidobacterium pseudolongum, Lactobacillus johnsonii*, or a combination thereof. In cases wherein one or more other bacteria and/or yeast are provided to an individual, they may be provided in a particular ratio. In cases where there is one other bacteria in the formulation, such a ratio may be 1:1, 1:2, 1:5, 1:10, 1:25, 1:50, and so forth. In cases where there is more than one other bacteria in the formulation, the particular ratio may be 1:1:1; 1:2:1; 1:10:1; 1:2:2; 1:10:10; 1:100:1; 1:100:100, and so forth.

The individual may also be ingesting vitamins and/or fish oil, for example.

II. Treatment and Delivery Embodiments

In particular embodiments, an individual that is the subject for methods and compositions of the disclosure has a medical condition in which at least one symptom is a social behavior deficiency. In specific embodiments, the individual has a neurodevelopmental disorder, and such a disorder may have any cause, including deprivation, genetic and metabolic diseases, immune disorders, infectious diseases, nutritional factors, physical trauma, and toxic and environmental factors, for example; the disorder may have two or more causes. In specific embodiments, a treatment regimen is for an individual with ASD. In any case, the individual may have been born from a mother on a high-fat diet, a mother that was obese, or a mother that was overweight, or the individual may be pregnant.

An individual having a social behavior deficiency is provided an effective amount of a formulation comprising at least an effective amount of *L. reuteri*. In some cases, there may be a regimen having a first phase for an initial treatment, which may last for days, weeks, months, or years, and then another phase for maintenance, which may last for weeks, months, or years. In a particular form of the disclosure, an initial treatment regimen may comprise of at least about $10^5$, $10^6$, $10^7$, $10^8$, $10^9$, or $10^{10}$ cells per dose. Such a treatment may be administered one or more times a day, including about 1, 2, 3, or more times per day, for a period sufficient to stabilize the gut flora. In other cases, in a maintenance phase, an individual is provided a lesser amount of the bacteria and/or fewer administrations than the initial treatment phase.

The duration of a treatment regimen may be dependent on each individual patient and the stage of the medical condition. In some cases, a continued treatment for a certain period of time occurs until a detectable improvement in a social behavior deficiency. In some cases, the improved social behavior deficiency is maintained by additional treatment, although the additional treatment may be reduced in frequency and/or volume.

Although in some cases, the *L. reuteri* formulation is provided to an infant or child having a social behavior deficiency, in some cases the infant or child is given the *L. reuteri* formulation when there is no detected social behavior deficiency but the infant or child had a biological mother that was obese or was overweight and/or that had a high fat diet. In some cases the biological mother that is obese or overweight or that is on a high fat diet is given the formulation before birth of the infant. In certain cases an individual that is an adolescent or adult is given suitable doses of *L. reuteri* to improve a social behavior deficiency, and that individual may or may not have had a mother that was obese, overweight, or on a high-fat diet. In other cases, *L. reuteri* formulation is provided to infants, children, adolescent, adults and/or the elderly.

In cases wherein a mother of an individual with a social behavior deficiency is obese, the mother and/or the child may be treated (the mother prior to birth). A mother is considered obese of she has a body mass index (BMI) of 30 or greater. A mother is considered overweight if she has a BMI of 25 to 29.9.

One of skill in the art may measure one or more social behavior deficiencies in humans in a variety of ways. In specific embodiments, the skilled artisan would employ the standards set forth in the Diagnostic and Statistical Manual of Mental Disorders, Fifth Edition (DSM-5):

A. Persistent difficulties in the social use of verbal and nonverbal communication as manifested by all of the following:
1. Deficits in using communication for social purposes, such as greeting and sharing information, in a manner that is appropriate for the social context.
2. Impairment of the ability to change communication to match context or the needs of the listener, such as speaking differently in a classroom than on the playground, talking differently to a child than to an adult, and avoiding use of overly formal language.
3. Difficulties following rules for conversation and storytelling, such as taking turns in conversation, rephrasing when misunderstood, and knowing how to use verbal and nonverbal signals to regulate interaction.
4. Difficulties understanding what is not explicitly stated (e.g., making inferences) and nonliteral or ambiguous meanings of language (e.g., idioms, humor, metaphors, multiple meanings that depend on the context for interpretation).

B. The deficits result in functional limitations in effective communication, social participation, social relationships, academic achievement, or occupational performance, individually or in combination.

C. The onset of the symptoms is in the early developmental period (but deficits may not become fully manifest until social communication demands exceed limited capacities).

D. The symptoms are not attributable to another medical or neurological condition or to low abilities in the domains or word structure and grammar, and are not better explained by autism spectrum disorder, intellectual disability (intellectual developmental disorder), global developmental delay, or another mental disorder.

E. Persistent deficits in social communication and social interaction across multiple contexts, as manifested by the following, currently or by history (examples are illustrative, not exhaustive, see text):
1. Deficits in social-emotional reciprocity, ranging, for example, from abnormal social approach and failure of normal back-and-forth conversation; to reduced sharing of interests, emotions, or affect; to failure to initiate or respond to social interactions.
2. Deficits in nonverbal communicative behaviors used for social interaction, ranging, for example, from poorly integrated verbal and nonverbal communication; to abnormalities in eye contact and body language or deficits in understanding and use of gestures; to a total lack of facial expressions and nonverbal communication.
3. Deficits in developing, maintaining, and understanding relationships, ranging, for example, from difficulties adjusting behavior to suit various social contexts; to difficulties in sharing imaginative play or in making friends; to absence of interest in peers.
4. Symptoms cause clinically significant impairment in social, occupational, or other important areas of current functioning.

In particular embodiments, an individual in need thereof is provided an effective amount of *L. reuteri* for the purpose of improving a social behavior deficiency. In some cases, an individual is intentionally provided an effective amount of *L. reuteri* for the purpose of improving at least one social behavior deficiency. A pregnant mother may be provided an effective amount of *L. reuteri* for the purpose of preventing or improving at least one social behavior deficiency in her offspring, and in some cases that mother is obese, overweight, or has a high fat diet. In some methods, a pregnant woman is identified as being in need of an effective amount of *L. reuteri* because she is obese, overweight, and/or on a high fat diet, although in some cases she is not. An individual may be at risk of having at least one social behavior deficiency because their biological mother was obese, overweight, and/or on a high fat diet, and the identification of such a risk is a part of some methods. In other cases, *L. reuteri* may be administered to increase social bonding, improve mood, reduce depression and increase well being in individuals, including friends, family members, colleagues and partners.

In certain embodiments, at least one symptom of at least one neurodevelopmental disorder is treated with an effective amount of *L. reuteri*. An individual may be treated for social deficits and changes in gut microbiome by providing the pregnant mother or the offspring an effective amount of a *L. reuteri* formulation. In some cases, the effective amount of the *L. reuteri* formulation indirectly or directly improves social interaction because it indirectly or directly induces synaptic potentiation (LTP) in the ventral tegmental area (VTA) of the individual. In some cases, the effective amount of the *L. reuteri* formulation indirectly or directly increases the number of oxytocin immunoreactive neurons in the hypothalamus. Embodiments of the disclosure impact the consequences of maternal diet, gut microbiota dysbiosis, VTA plasticity and abnormal social behavior by providing an effective *L. reuteri* probiotic therapy for an individual.

In specific embodiments, an individual is provided a therapy or preventative for one or more social behavior deficiencies in addition to the compositions encompassed herein. For example, they may be provided the following in addition to *L. reuteri*: a) other bacteria species, b) prebiotic and other nutrients (e.g., vitamins, lipids, proteins, etc.) with *L. reuteri* and c) behavioral therapy in combination with *L. reuteri*.

In specific cases, *L. reuteri* is not delivered as a live microorganism, but instead a specific extract or fraction produced from the live microorganism may be equally bioactive. This has been demonstrated, for example, in the case of wound healing in animals, in which consumed sonicated mixtures or lysates prepared from live or dead *L. reuteri* are biologically active in a wound healing model (Poutahidis et al., 2013; Varian et al., 2016). The mixtures, lysates or extracts may be delivered in pill form or any other standard delivery mode (food or liquid beverages, yogurt, dry powder mixed in water or beverage in which such mixtures can be effectively dosed and consumed in a biologically active format.

III. Kits of the Disclosure

Kits are also included as part of the disclosure. Kits for implementing methods of the invention described herein are specifically contemplated. In some embodiments, there are kits for treating social behavioral deficiencies in an individual and/or preventing onset of at least one symptom of social behavioral deficiencies in an individual. The kit may be provided for treatment and/or prevention of a social behavior deficiency in an individual, and in some cases wherein the mother of the individual is obese, overweight and/or on a high-fat diet. In some cases the kit is for a pregnant mother that is obese, overweight and/or on a high-fat diet, although in other cases the kit is for any pregnant mother or any infant, child, adolescent, or adult.

The container means of the kits will generally include at least one vial, test tube, flask, bottle, syringe or other container means, into which a *Lactobacillis* component (including *L. reuteri*) may be placed, and preferably, suitably aliquoted. Where there is more than one component in the kit other than a *Lactobacillis* component (including *L. reuteri*), the kit also will generally contain a second, third or other additional container into which the additional components (such as another bacteria) may be separately placed. However, various combinations of components may be comprised in a vial. The kits of the present disclosure also will typically include a means for containing the compositions, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the components of the kit may be provided as a stab or as a dried powder(s). When reagents and/or components are provided as a dry powder, the powder can be reconstituted by the addition of a suitable solvent. It is envisioned that the solvent may also be provided in another container means. The components of the kits may be packaged either in aqueous media or in lyophilized form.

A kit will also include instructions for employing the kit components as well the use of any other reagent not included in the kit. Instructions may include variations that can be implemented.

In some embodiments of the invention, other treatments for social behavioral deficiencies are included in the kit. Other treatments can involve behavioral treatments, medicines or both. When the individual has one of some neurodevelopmental disorders, the individual may have additional medical conditions such as sleep disturbance, seizures and/or gastrointestinal (GI) distress, and the kits may also have these therapeutic compositions.

EXAMPLES

The following examples are included to demonstrate some embodiments of the invention. It should be appreciated by those of skill in the art that the techniques disclosed in the examples which follow represent techniques discovered by the inventor to function well in the practice of the invention, and thus can be considered to constitute some modes for its practice. However, those of skill in the art should, in light of the present disclosure, appreciate that many changes can be made in the specific embodiments which are disclosed and still obtain a like or similar result without departing from the spirit and scope of the invention.

In particular embodiments, the findings of the disclosure link dysfunction of the gut and of the brain. Herein it is described that maternal high fat diet (MHFD) induces a shift in microbial ecology that has a direct negative impact on social behavior. Notably, it was found that MHFD-induced changes in the offspring gut microbiome blocks long-lasting neural adaptation in the mesolimbic dopamine reward system (ventral tegmental area, VTA). Of even broader interest and considerable impact is the identification of a probiotic candidate (a single bacterial species, in at least some cases) that reverses synaptic function in the VTA, social behaviors, as well as the levels of oxytocin, "the social hormone" (Donaldson and Young, 2008; Insel, 2010), in the brain of MHFD offspring.

Example 1

Social Behaviors are Impaired in MHFD Offspring. To investigate how maternal diet-induced obesity affects offspring neurodevelopment, female mice were fed either regular diet (RD) or high fat diet (HFD) for 8 weeks, a standard period required to reach a state of diet-induced obesity in mice (Aye et al., 2015). Females were then paired with males to produce offspring that were given regular diet after weaning (FIG. 1A). As expected, MHFD significantly increased maternal weight (FIGS. 8A-8C). Consistent with reports of more frequent spontaneous abortion in obese mothers (King, 2006), the litter size was reduced (FIG. 8D) and latency to first litter increased in female mice fed HFD (FIG. 8E). It is noteworthy that there was no significant difference in offspring weight between maternal diet cohorts at 7-12 weeks of age (FIGS. 8F and 8G), the time at which behavioral and electrophysiological experiments were performed.

Given that maternal obesity is associated with ASD (Bilder et al., 2013; Dodds et al., 2011; Krakowiak et al., 2012; Moss and Chugani, 2014) and deficient social interactions are a salient feature of ASD individuals (Mefford et al., 2012), social behavior in MRD and MHFD offspring was studied. First, reciprocal social interactions were assessed by recording the amount of time a pair of mice spent interacting in a neutral arena (FIG. 1B). When compared to MRD offspring, MHFD offspring had fewer reciprocal interactions (FIGS. 1C, 1D, 9A, and 9B). Next, the three-chamber test (Silverman et al., 2010) was used to assess a) sociability by comparing the time mice spent interacting with an empty wire cage versus one containing a mouse and b) preference for social novelty by measuring the time mice spent interacting with a familiar versus a stranger mouse (FIG. 1E). Consistent with the results from reciprocal social interactions, MHFD offspring had impaired sociability and showed no preference for social novelty (FIGS. 1F-1I, 9C, and 9D). Taken together these data indicate that MHFD offspring display social deficits.

Dysbiosis of the Gut Microbiota in MHFD Offspring.

Figure 1J:
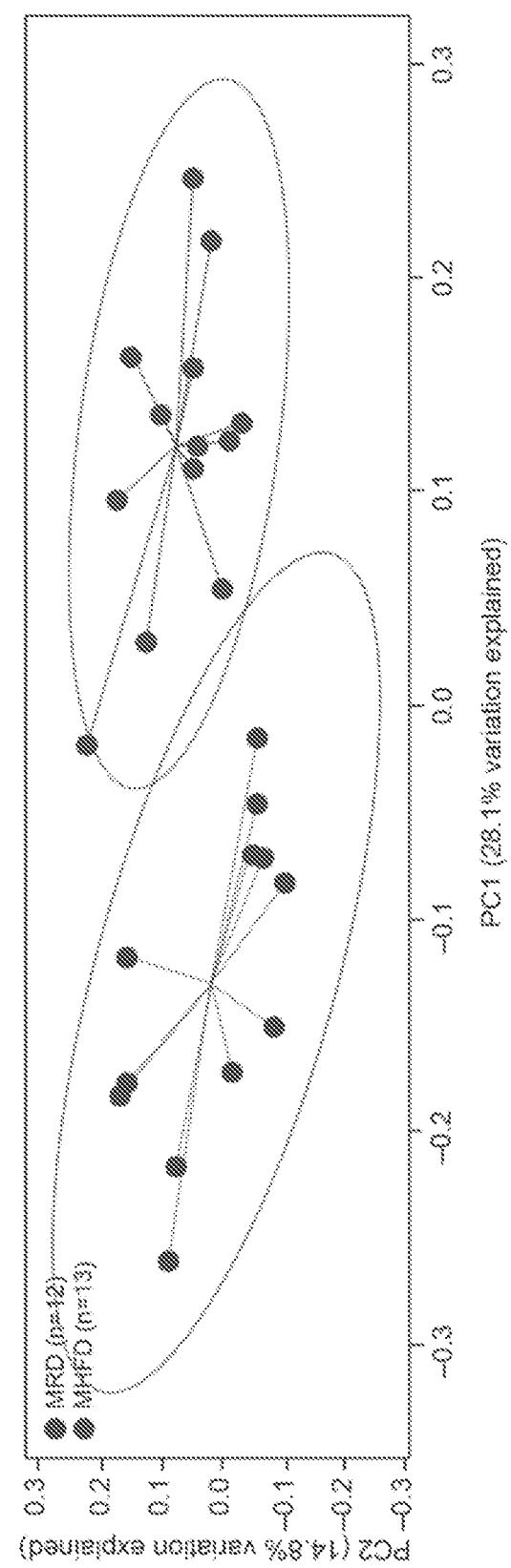
Figure 10B:
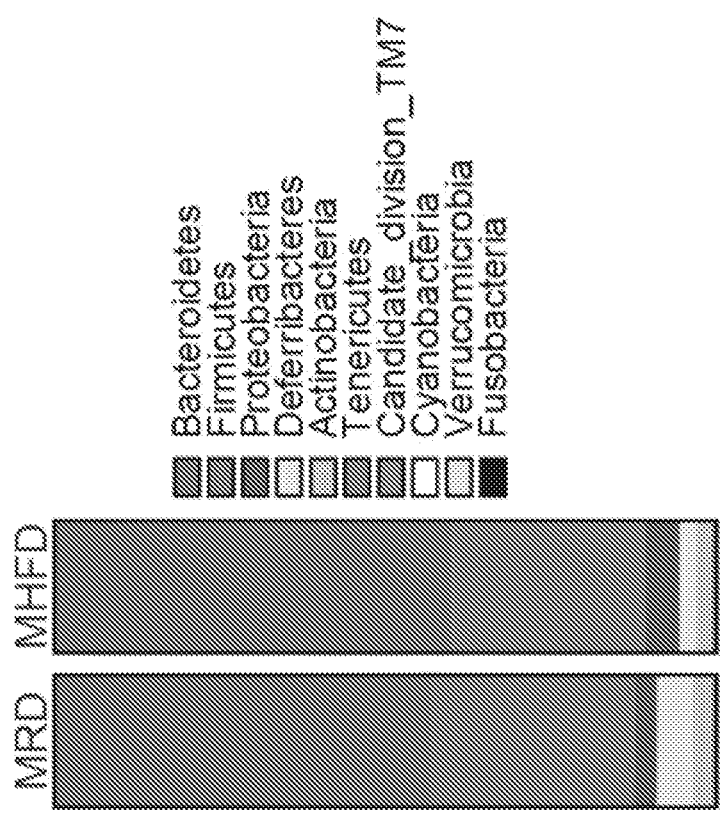
Figure 10D:
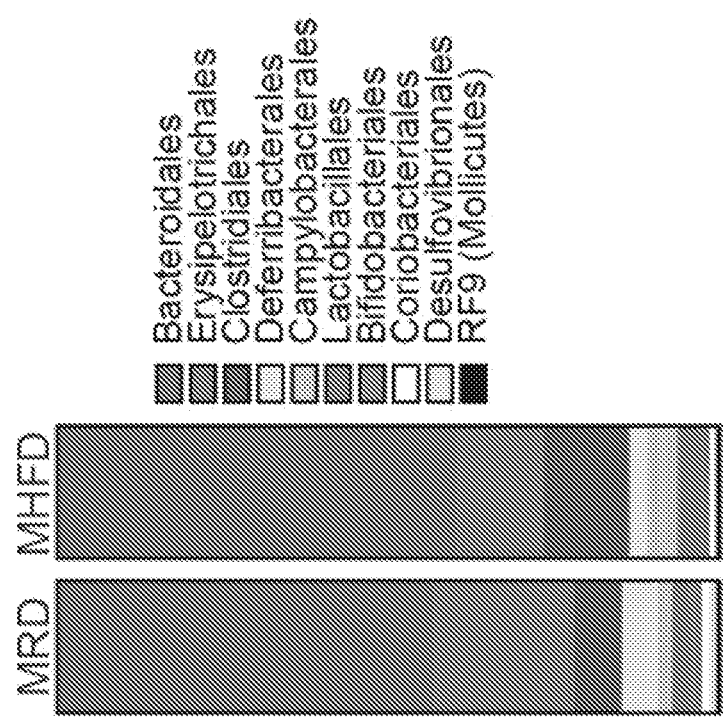
Figure 10E:
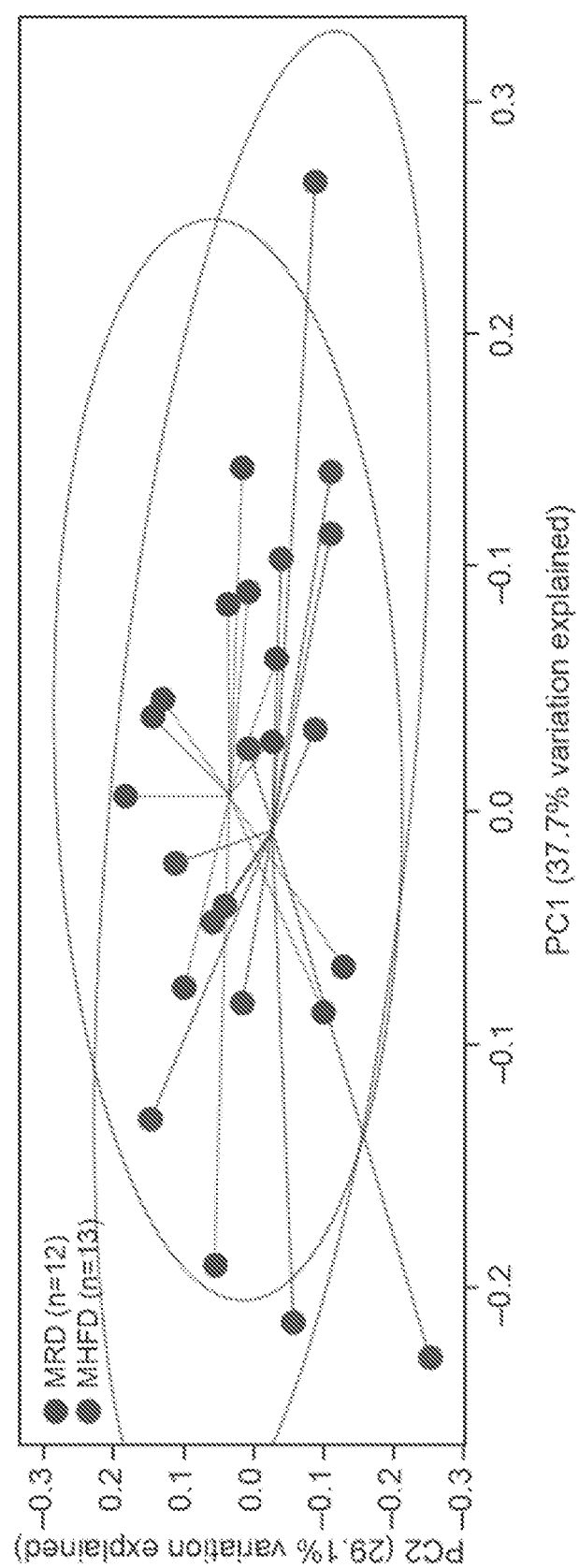
Figure 10F:
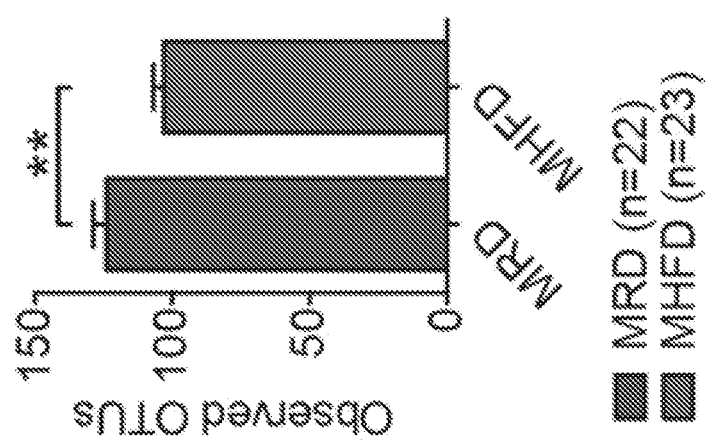
Figure 11A:
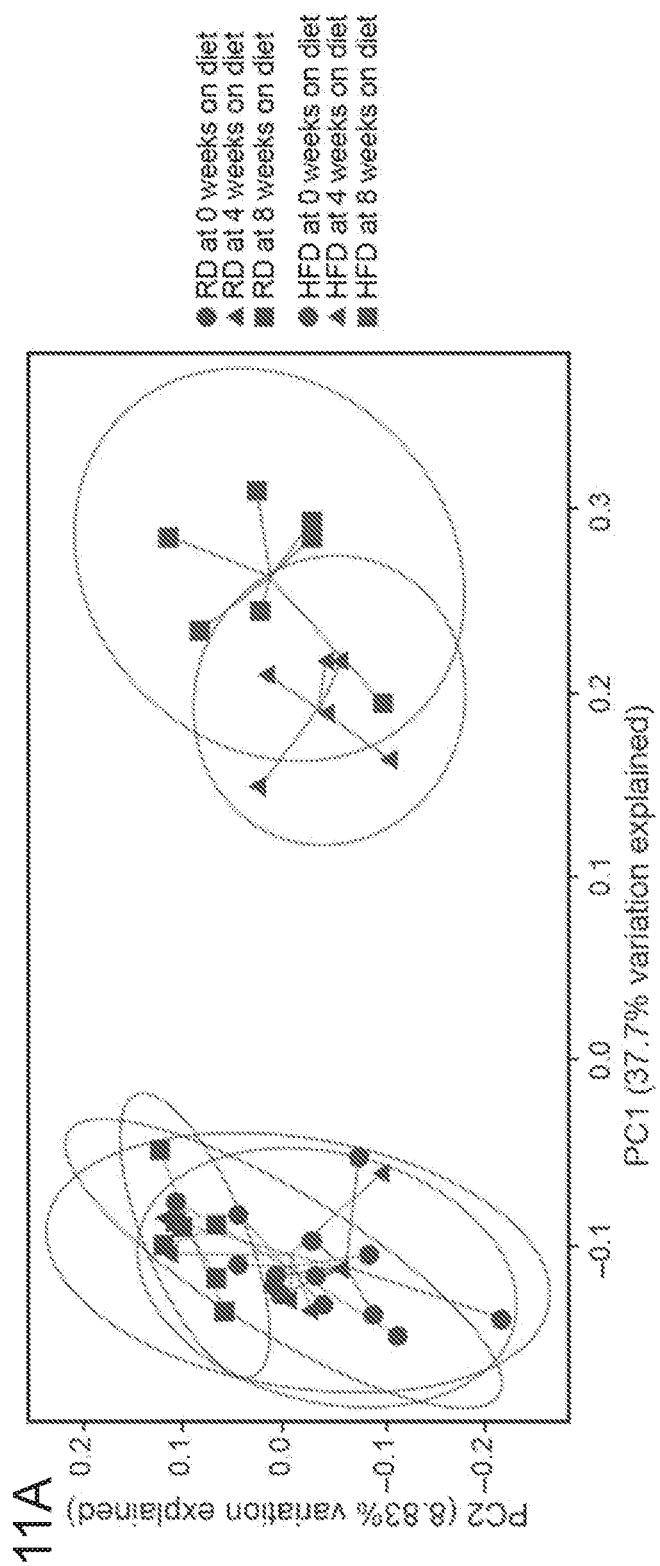
FIGS. 11A-11B: HFD Alters the Maternal Microbiome, Related to FIGS. 1A-1J.
Figure 11B:
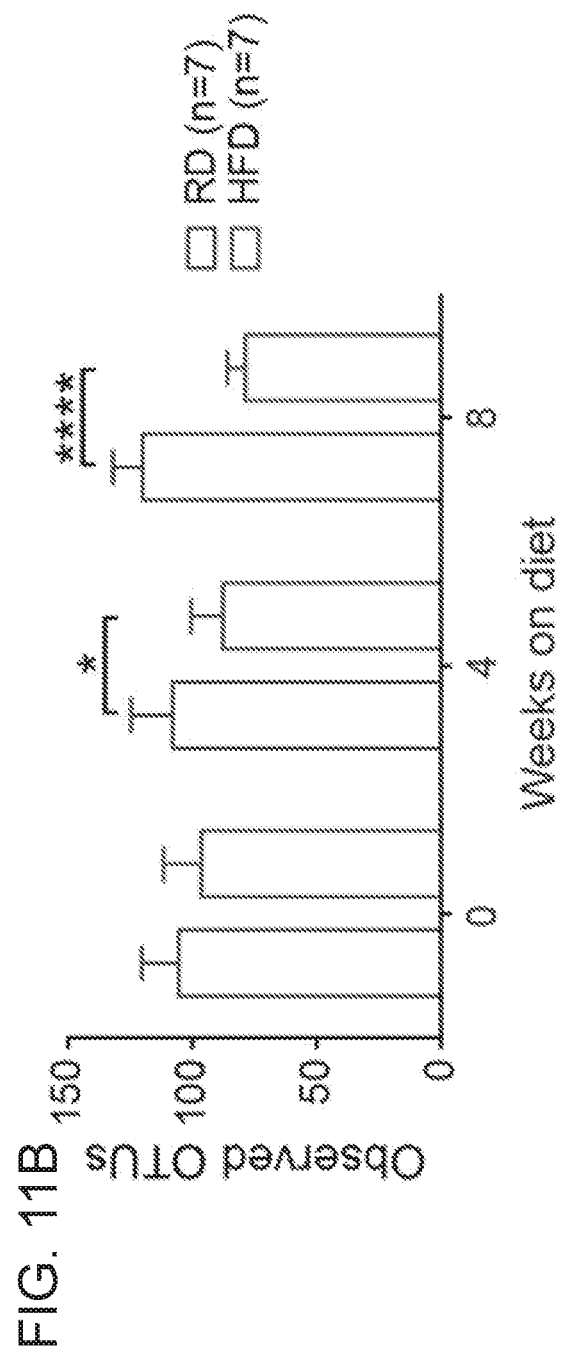
Figures 12A, 12B:
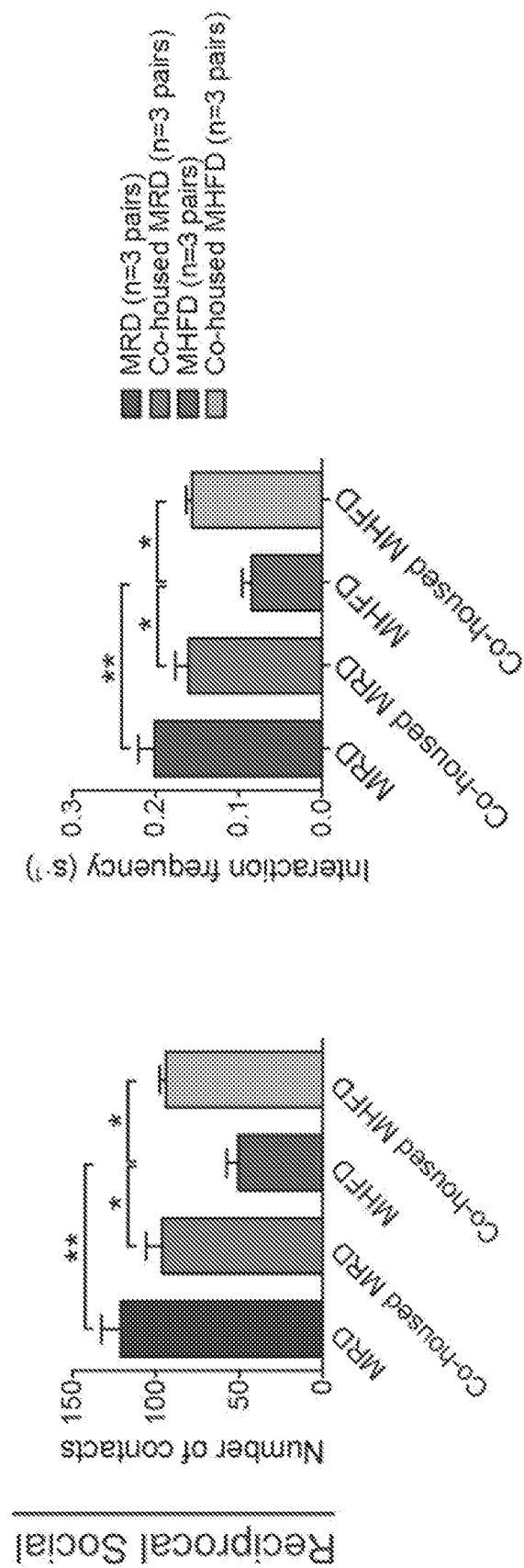
FIGS. 12A-12D: Co-housing a Single MHFD with Three MRD Offspring Reversed the Social Deficits of MHFD Offspring, Related to FIGS. 2A-2G.
Figure 12D:
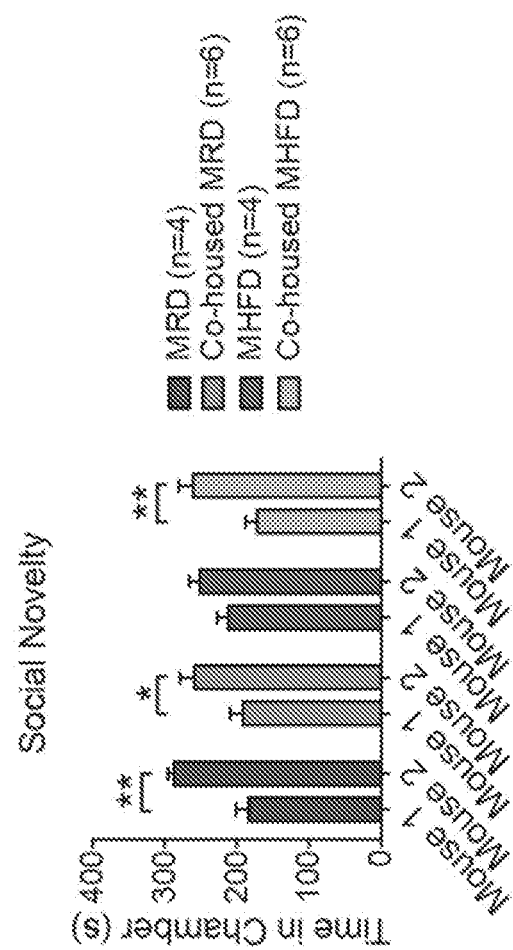
Figure 12C:
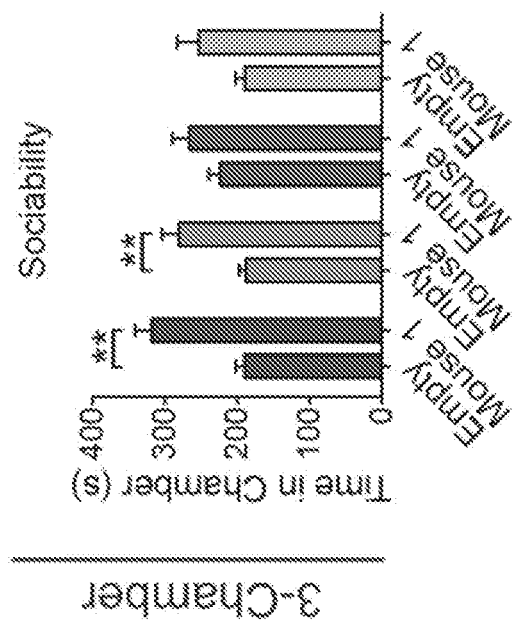
Figure 13B:
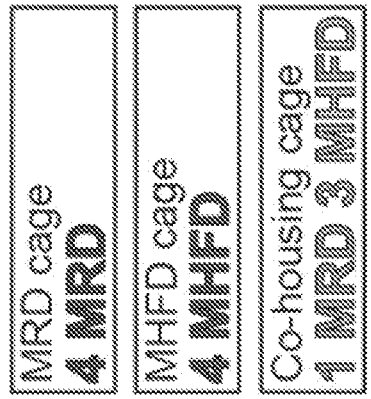
Figure 13A:
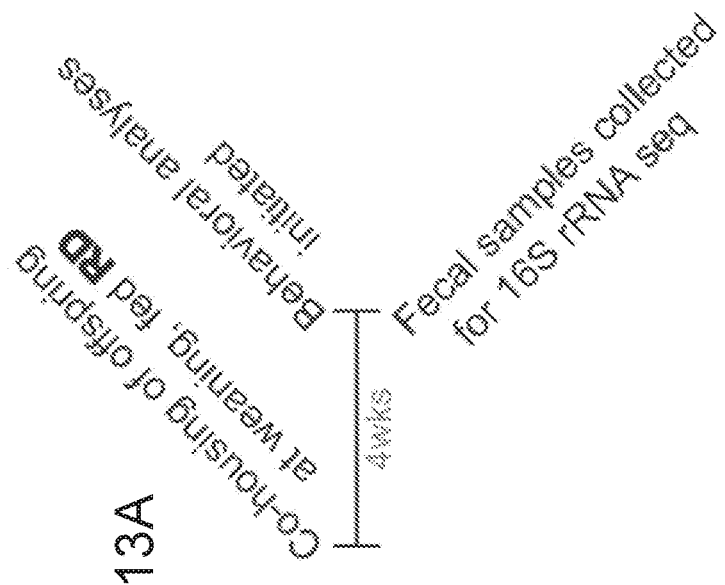
Figures 13C, 13D:
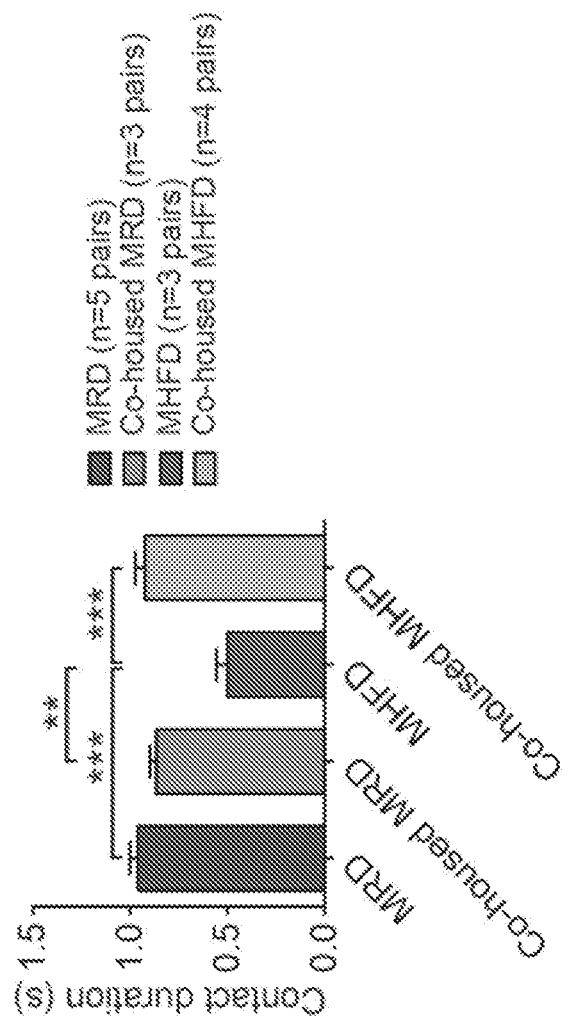
Figure 13G:
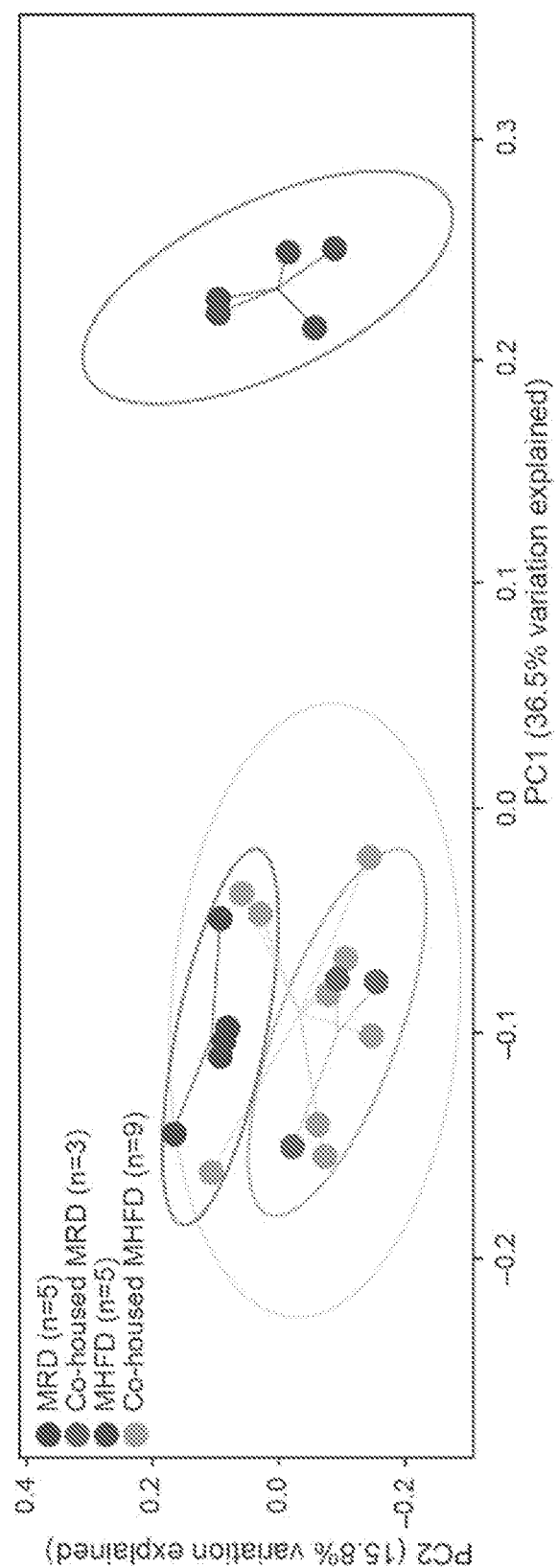
Figure 14A:
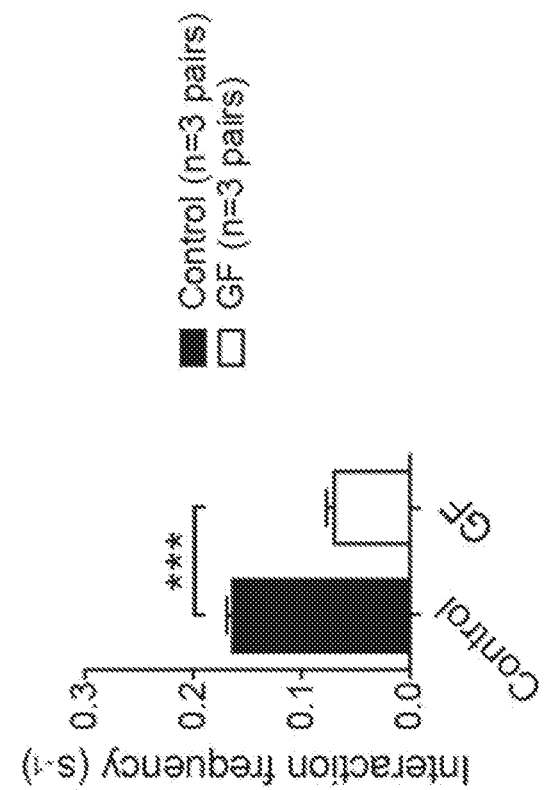
Figure 14B:
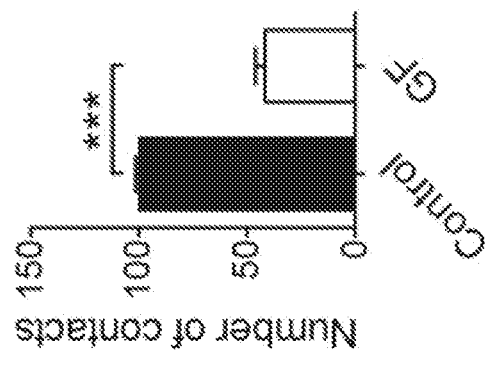
Figure 14D:
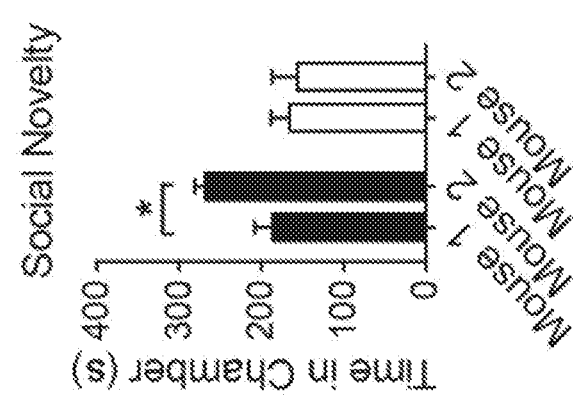
Figure 14C:
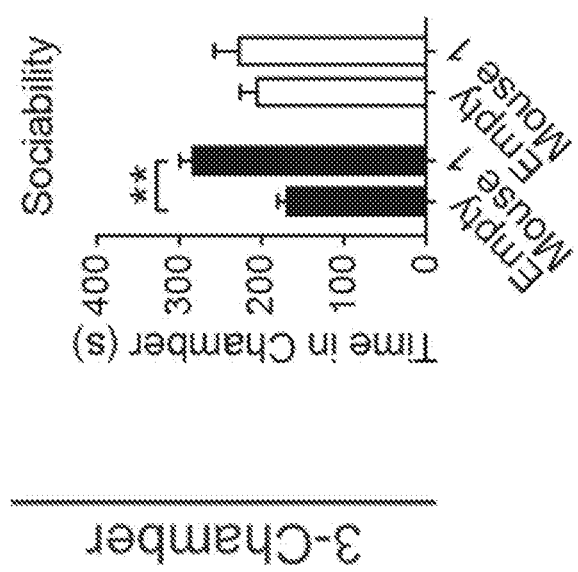
Figure 14E:
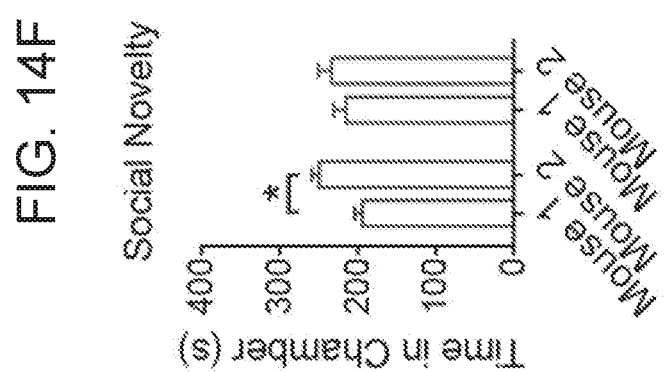
Figure 14F:
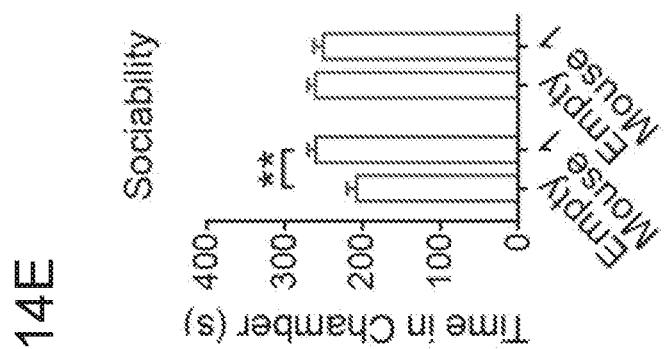
Figure 15A:
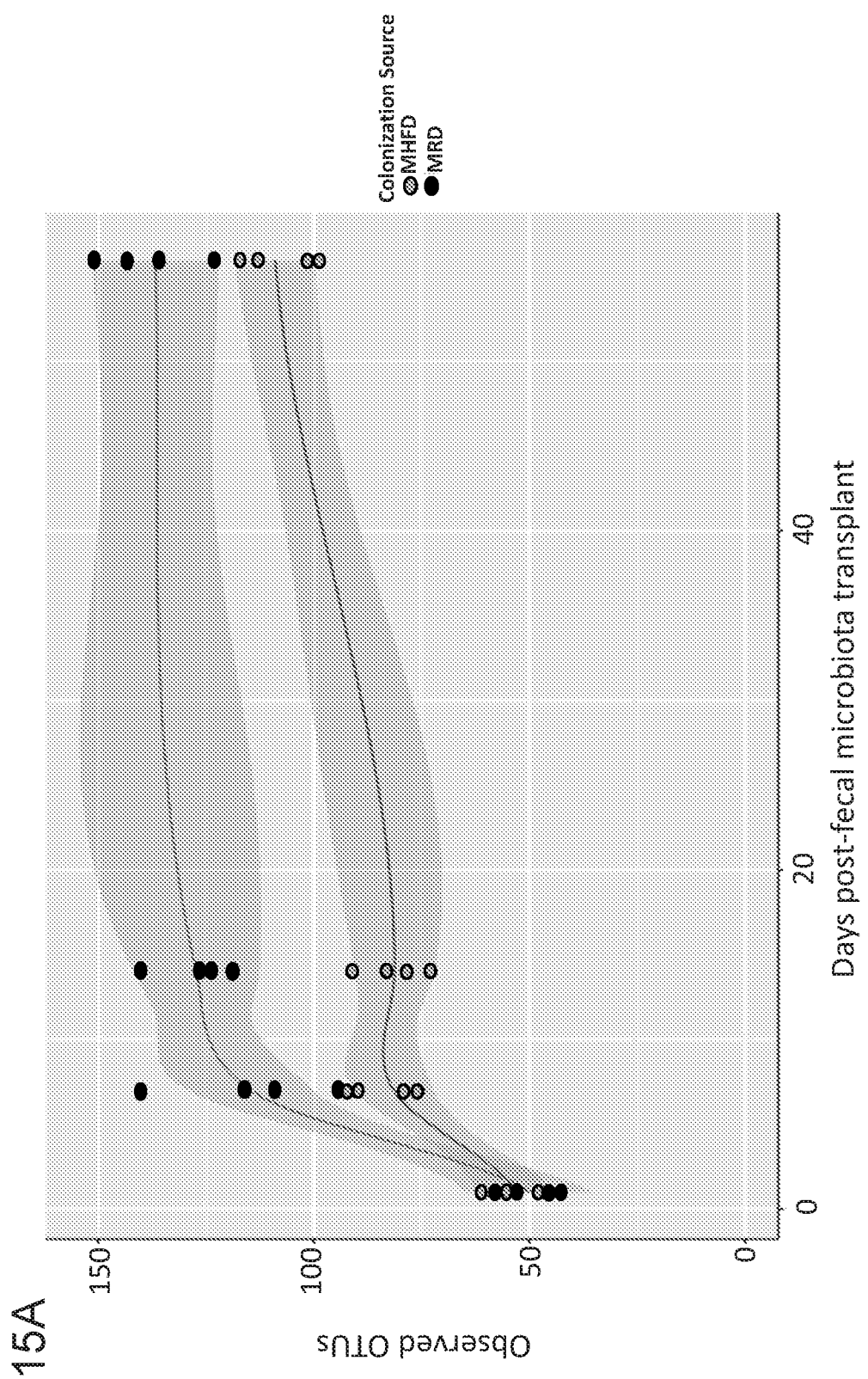
FIGS. 15A-15F: Bacterial Community Diversity Differs Between GF Mice Receiving MRD Versus MHFD Fecal Microbiota, Related to FIGS. 3A-3L.
Figures 15B, 15C, 15D, 15E, 15F:
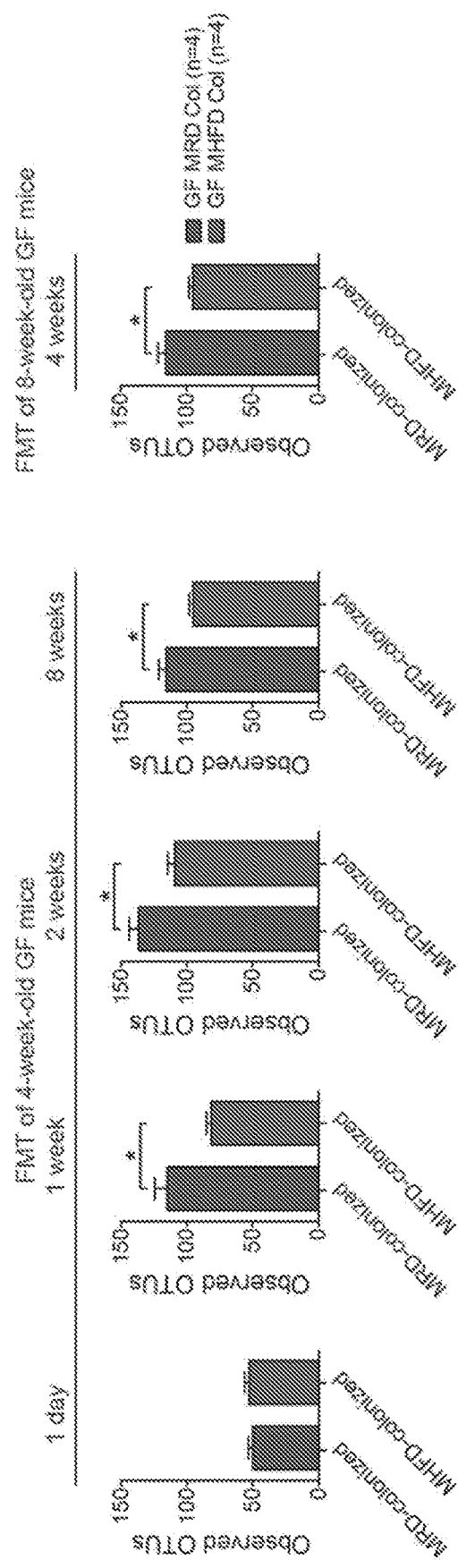

A variety of factors could contribute to the etiology of MHFD-induced social behavioral abnormalities. However, maternal obesity has been shown to alter the gut microbiome of offspring (Galley et al., 2014; Ma et al., 2014) and individuals diagnosed with ASD often co-present dysbiosis of the gut microbiota (Kohane et al., 2012; Mayer et al., 2014; Parracho et al., 2005). To examine whether MHFD induces alterations in offspring gut microbiota, the bacterial composition and community structure in the feces of MRD and MHFD offspring were analyzed by 16S ribosomal RNA (rRNA) gene sequencing. The microbial communities in both MRD and MHFD offspring were comprised of a typical mouse gut microbiota, dominated by Bacteroidetes and Firmicutes (FIGS. 10A-10D). While bacterial diversity computed based on weighted UniFrac distances [the assessment of community structure by considering abundance of operational taxonomic units (OTUs)] did not differ significantly between the offspring from either diet group (FIG. 10E), unweighted analyses of UniFrac distances (assessment of community structure by considering only OUT presence/absence) revealed a marked difference between the structures of the bacterial communities (FIG. 1J). Moreover, the diversity of microbiota in MHFD offspring was reduced compared to MRD microbiota (FIG. 10F). Consistent with previous reports (Turnbaugh et al., 2006), an HFD regimen in mothers induced a remarkable change in the maternal microbiome composition and diversity (FIGS. 11A and 11B), which was similar to that observed in their offspring (FIGS. 1J and 10F).

Gut Microbiota Mediate MHFD-Induced Social Deficits.

Figure 2B:
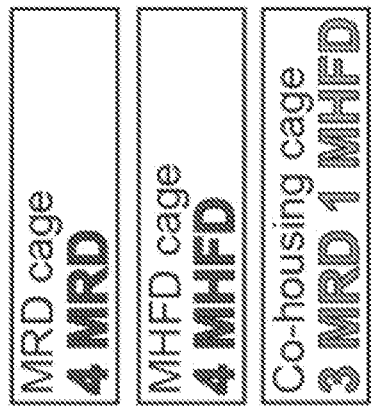
Figure 2A:
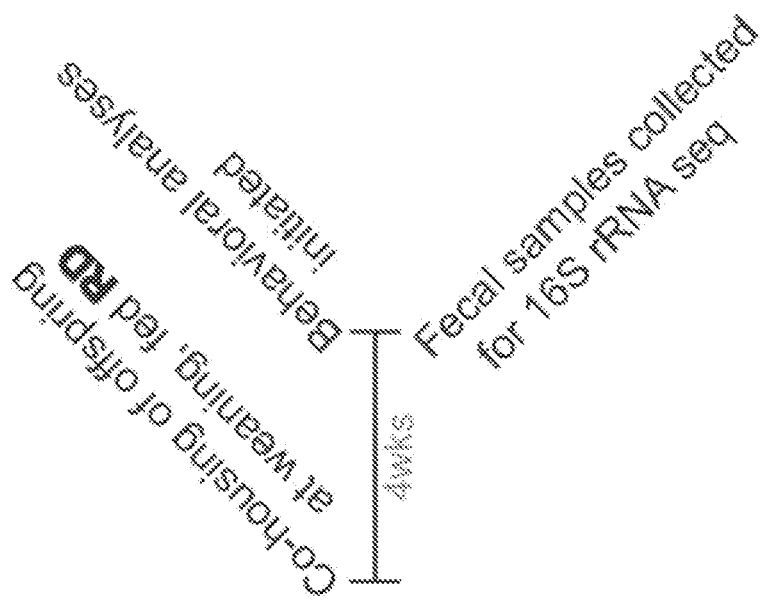

While microbial communities vary across individuals (Yatsunenko et al., 2012), co-housed family members are known to share their microbiota (Song et al., 2013). Since mice are coprophagic and transfer gut microbiota between each other by the fecal-oral route (Ridaura et al., 2013), it was examined whether co-housing MHFD with MRD mice prevents the social deficits in MHFD offspring. To this end, at weaning (3 weeks) an MHFD mouse was co-housed with three MRD mice (FIGS. 2A and 2B). Control groups consisted of individual cages containing either four MHFD mice or four MRD mice (FIG. 2B). Fecal samples were collected and social behavior in MRD and MHFD offspring was assessed when mice were 7-8 weeks old. Strikingly, MHFD mice co-housed with MRD mice exhibited normal reciprocal social interactions (FIGS. 2C, 2D, 12A, and 12B), as well as normal sociability and preference for social novelty, as determined by the 3-chamber test (FIGS. 2E, 2F, 12C, and 12D). Thus, co-housing with control mice corrects social deficits in MHFD offspring.

Figure 2G:
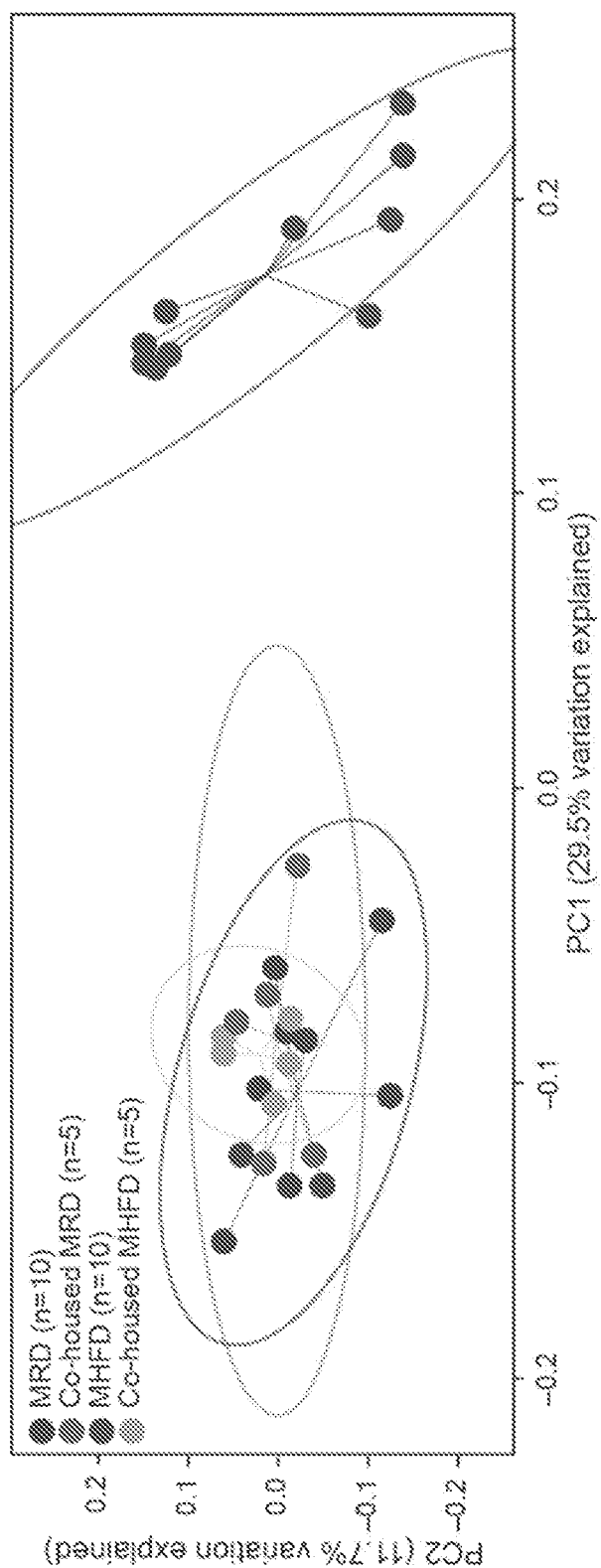

It was next examined whether co-housing also corrected the changes in the microbiota of MHFD offspring. Indeed, co-housing caused a shift in the bacterial phylogenetic profile of MHFD mice to resemble that of MRD or MRD co-housed mice (FIG. 2G), thus correcting the MHFD-induced alterations in the commensal microbiota. In agreement with the idea that the fecal microbiota of MHFD offspring lacks one or more beneficial bacterial species required for normal social behavior, co-housing one MRD with three MHFD offspring was sufficient to rescue both the social behaviors and microbiota phylogenetic profile of MHFD offspring (FIGS. 13A-13G).

Colonization of Germ-Free (GF) Mice with the Microbiota from MRD, but not MHFD Mice, Reverses their Deficient Social Behavior.

Studies on GF mice have shown that the intestinal microbiota can influence brain development and function (Cryan and Dinan, 2012). It was considered that, if the lack of one or more bacterial species in the microbiota of MHFD offspring is responsible for their defective social behavior, GF mice should also be socially deficient. Confirming this consideration, social behaviors were impaired in GF mice (FIGS. 3A-3D and 14A-14D).

To identify functional differences between gut microbial communities and determine whether their role is causal, (gavaged) fecal microbiota were transplanted from adult MRD and MHFD offspring into 4 week- (FIG. 3E) and 8 week-old (FIG. 3F) GF ice. Interestingly, GF mice that received fecal microbiota from MRD offspring at weaning (4 weeks; FIGS. 3G, 3H, 14E and 14F), but not at 8 weeks (FIGS. 3I, 3J, 14G, and 14H), showed normal social behavior. By contrast, GF mice that received fecal microbiota from MHFD offspring remained socially impaired, regardless of the age at which the fecal transfer was performed (FIGS. 3G-3I and 14E-14H). Moreover, as in the case of the phylogenetic separation of MRD and MHFD microbiota (FIG. 1J), the bacterial communities in GF mice receiving feces from MHFD donor offspring clustered separately from those of GF mice receiving feces from MRD donor offspring, irrespective of whether the fecal transplant was performed at 4 or 8 weeks (FIGS. 3K, 3L, and 15A-15F). These data reveal a neurodevelopmental window during which microbial reconstitution effectively improves social behavior.

MHFD Negatively Impacts a Subset of Bacteria in the Intestinal Gut and Selective Re-Introduction of *Lactobacillus* (*L.*) *reuteri* Restores Social Deficits in MHFD Offspring.

Figure 7:
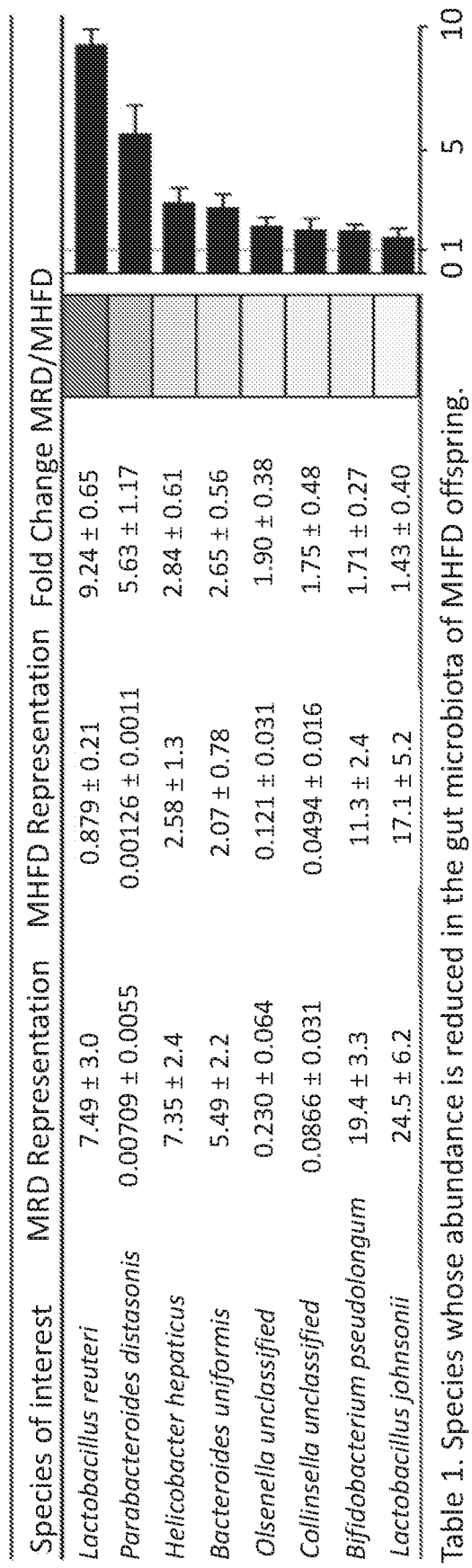
FIG. 7: Species whose abundance is reduced in the gut microbiota of MHFD offspring.
Figure 9C:
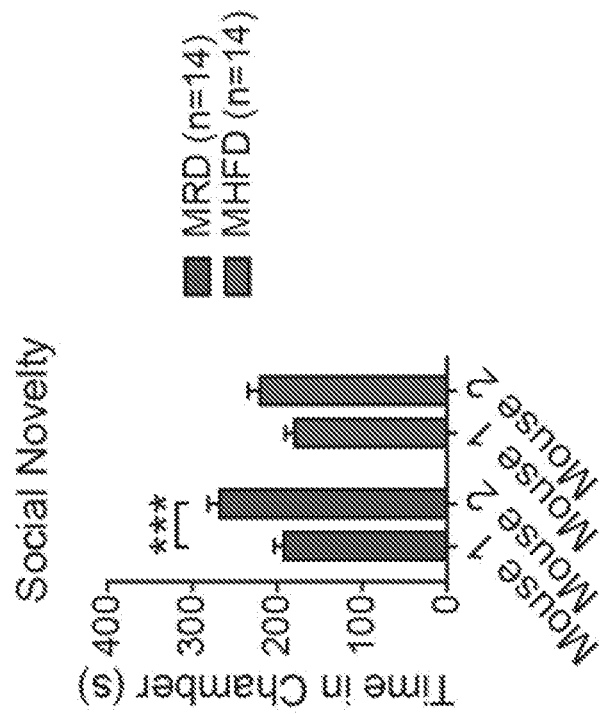
Figure 9D:
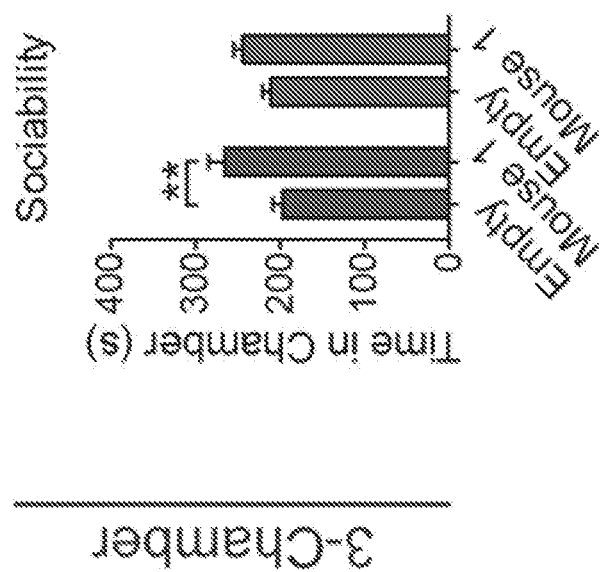

To investigate which bacterial species are absent in the microbiota community of MHFD offspring, metagenomic shotgun sequencing was performed of fecal samples from both MHFD and MRD offspring. The analysis identified several species whose relative abundance was dramatically reduced in the MHFD offspring microbiota (FIG. 7). Among these, *L. reuteri* was the most drastically reduced (>9-fold) in MHFD microbiota population, compared to the MRD microbiota (FIG. 7).

Figure 4A:
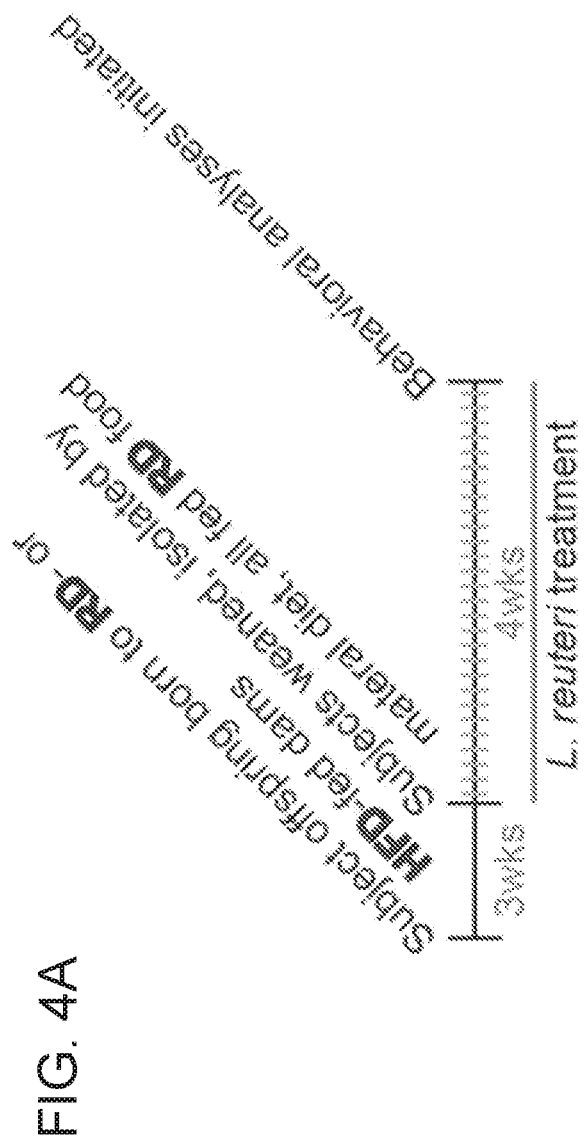
Figure 4E:
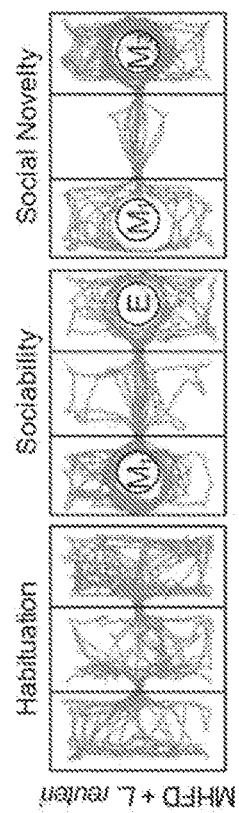
FIGS. 4D-4E, Representative track plots showing exploratory activity.
Figure 4D:
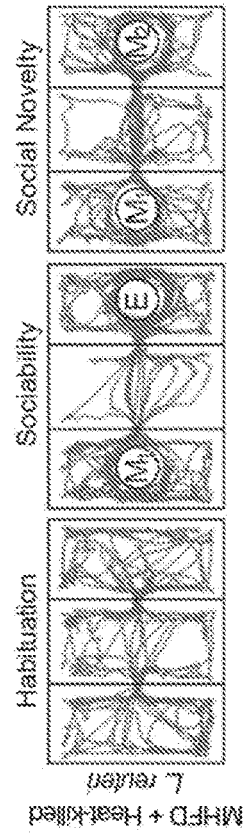
Figure 16A:
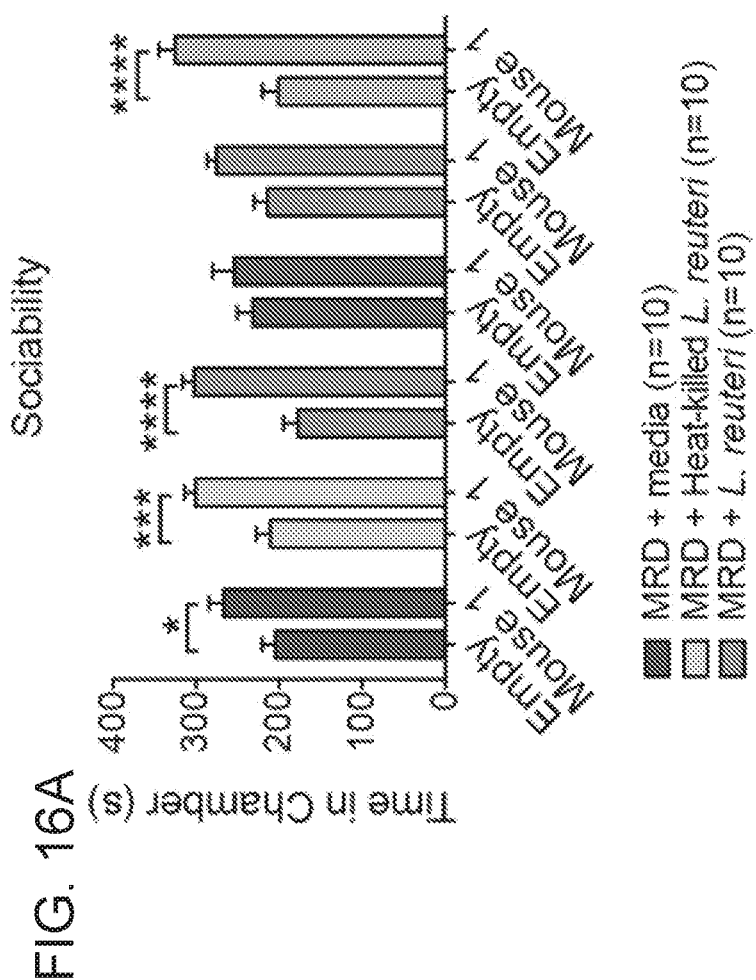
Figure 16C:
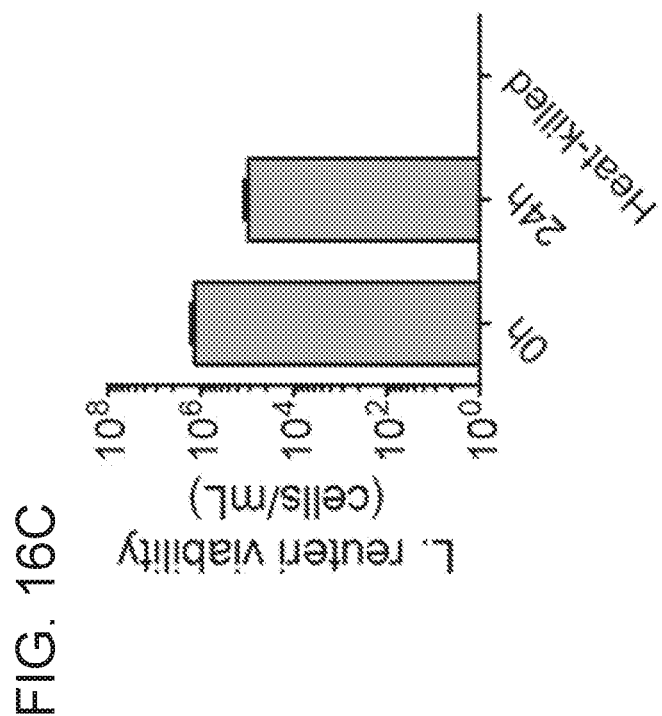
Figure 17A:
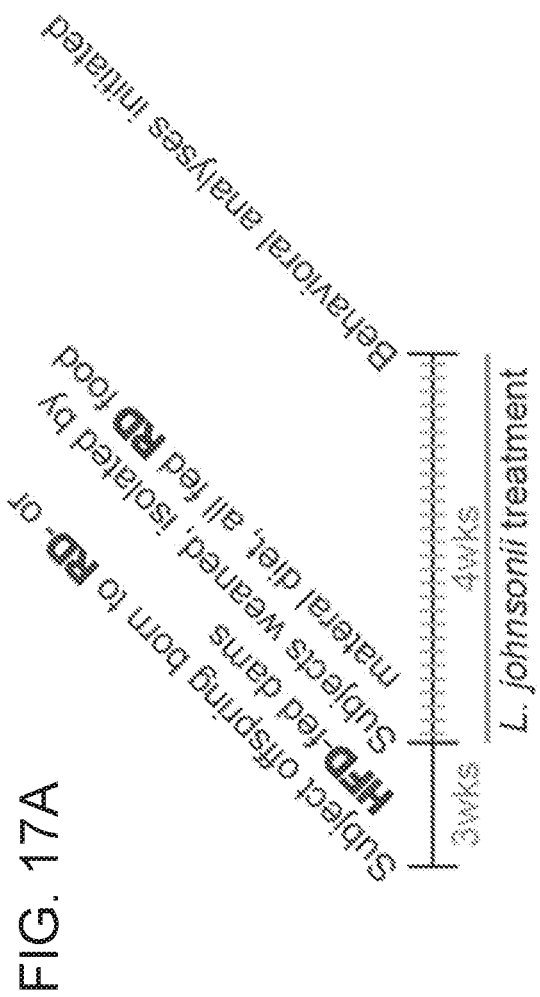
Figures 17E, 17G:
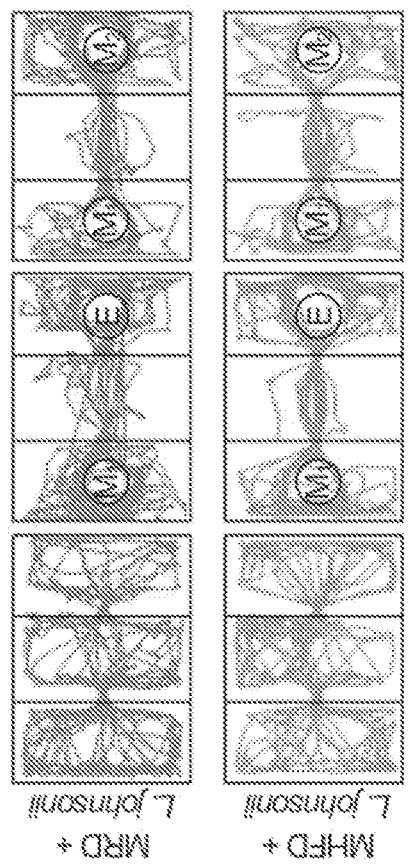
Figures 17D, 17F:
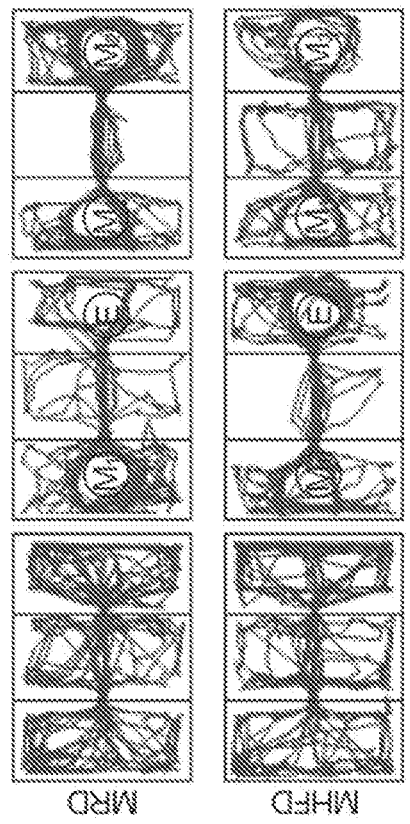

*L. reuteri* has been shown to promote oxytocin levels (Poutahidis et al., 2013), a hormone that plays a crucial role in social behaviors (Donaldson and Young, 2008). It was considered that the selective decrease in *L. reuteri* in the microbiota of MHFD offspring was causally related to their social deficits. To characterize this, *L. reuteri* were introduced into the drinking water of MHFD offspring at weaning, for 4 weeks, after which behavior was tested (FIG. 4A). Remarkably, treatment with *L. reuteri* significantly improved sociability and preference for social novelty in MHFD offspring (FIGS. 4B, 4C, 4E, 16A, and 16B). Results from several control experiments underscore the specificity of *L. reuteri*-mediated rescue of social behaviors in MHFD offspring. First, drinking water treated with either resuspension media or heat-killed *L. reuteri* (80° C. for 20 min) failed to restore social behavior in MHFD offspring (FIGS. 4B-4D, 16A, and 16B). Second, drinking water with live *L. reuteri* did not change the social behavior of MRD offspring (FIGS. 4B, 4C, 16A, and 16B), presumably because their gut microbiota already contains ample *L. reuteri*. Finally, addition of *L. reuteri* to the drinking water had no major effect on bacterial viability and the heat-killing procedure completely abrogated colony-forming units (FIG. 16C). Importantly, the amelioration of the deficient social behavior is specific to *L. reuteri* because similar treatment with another *Lactobacillus* species, *L. johnsonii*, whose abundance is also reduced in the gut microbiota of MHFD offspring (FIG. 7), failed to rescue social behaviors in MHFD offspring (FIGS. 17A-17G).

MHFD offspring show other behavioral traits that are associated with ASD, like repetitive behaviors and anxiety (FIGS. 18A-18B-19A-19F). Interestingly, while co-housing WMHFD with MRD offspring restores social behavior (FIGS. 4B and 4C), it failed to rescue marble burying (FIG.

Figures 19A, 19B:
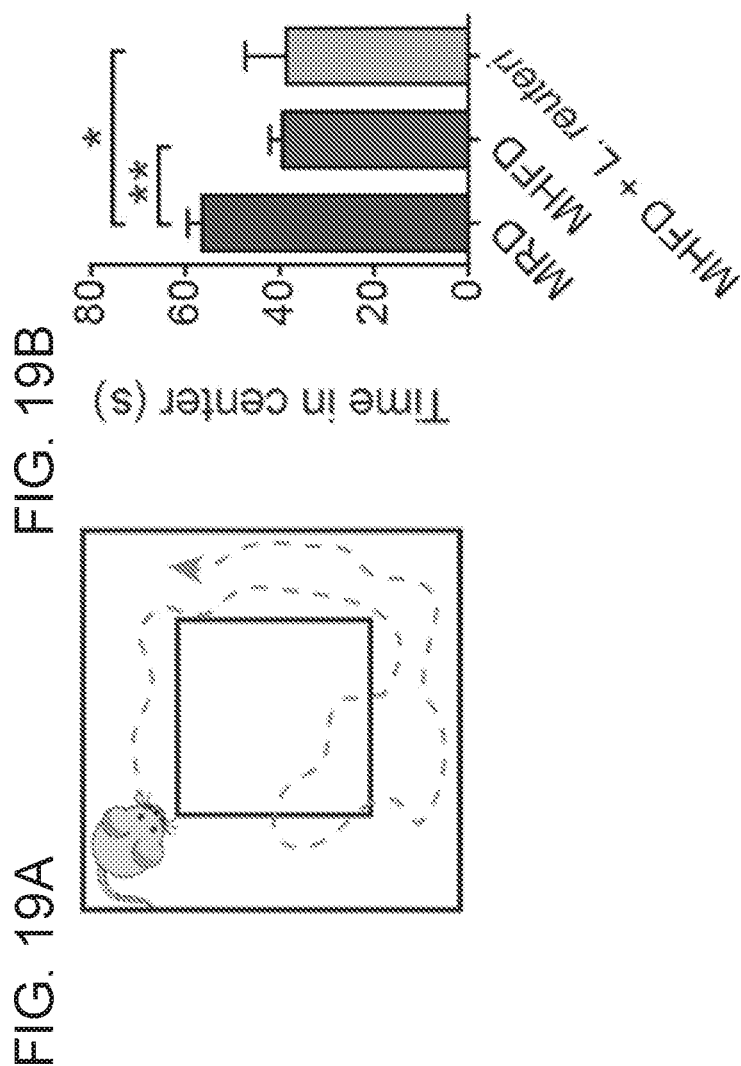
Figure 19C:
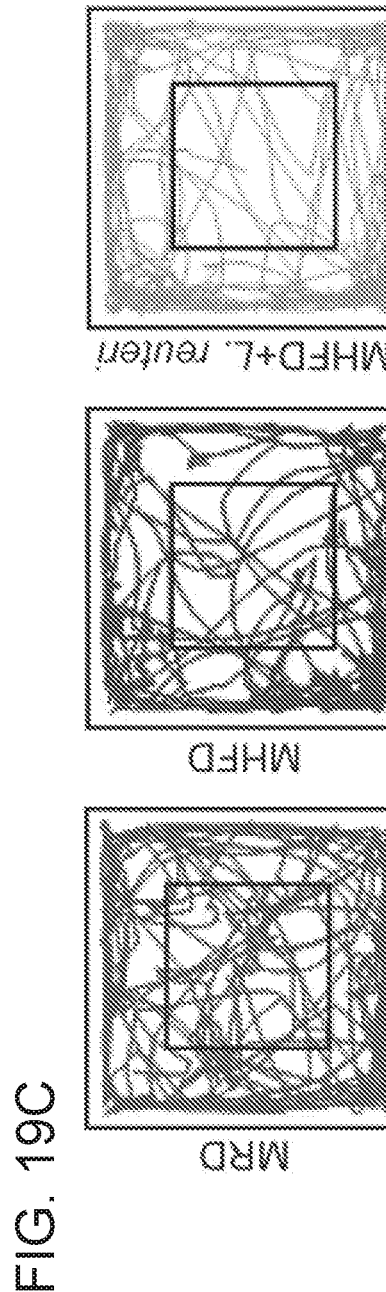

18B), a behavioral task reflecting repetitive and perseverative behavior (Thomas et al., 2009). Accordingly, germ-free mice also showed increased marble burying, and fecal microbial transplants from MRD (or MHFD) offspring into GF mice failed to rescue the repetitive behavior (FIG. 18B). Thus, repetitive behaviors in MHFD offspring do not depend on changes in the gut microbiome. In addition, *L. reuteri* treatment failed to rescue the changes in anxiety in MHFD offspring (FIGS. 19B-19C). Taken together, these data indicate that *L. reuteri* reconstitution specifically rescues social, but not other behavioral endophenotypes associated with ASD.

Oxytocin Levels are Reduced in the Hypothalamus of MHFD Offspring.

There is growing evidence that the neuropeptide oxytocin modulates numerous aspects of social behavior (Donaldson and Young, 2008; Insel, 2010) and is implicated in ASD (Lerer et al., 2008; Wu et al., 2005). *L. reuteri*, which rescued social behaviors in MHFD mice (FIGS. 4B, 4C, and 4E), has been reported to increase oxytocin levels (Poutahidis et al., 2013). Because oxytocin is primarily synthesized in the paraventricular nuclei (PVN) of the hypothalamus, it was considered to compare the number of oxytocin-expressing cells in the PVN of MRD and MHFD offspring. Interestingly, MHFD offspring had significantly fewer oxytocin immunoreactive neurons compared to MRD offspring (FIGS. 4F-4H, 4K, and 4L). The reduction in oxytocin immunoreactivity was not due to an overall decrease in PVN neurons, because the total number of neurons was unchanged (as measured by NeuN staining; FIGS. 4G, 4H, 4M, and 4N). Notably, in *L. reuteri*-treated MHFD offspring, the number of oxytocin-expressing cells was higher than in control-treated MHFD offspring (FIGS. 4I, 4J, 4O, and 4P). Thus, the number of oxytocin immunoreactive neurons in the PVN is reduced in MHFD offspring but can be restored by *L. reuteri* treatment.

Mesolimbic Dopamine Reward System Function is Impaired in MHFD Offspring.

Figure 5A:
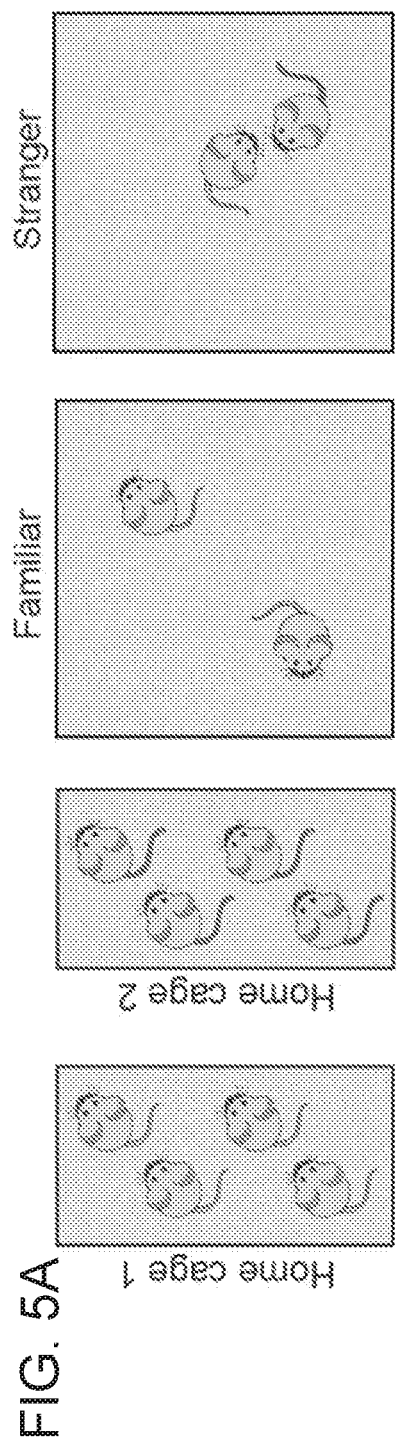
Figure 5D:
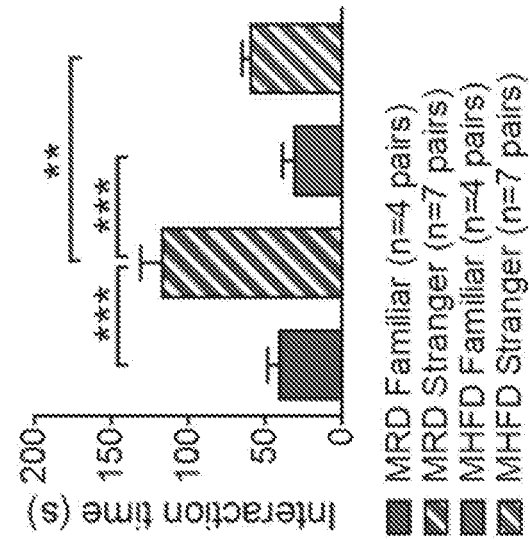
Figure 20B:
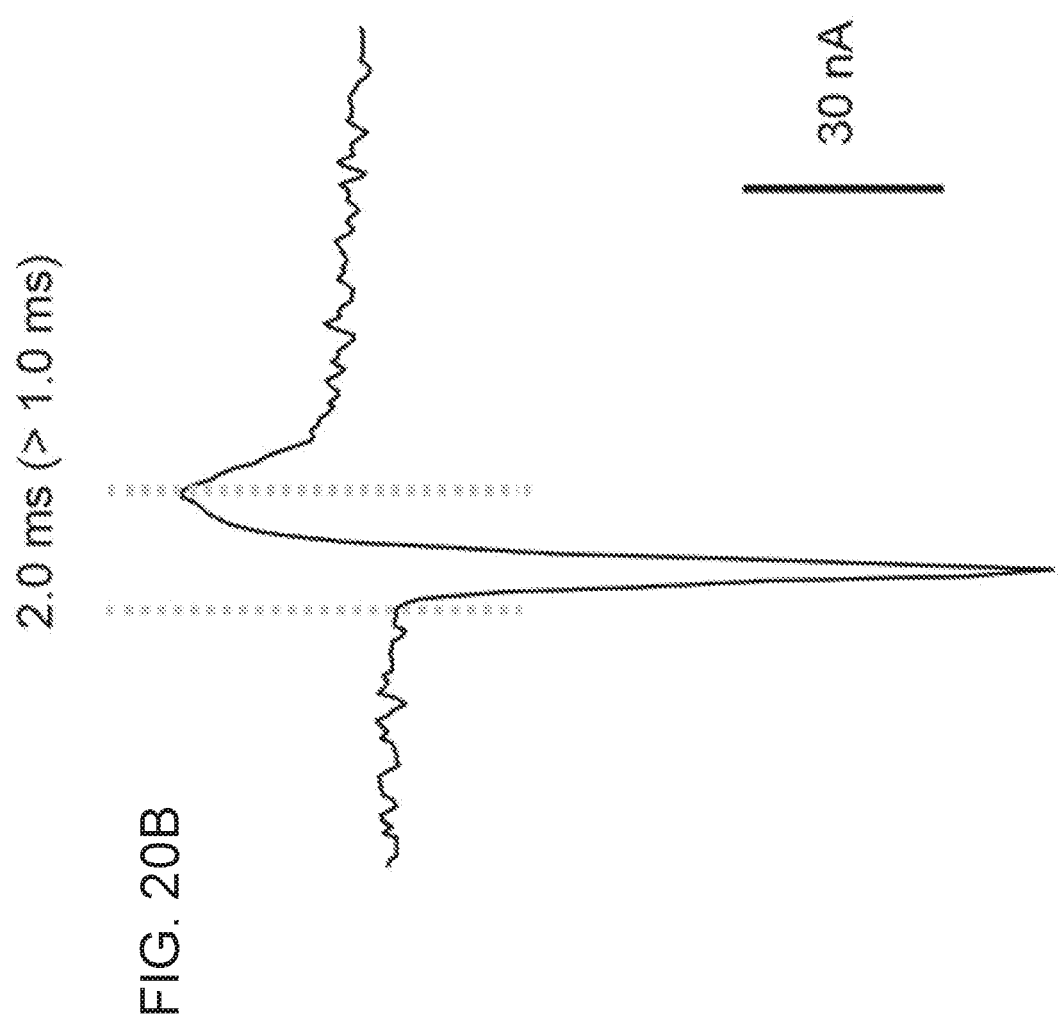
Figure 20C:
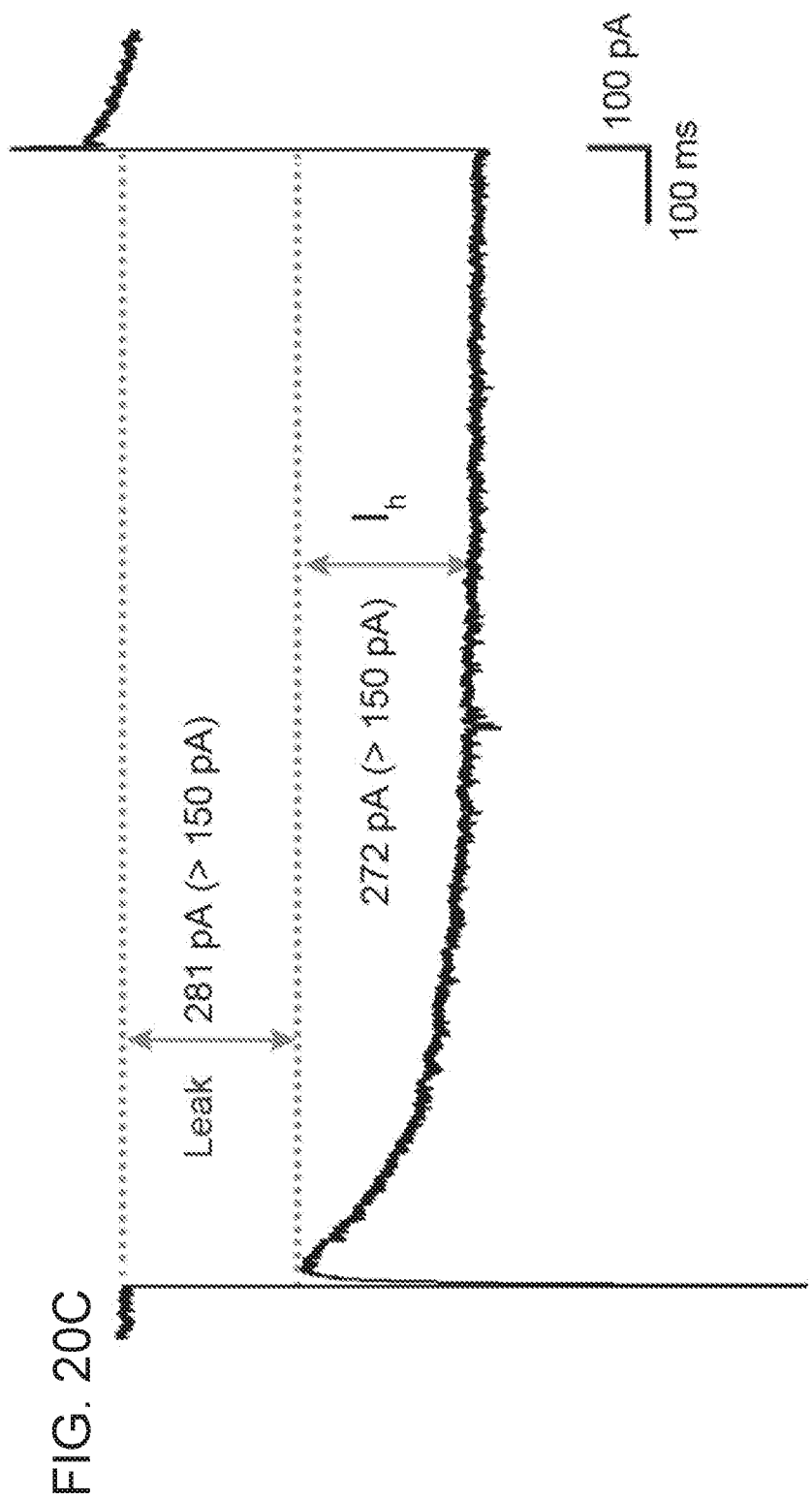
Figure 21A:
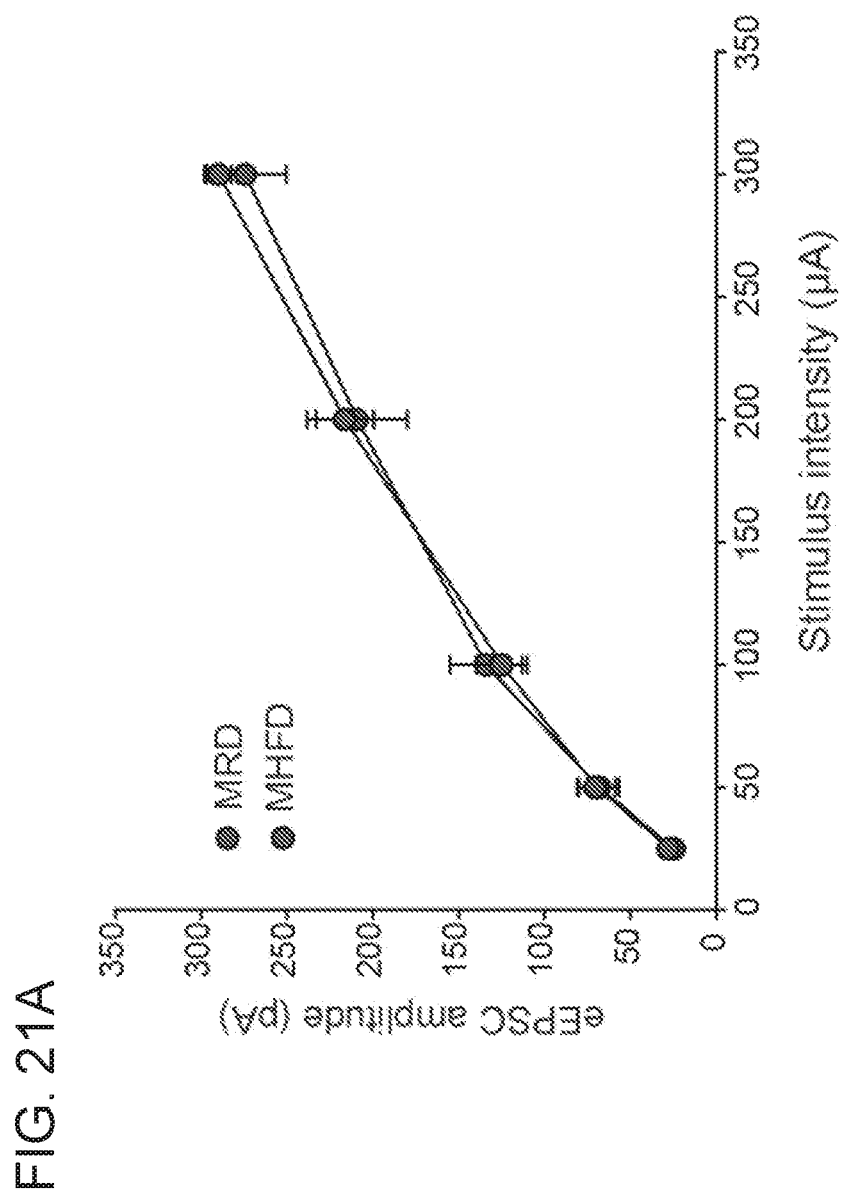
FIGS. 21A-21D: Basal Synaptic Transmission is Unaltered in VTA Slices from MHFD Mice, Related to FIGS. 5A-5L and 6A-6F. Excitatory postsynaptic currents (EPCS) were recorded as described by Zhu et al. (2011).
Figure 21B:
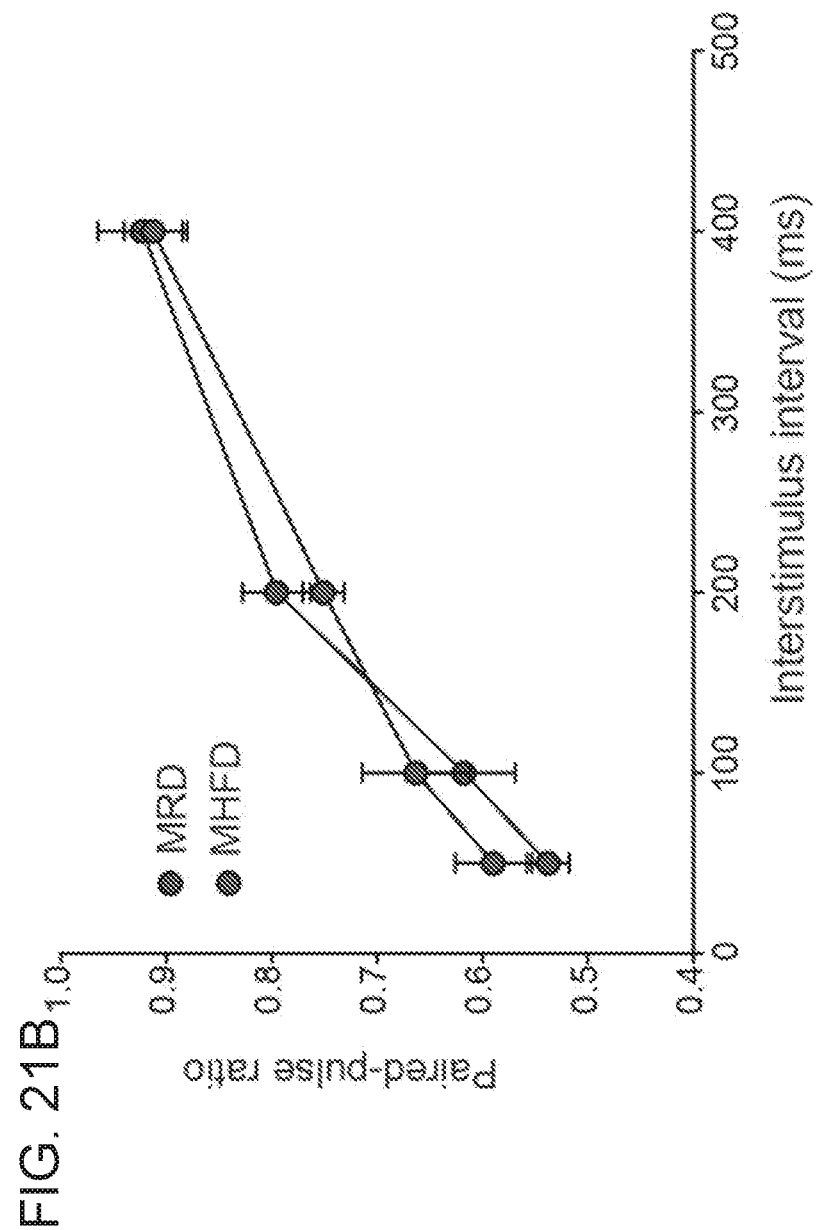
Figure 21C:
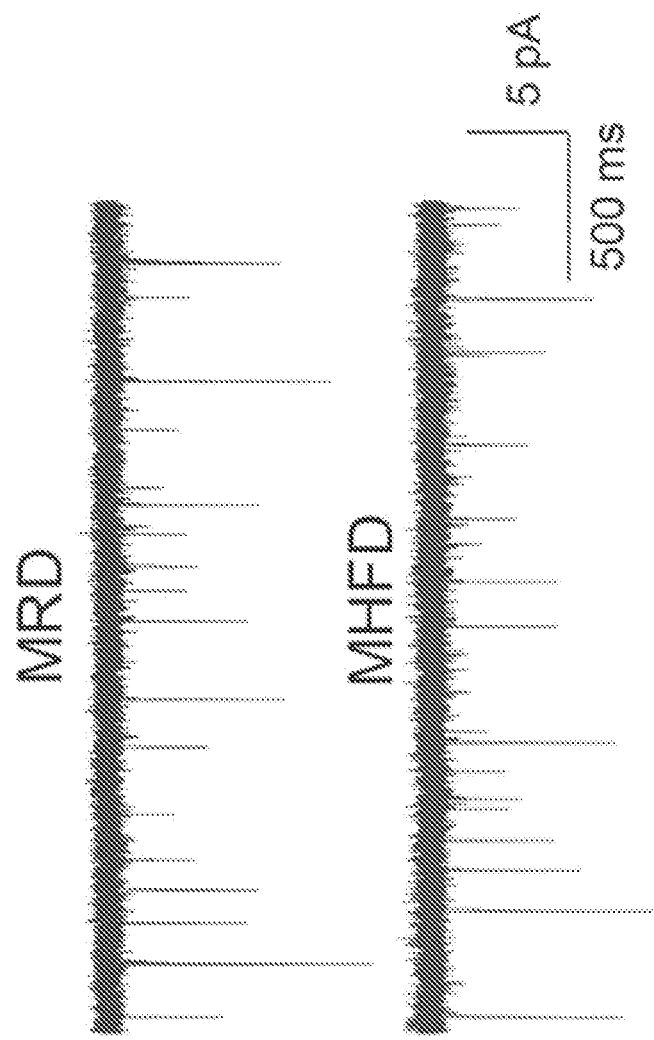
Figure 21E:
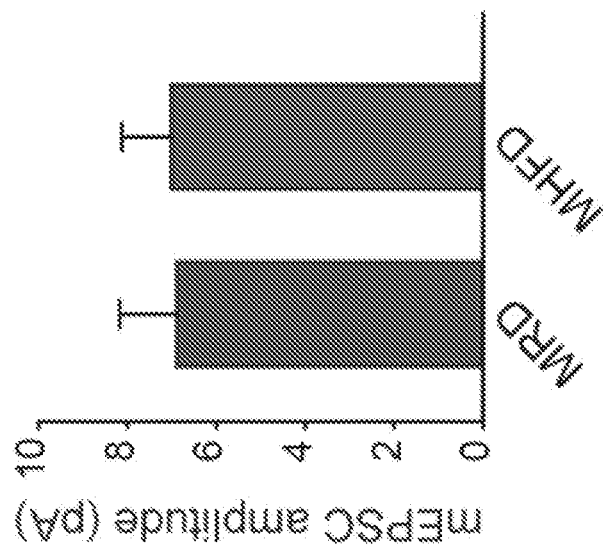
Figure 21D:
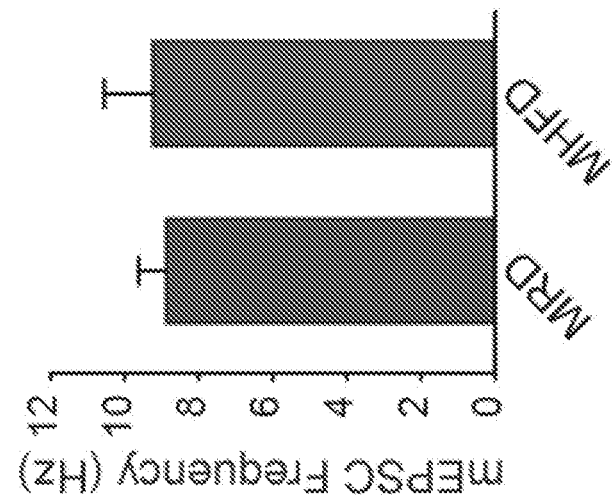
Figure 22A:
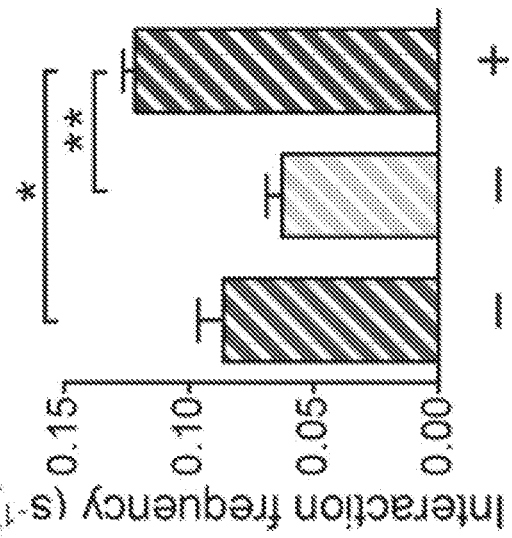
Figure 22B:
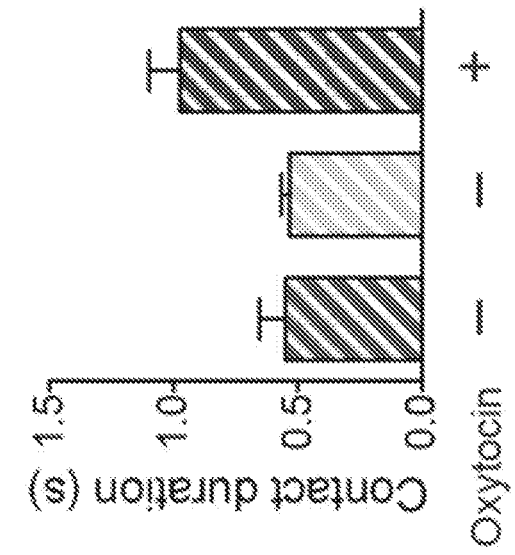

Brain regions responding to naturally rewarding stimuli, including the ventral tegmental area (VTA) and the nucleus accumbens (NAc), are crucially involved in social behaviors (Dolen et al., 2013; Gunaydin et al., 2014; Huang and Hessler, 2008). In addition, oxytocin-expressing neurons in the PVN project to the VTA (Melis et al., 2007). Oxytocin activates VTA neurons in both mice and humans, influencing the processing of socially relevant cues (Gregory et al., 2015; Groppe et al., 2013; Tang et al., 2014) and oxytocin receptor blockade in the VTA prevents social attachment in rodents (Pedersen et al., 1994). Given that social stimulation can be particularly rewarding and triggers synaptic potentiation in VTA DA neurons of birds (Huang and Hessler, 2008), it was considered whether direct social interaction evokes long-term potentiation (LTP) of synaptic inputs to VTA DA neurons (FIGS. 20A-20C). To this end, AMPAR/NMDAR ratios were recorded of glutamatergic excitatory postsynaptic currents (EPSCs) in MRD and MHFD offspring 24 hours following a 10 min reciprocal interaction with either a stranger or a familiar mouse (FIG. 5A). In control MRD mice, social interaction with a stranger, but not a familiar mouse, triggered LTP in VTA DA neurons, as determined by an increase in AMPAR/NMDAR ratios (FIGS. 5B and 5D). By contrast, in MHFD offspring, social interaction with a stranger failed to induce LTP in their VTA DA neurons (FIGS. 5C and 5E). Input-output curves, paired-pulse ratios and miniature EPSCs (mEPSCs) frequency and amplitude show that the impairment of LTP induced by social interaction in MHFD offspring cannot be attributed to changes in basal synaptic transmission (FIGS. 21A-21E).

Figure 5F:
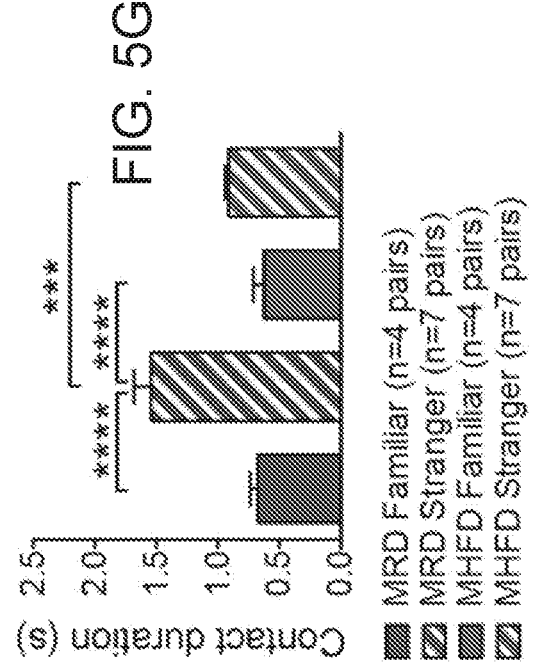
Figure 5E:
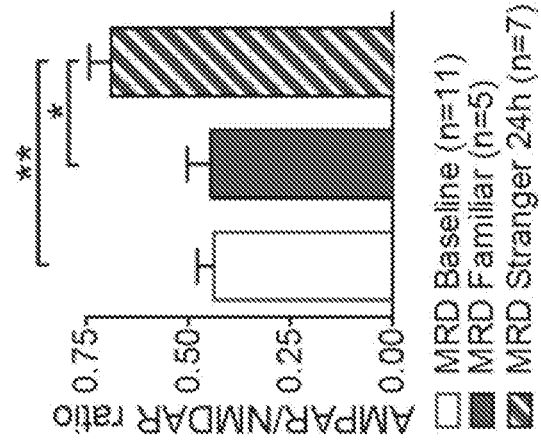
Figure 5G:
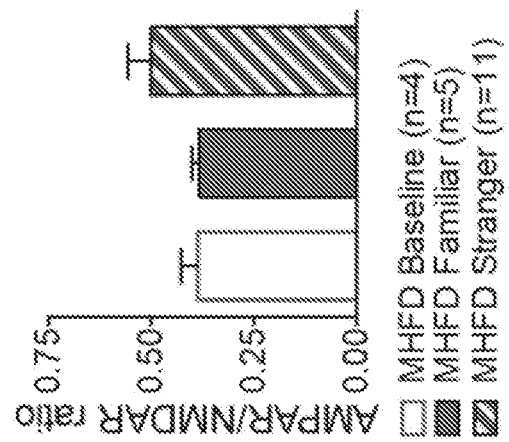

Mirroring the electrophysiological results, MRD offspring spent significantly more time interacting with a stranger than a familiar mouse, but MHFD offspring did not (FIGS. 5F and 5G). Thus, social interaction induces a long-lasting increase in the activity of the dopaminergic reward system of MRD, but not in MHFD, offspring.

Treatment with *L. reuteri* or Oxytocin Reverses both the LTP in VTA DA Neurons and Social Behavior in MHFD Offspring. It was next considered whether *L. reuteri* treatment, which restores sociability and preference for social novelty in MHFD offspring (FIGS. 4B, 4C, and 4E), would also rescue reciprocal social interaction and related changes in synaptic strength in the VTA. Live (FIGS. 5H and 5J), but not heat-killed (FIGS. 5I and 5K), *L. reuteri* rescued stranger interaction-induced LTP in the VTA as well as reciprocal social interactions in MHFD offspring (FIG. 5L). Thus, *L. reuteri* restores social interaction-induced LTP in the VTA of MHFD offspring.

Figure 6B:
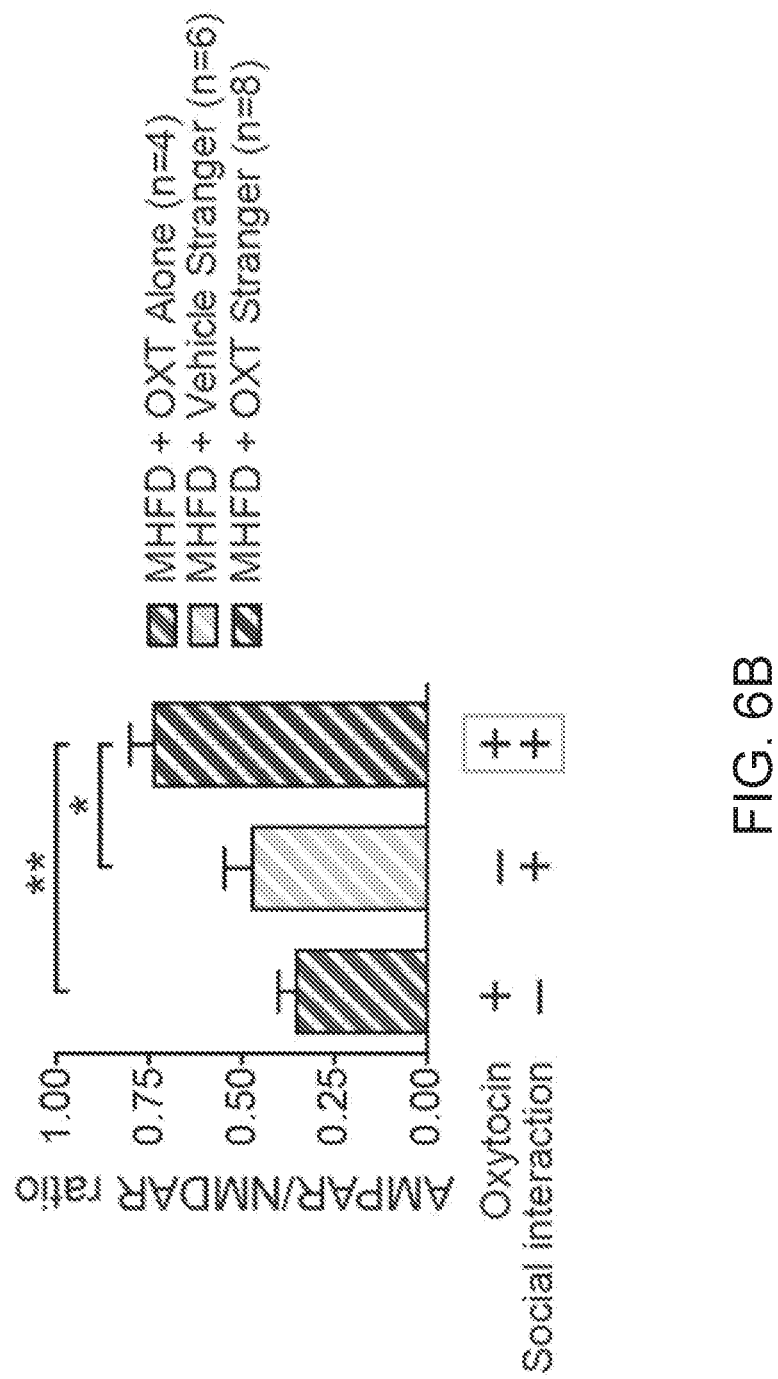
Figures 6E, 6F:
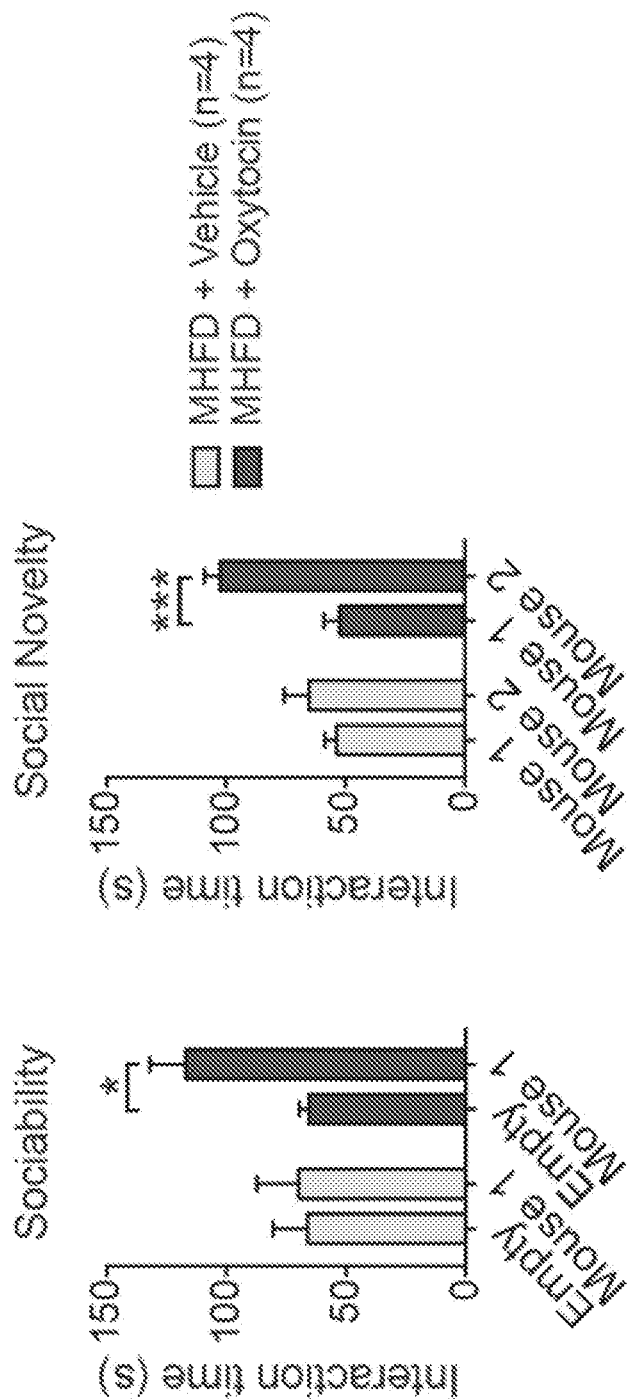

These findings, together with the fact that *L. reuteri* treatment increased oxytocin immunoreactivity in the PVN of MHFD offspring (FIGS. 4I, 4J 4O and 4P), led to examination of whether direct oxytocin application could also reverse the behavioral and electrophysiological deficits characteristic of MHFD offspring. To characterize this, oxytocin was administered intranasally—a preferred method of administering neuropeptides to the brain bypassing more invasive procedures (Penagarikano et al., 2015)—to MHFD offspring and reciprocal social interactions was measured 30 min later. Although either oxytocin alone or social interaction alone failed to rescue social interaction-induced LTP in VTA, the combination of social interaction and oxytocin treatment restored LTP in the VTA of MHFD offspring (FIGS. 6A and 6B), supporting prior work implicating a synergistic effect of oxytocin and dopamine in the processing of socially relevant cues (Modi and Young, 2012). Accordingly, oxytocin treatment improved reciprocal social interaction (FIGS. 6C, 6D, 22A, and 22B), as well as sociability and the preference for social novelty (FIGS. 6E, 6F, 22C, and 22D). Thus, oxytocin administration rescues social behavior and related neural adaptations in the VTA of MHFD offspring.

Collectively, the data show that MHFD impairs oxytocin-mediated synaptic adaptations in the VTA that underlie social behaviors.

Significance of Certain Embodiments

Precise Microbiome Reconstitution Holds Therapeutic Potential for Individuals with ASD and Other Neurodevelopmental Disorders.

A recent survey from the Center for Disease Control and Prevention estimates that about one out of 45 children is affected with ASD (Zablotsky et al., 2015). Despite the significant increase in its incidence, there are currently no medications that can cure ASD or treat the core symptoms. Thus, the development of novel treatment strategies is of crucial importance. Although both genetics and the environment, and their interactions, are suspected to cause ASD, environmental factors may account for a large proportion of the ASD cases (Hallmayer et al., 2011). Strikingly, the increasing prevalence of ASD is mirrored by the increase in adult obesity. This represents a major health issue as over half of U.S. infants are born to mothers who are either obese or exposed to high fat diet (HFD) during pregnancy (Ogden et al., 2014) and there is a growing body of evidence that maternal obesity heightens the risk of neuropsychiatric disorders in offspring, including ASD (Krakowiak et al., 2012; Sullivan et al., 2014). Indeed, a recent study found that mothers with obesity were 1.5 times more likely to have a child with ASD, and the increased risk of children with ASD was two-fold greater for pregnant mothers with both obesity and gestational diabetes (Connolly et al., 2016). While most of the focus in the field has been on inflammation (Bolton and Bilbo, 2014) or epigenetic changes (Mathers and McKay, 2009), the biological mechanism by which maternal obesity affects offspring neurodevelopment remains unclear. Here it is shown that that the behavioral dysfunction associated with MHFD-induced obesity is induced by alterations in the offspring gut microbiota. Several lines of evidence support this idea. First, individuals diagnosed with ASD often co-present dysbiosis of the gut microbiota (Kohane et al., 2012; Mayer et al., 2014; Parracho et al., 2005). Second, maternal obesity leads to alterations in the offspring's gut microbiome in humans and non-human primates (Galley et al., 2014; Ma et al., 2014). Third, in mice, the gut microbiota of MHFD offspring is altered (FIGS. 1A-1J) by the reduction in specific bacterial species (FIG. 7). Fourth, manipulation of the microbiome community by co-housing MHFD with MRD offspring rescues MHFD-induced social deficits and corrects their microbial phylogenetic profile (FIGS. 2A-2G). Fifth, GF mice are socially impaired and fecal microbiota transplanted from MRD (but not MHFD) offspring rescues GF social behavior (FIGS. 3A-3L). Finally, treatment with a single bacterial species, *L. reuteri*, which is dramatically reduced in MHFD offspring (FIG. 7), restores social behavior in MHFD mice (FIG. 4A-4P).

In specific embodiments, there is a model in which *L. reuteri* improves social behavior by promoting oxytocin-mediated functions. Consistent with this model, *L. reuteri*-treatment enhances oxytocin levels in the PVN of MHFD mice (FIGS. 4I and 4J) and direct oxytocin treatment normalizes the social behavior of MHFD (FIGS. 6A-6F). In specific embodiments, *L. reuteri* promotes oxytocin in the brain because the vagus nerve (Davari et al., 2013; Foster and McVey Neufeld, 2013) is the main pathway of communication between the gut/*L. reuteri* and changes in oxytocin in the PVN. It is known that vagal nerve fibers project to the PVN (Sabatier et al., 2013; Uvnas-Moberg et al., 2014). In addition, neuronal activity in the PVN induced by bacterial colonization is blocked by subdiaphragmatic vagotomy (Wang et al., 2002). Especially relevant are the reports that the *L. reuteri*-mediated increase in oxytocin depends on the vagus nerve (Poutahidis et al., 2013) and that another *Lactobacillus* species, *L. rhamnosus*, reduced stress-induced anxiety in a vagusdependent manner (Bravo et al., 2011).

The results provide new insight into the mechanism by which MHFD causes ASD and how a marked shift in microbial ecology, due to MHFD, can negatively impact social behavior and related neuronal changes in offspring. These neuronal adaptations, which underlie social behavior by enhancing the salience and rewarding value of social stimuli, are surprisingly impaired by maternal diet-induced changes in the gut microbiome (FIGS. 5A-5L). Interestingly, according to a recent paper, probiotic-based restoration of gut permeability in a mouse model of ASD can improve some ASD-like behaviors, but not social behaviors (Hsiao et al., 2013). Given that the inventors identified a different probiotic candidate, *L. reuteri*, that rescues social behavior (FIGS. 4A-4P and 5A-5L), but not other ASD like behaviors (FIGS. 18A-18B and 19A-19F) in MHFD mice, in specific embodiments a carefully selected combination of probiotics are useful as a non-invasive treatment for the millions of patients suffering from ASD.

Example 2

Examples of Materials and Methods

Mice and Maternal Diet.

C57B16/J mice were obtained from Jackson Laboratories (#000-664) and were kept on a 12 h light/dark cycle and had access to food and water ad libitum. Females were placed on either a regular diet (RD) consisting of 13.4% kcal from fat, 30% kcal from protein, and 57% kcal from carbohydrates (Lab Diets, #5001) or high fat diet (HFD) consisting of 60% kcal from fat, 20% kcal from protein, and 40% kcal from carbohydrates (Research Diets, #D12492). Maternal weight was measured weekly. Maternal total and fat mass were measured using an mq7.5 Minispec NMR body composition analyzer. After eight weeks on diet, females were paired with C57B16/J adult males to produce subject offspring. Resulting offspring were weaned at three weeks of age and all placed on RD, regardless of maternal diet (MRD or MHFD). Germ-free mice (C57B16/J) were maintained in a flexible isolator fed with HEPA-filtered air and provided with irradiated food and water. Germ-free offspring were weaned at four weeks of age. All behavioral tests were performed on 7-12-week-old male mice.

Animal care and experimental procedures were approved by Baylor College of Medicine's Institutional Animal Care and Use Committee in accordance with all guidelines set forth by the U.S. National Institutes of Health. Reciprocal Social Interaction. Mice were placed in a 25×25×25 cm Plexiglass arena, to which they had not been previously habituated, with either a familiar (cage-mate) or stranger age- and sex-matched conspecific. In all experiments, paired mice were matched for maternal diet, colonization source, and/or treatment. We recorded the time a pair of mice engaged in social interaction (close following, touching, nose-to-nose sniffing, nose-to-anus sniffing, and/or crawling over/under each other). The human observer was blind to maternal diet and/or treatment group. Social behavior was analyzed with AnyMaze automated software.

Three-Chamber Social Test.

Crawley's three-chamber test for sociability and preference for social novelty was performed as described (Silverman et al., 2010). In brief, the mouse first experienced a 10-minute period of habituation during which it was allowed to freely explore a 60×40×23 cm Plexiglass arena divided into three equally sized, interconnected chambers (Left, Center, Right). Sociability was measured during a second ten-minute period in which the subject could interact either with an empty wire cup (Empty) or a wire cup containing an age and sex-matched stranger conspecific (Mouse 1). Time spent interacting (sniffing, crawling upon) with either the empty cup or the stranger mouse contained in the other cup as well as time spent in each chamber was recorded using the AnyMaze software, by independent observers. Empty cup placement in the Left or Right chamber during the Sociability period was counterbalanced between trials. Finally, preference for social novelty was assayed by introducing a second stranger mouse (Mouse 2) into the previously the empty wire cup. Time spent in each chamber as well as time spent interacting with either Mouse 1 or Mouse 2 was recorded using the automated AnyMaze software by independent observers.

Marble Burying.

Marble burying was performed as previously described (Thomas et al., 2009). Briefly, mice were placed in a standard-sized cage containing 20 regularly-spaced black marbles sitting on fine-wood chipped bedding 5 cm in depth.

After 20 minutes, the mouse was removed and marbles with at least two-thirds of their depth obscured by wood chips were counted as buried.

Open Field.

Mice were placed in an open arena (40×40×20 cm) and allowed to explore freely for 10 minutes while their position was continually monitored using tracking software (ANY-Maze). Tracking allowed for measurement of distance traveled, speed, and position in the arena throughout the task. Time spent in the center of the arena, defined as the interior 20×20 cm, was recorded.

16s rRNA Gene Sequencing.

Methods were adapted from the methods developed for the NIH-Human Microbiome Project (Human Microbiome Project, 2012a, b). Briefly, bacterial genomic DNA was extracted using MO BIO PowerSoil DNA Isolation Kit (MO BIO Laboratories). The 16S rDNA V4 region was amplified by PCR and sequenced in the MiSeq platform (Illumina) using the 2×250 bp paired-end protocol yielding pair-end reads that overlap almost completely. The primers used for amplification contain adapters for MiSeq sequencing and single-end barcodes allowing pooling and direct sequencing of PCR products (Caporaso et al., 2012). The 16S rRNA gene read pairs were demultiplexed based on the unique molecular barcodes, and reads were merged using USE-ARCH v7.0.1090 (Edgar, 2010), allowing zero mismatches and a minimum overlap of 50 bases. Merged reads were trimmed at first base with Q5. A quality filter was applied to the resulting merged reads. Reads containing above 0.05 expected errors were discarded. 16S rRNA gene sequences were clustered into Operational Taxonomic Units (OTUs) at a similarity cutoff value of 97% using the UPARSE algorithm (Edgar, 2013). OTUs were mapped to an optimized version of the SILVA Database (Quast et al., 2013) containing only the 16S v4 region to determine taxonomies. Abundances were recovered by mapping the demultiplexed reads to the UPARSE OTUs. A custom script constructed a rarefied OTU table from the output files generated in the previous two steps for downstream analyses of alpha-diversity, beta-diversity (Lozupone and Knight, 2005), and phylogenetic trends.

Whole Genome Shotgun Sequencing.

Individual libraries constructed from each sample were loaded onto the HiSeq platform (Illumina) and sequenced using the 2×100 bp pair-end read protocol. Illumina paired-end libraries were constructed from total genomic DNA isolated from each sample. The DNA was sheared into approximately 400-600 bp fragments followed by ligation of Illumina adaptors containing molecular barcodes for downstream de-multiplexing. These products were then amplified through ligation-mediated PCR (LM-PCR) using KAPA HiFi DNA Polymerase (Kapa Biosystems, Wilmington, Mass., USA). Following bead purification with Agencourt AMPure XP (Beckman Coulter, Brea, Calif., USA), quantification and size distribution of the LM-PCR product was determined using the LabChip GX electrophoresis system (PerkinElmer, Akron, Ohio, USA). Libraries were pooled in equimolar amounts at 6 samples per pool, and prepared for sequencing with TruSeq PE Cluster Generation Kit (Illumina). Each library pool was loaded onto one lane of a HiSeq 2000 flow cell spiked with 1% PhiX control library. Sequencing files were de-multiplexed with CASAVA version 1.8.3 (Illumina).

Quality filtering, trimming and de-multiplexing was carried out by a custom pipeline containing Trim Galore (Krueger, 2014) and cutadapt (Martin, 2011) for adapter and quality trimming, and PRINSEQ (Schmieder and Edwards, 2011) for low-complexity filtering and sequence deduplication. In addition, Bowtie2 v2.2.1 (Langmead and Salzberg, 2012) was used to map reads to MetaPhlAn markers for the classification of bacterial species (Segata et al., 2012).

Colonization of Germ-Free Mice by Fecal Microbiota Transplant.

Fresh fecal samples were collected from donor mice/microbiome cohort and homogenized on ice in sterile PBS under sterile conditions. The resulting slurry was spun at 1,000 g for three minutes at 4° C. The supernatants were isolated and diluted to $5 \times 10^9$ CFU/ml with sterile PBS. Four- or eight-week-old C57Bl6/J germ-free (GF) recipient mice were then immediately colonized by a single gavage with 0.2 mL solution. Fecal samples were collected from the colonized GF mice at 24 h, 7 d, 14 d, 28 d, and 56 d following colonization. Fecal samples were snap frozen and stored at −80° C. until prepared for sequencing. Behavioral experiments were initiated at three weeks post-transplant.

Culture and Treatment with L. reuteri and L. johnsonii.

Lactobacillus reuteri MM4-1A (ATCC-PTA-6475) and Lactobacillus johnsonii (ATCC 33200) were cultured anaerobically in MRS broth in a 90% $N_2$, 5% $CO_2$, 5% $H_2$ environment. L. reuteri was heat-killed by keeping the bacteria at 80° C. for 20 minutes (Wang et al., 2010). Bacterial viability was assessed by plating and the efficacy of the heat-kill procedure was confirmed by the absence of colony growth following plating. Cultures were centrifuged, washed, and resuspended in anaerobic solution (PBS) and frozen at −80° C. until use. PBS, live or heat-killed L. reuteri were added to the drinking water, which was changed daily to minimize dosage variability. Whereas the experimental group received live bacteria, one control group received identically prepared cultures of heat-killed bacteria. A second group of control mice received water treated with PBS alone. Live and heat-killed L. reuteri were supplied at a dosage of $1 \times 10^8$ organisms/mouse/day continuously in drinking water. Mice consumed the treated water ad libitum over the treatment period. The treated drinking water for each group was replaced daily two hours prior to the onset of the dark cycle to minimize variation in microbial exposure. Behavioral assays were initiated after 4-weeks of L. reuteri or control treatment. The protocol of the L. johnsonii preparation and administration matched the L. reuteri protocol. Fecal samples for sequencing and tissue used in the immunofluorescence studies were collected at the end of the treatment.

Immunofluorescence.

Mice were deeply anesthetized by inhalation of isoflurane and perfused transcardially with 10 ml 0.9% phosphate-buffered saline followed by 30 ml 4% paraformaldehyde in 0.1M phosphate buffer (PFA). Brains were post-fixed in 4% PFA at 4° C. overnight, then cryoprotected in 30% sucrose 0.1M PB over three days. Coronal slices (30 µm) thick were obtained from frozen tissue using a sliding blade microtome then transferred to ice cold PBS. Slices were blocked with 5% normal goat serum, 0.3% Triton X-100 0.1M PB (PBTgs) for 1 h rocking at RT and then incubated in primary antibodies (rabbit anti-oxytocin, ImmunoStar #20068, 1:2000; mouse anti-NeuN, Millipore, #MAB377, 1:2000) diluted in PBTgs rocking at 4° C. for 24 h. Slices were then washed three times with 0.3% Triton X-100 0.1M PB. Primary antibodies were visualized using secondary goat anti-rabbit Alexa Fluor® 488 (ThermoFisher Scientific, #A-11034) and goat anti-mouse Alexa Fluor® 594 (ThermoFisher Scientific, #A-11032) antibodies (1:1000 dilution). Slices were incubated in secondary antibodies rocking in the dark for 1 h at RT. Five minute final washes with each of PBTgs, 0.1M PB, and 0.05M PB preceded mounting onto 2% gelatin (Sigma-Aldrich, #G9391)-coated coverslips. Nuclei were visualized using Vectashield H-1200 with DAPI (Vector Labs, #H-1200). Fluorescent imaging and data acquisition was performed on a Zeiss AxioImager.Z2 microscope (Car Zeiss MicroImaging) mounted with an AxioCam digital camera (Carl Zeiss MicroImaging). Images were captured using AxioVision acquisition software (Carl Zeiss Microimaging). All images within a given data set were acquired at identical exposure times, within a given channel, to allow comparison of signal intensity. In some images, contrast and brightness were linearly adjusted using Photoshop (Adobe). Image processing was applied uniformly across all images within a given data set. Fluorescence intensity was measured in ImageJ (NIH) by selecting regions of interest (Oxytocin- and NeuN-positive hypothalamic cell bodies). Hypothalamic oxytocin-expressing neuronal population and NeuN+ cell number was assessed in ImageJ using the following operational sequence: (1) open image file, (2) subtract background, (3) adjust threshold, (4) convert to mask, (5) watershed, (6) analyze particles. Automatic identification of cell boundaries was validated against the source image by an experimenter blind to group allocation.

Oxytocin Administration.

Oxytocin was obtained from Tocris Bioscience (product 1910) and solubilized in 10% dimethyl sulfoxide (DMSO) in PBS. 10% DMSO in PBS was used as the vehicle control. Mice received oxytocin intranasally (at approximately 200 μg/kg) thirty minutes prior to behavior. 1.25 μl of oxytocin or vehicle solution was injected into each nostril from P10 pipette. Oxytocin dose was selected according to dosages reported to rescue social behavior in genetic models phenotypically expressing ASD-like behaviors (Penagarikano et al., 2015).

Electrophysiology.

Recordings were performed as previously described (Ungless et al., 2001; Zhu et al., 2011) and the investigators were kept blind to treatment conditions. Briefly, mice were anesthetized with a mixture of ketamine (100 mg/kg), xylazine (10 mg/kg) and acepromazine (3 mg/kg). Horizontal slices (225-300 μm thick) containing the VTA were cut from the brains of C57BL/6J mice. Mice were transcardially perfused with an ice-cold, oxygenated solution containing (in mM) NaCl, 87; NaHCO$_3$, 25; KCl, 2.5; NaH$_2$PO$_4$, 1.25; MgCl$_2$, 7; CaCl$_2$, 0.5; dextrose, 25; sucrose, 75. Horizontal slices were cut with a vibrating tissue slicer (VF-100 Compresstome, Precisionary Instruments, San Jose, Calif., or Leica VT 1000S, Leica Microsystems, Buffalo Grove, Ill.), incubated at 34° C. for 40 min, kept at room temperature for at least 30 min before their transfer to a recording chamber continuously perfused with artificial cerebrospinal fluid (ACSF) at 32° C. and a flow rate of 2-3 ml/min. The recording ACSF contained in mM: 120 NaCl, 3.3 KCl, 1.25 NaH$_2$PO$_4$, 25 NaHCO$_3$, 10 Dextrose, 1 MgCl$_2$ and 2 CaCl$_2$. Recording pipettes were made from thin-walled borosilicate glass (TW150E-4, WPI, Sarasota, Fla.). After filling with intracellular solution (in mM): 117 CsMeSO$_3$; 0.4 EGTA; 20 HEPES; 2.8 NaCl, 2.5 ATP-Mg 2.0; 0.25 GTP-Na; 5 TEA-Cl, adjusted to pH 7.3 with CsOH and 290 mosmol/l, they had a resistance of 3-5 MΩ. Data were obtained with a MultiClamp 700B amplifier, digitized at 20 kHz with a Digidata 1440A, recorded by Clampex 10 and analyzed with Clampfit 10 software (Molecular Devices). Recordings were filtered online at 3 kHz with a Bessel low-pass filter. A 2 mV hyperpolarizing pulse was applied before each EPSC to evaluate the input and access resistance (Ra). Data were discarded when Ra was either unstable or greater than 25 MΩ, holding current was >200 pA, input resistance dropped >20% during the recording, or EPSCs baseline changed by >10%. After establishing a gigaohm seal (>2 GΩ) and recording stable spontaneous firing in cell-attached, voltage clamp mode (−70 mV holding potential), cell phenotype was determined by measuring the width of the action potential and the presence of an Ih current. AMPAR/NMDAR ratios were calculated as previously described (Ungless et al., 2001). Briefly, neurons were voltage-clamped at +40 mV until the holding current stabilized (at <200 pA). Monosynaptic EPSCs were evoked at 0.05 Hz with a bipolar stimulating electrode placed 50-150 μm rostral to the lateral VTA. Picrotoxin (100 μM) was added to the recording ACSF to block GABARA-mediated IPSCs. After recording the dual-component EPSC, DL-AP5 (100 μM) was bath-applied for 10 min to remove the NMDAR component, which was then obtained by offline subtraction of the remaining AMPAR component from the original EPSC. The peak amplitudes of the isolated components were used to calculate the AMPAR/NMDAR ratios. Picrotoxin and DL-AP5 were purchased from Tocris Bioscience and all other reagents were obtained from Sigma-Aldrich.

Statistical Analysis.

Data are presented as mean±SEM. For behavioral experiments, statistics were based on the two-sided unpaired Student's t-tests, one- or two-way ANOVA with Bonferroni post-hoc analysis to correct for multiple comparisons, unless otherwise indicated. P, t, and F values are presented in the figure legends, n values are provided in the figures. $P<0.05$ was considered significant. $*P<0.05$, $P<0.01$, $*P<0.001$, $****P<0.0001$. GraphPad's Prism 6 (La Jolla, Calif.) software was used to perform statistical analyses and for generating graphical representations of data. For 16S rRNA gene sequencing, analysis and visualization of microbiome communities was conducted in RStudio 0.99.292 [http://www.R-project.org/ (2014)], utilizing the phyloseq package (McMurdie and Holmes, 2013) to import sample data and calculate alpha- and beta-diversity metrics. 16S rRNA gene sequencing data was analyzed using Silva 115 and 123 (Quast et al., 2013). Analyses were performed on datasets that were rarefied 1,000×, then averaged and rounded. Amplicon sequences were deposited to the NCBI Sequence Read Archive under accession number TBD. Dirichlet Multinomial Mixture modeling was performed in mother (Schloss et al., 2009). Significance of categorical variables were determined using the non-parametric Mann-Whitney test for two category comparisons or the Kruskal-Wallis test when comparing three or more categories. One-way ANOVA followed by Dunnett's multiple comparisons test was performed using GraphPad's Prism 6. Correlation between two continuous variables was determined by linear regressions, where P-values indicate the probability that the slope of the regression line is zero. Principal coordinate plots employed the Monte Carlo permutation test to estimate P-values. All P-values were adjusted for multiple comparisons with the FDR algorithm (Benjamini et al., 2001). Sample size was based on published literature (Argilli et al., 2008; Caporaso et al., 2012; Chung et al., 2015; Gkogkas et al., 2013). No animals or data points were excluded from analyses.

Example 3

Figure 23A:
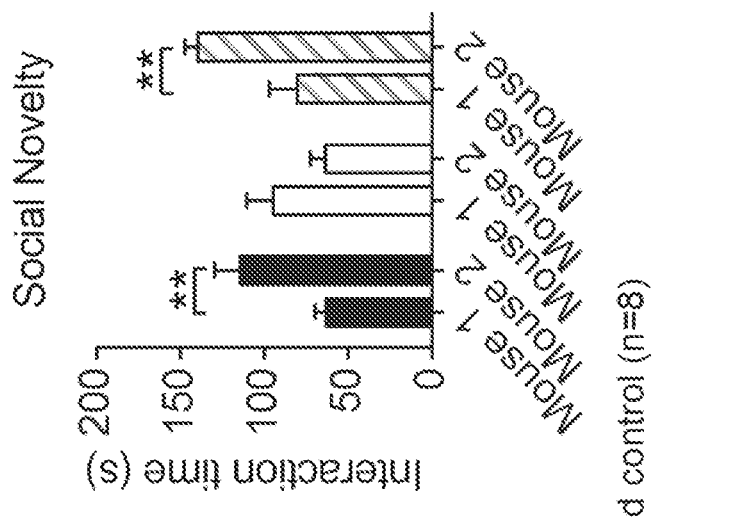
FIGS. 23A and 23B: Treatment with *L. reuteri* rescues social behavioral deficits in GF mice. Addition of *L. reuteri* into the drinking water reverses the deficient sociability (FIG. 23A) and social novelty (FIG. 23B) of GF mice.
Figure 23B:
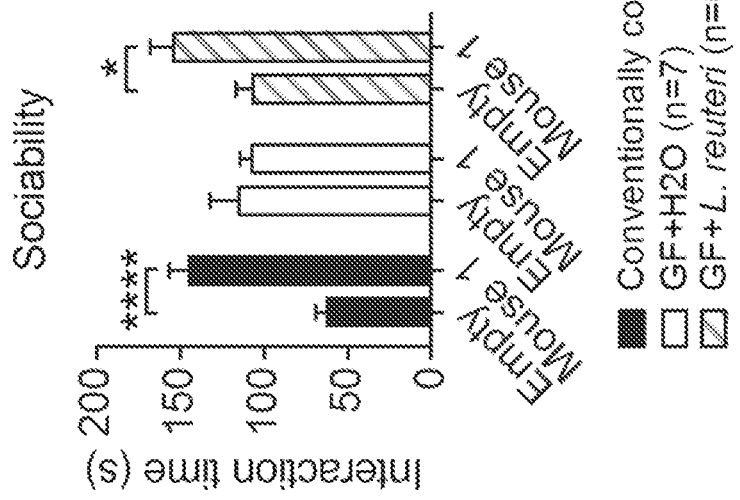

L. reuteri Treatment Restores Social Behaviors in Genetic and Environmental Models of ASD A. Treatment with L. reuteri rescues social behavior in germ-free mice. We have previously shown that treatment with *L. reuteri* reverses social behavioral deficits in MHFD mice. However, whether one species (*L. reuteri*) alone is directly responsible for restoring the social behavioral phenotype in MHFD offspring or whether the effect of *L. reuteri* is indirect by altering or changing the activity and/or the bacterial ecosystem which are responsible for the resulting biological change in behavior is currently unknown. To distinguish between these two possibilities, we treated germ-free (GF) mice with *L. reuteri*, as we described above. Consistent with our previous results, compared to conventionally colonized mice, GF mice show impaired social behaviors (FIG. 23A). Interestingly, treatment with *L. reuteri* was sufficient to restore the social behavior deficits in GF mice (FIGS. 23A-23B). Since GF mice by definition are devoid of any bacteria or microbes, our data suggest that the effect of *L. reuteri* on social behavior is direct (not mediated by another bacteria or microbe). Thus, treatment with *L. reuteri* restores social behaviors in both MHFD offspring and GF mice.

B. Treatment with *L. reuteri* Rescues Social Behaviors in a Genetic Mouse Model of ASD.

To examine whether treatment with *L. reuteri* could restore ASD-like behaviors in genetic models of ASD, we studied mice lacking contactin associated protein-like 2 (CNTNAP2). Mutations in CNTNAP2 have been associated with syndromic forms of ASD (Nascimento, et al., 2016; Yoo, et al., 2017; Zare, et al., 2017; el-Sobky, et al., 2004; Alarcon, et al., 2008; Sampath, et al., 2013; Chiocchetti, et al., 2015), thereby serving as a genetic model of autism in mice. Second, mice lacking Cntnap2 show ASD-like behaviors (Penagarikano, et al.). Third, oxytocin rescues the social behavioral abnormalities in mice lacking Cntnap2 (Penagarikano, et al., 2015; Penagarikano, et al., 2011). As previously described (Penagarikano, et al., 2015; Penagarikano, et al., 2011), we also found that mice lacking CNTNAP2 show deficit social behavior, as demonstrated by the impaired sociability and social novelty (FIGS. 24A-24B. Remarkably, we found that treatment with *L. reuteri* reverses the social behavior abnormalities in Cntnap2-deficient mice (FIGS. 24C-24D).

In summary, we have shown that a) oxytocin restores social behavior in Cntnap2-deficient mice and b) *L. reuteri* promotes oxytocin production in the PVN and rescues social behaviors in MHFD offspring, and c) *L. reuteri* reverses the social behaviors in a genetic mouse model of ASD. Taken together, our data support the notion that treatment with *L. reuteri* rescues social behaviors in environmental (MHFD offspring and GF mice) and genetic (Cntnap2-deficient mice) models of ASD, and taken together with our previous descriptions of the relationships between social dysfunction, oxytocin levels and many other neurological conditions, the use of *L. reuteri* therapy may be considered a more general therapeutic approach if dosed and delivered (live bacteria or specially prepared extracts or lysates) in an effective manner.

Example 4

Treatment of Prevention of Neurodevelopmental, Neurodegenerative, and Psychiatric Disorders In particular embodiments, the present disclosure concerns neurodevelopmental and psychiatric disorders: In addition to neurodevelopmental disorders, the present disclosure includes medical conditions in which the oxytocinergic system is dysfunctional, including Williams Syndrome, Prader-Willi syndrome and Fragile X syndrome, for example (Francis, et al., 2014). Moreover, in particular embodiments targeting the oxytocin system via *L. reuteri* administration is useful to treat addictive behaviors, including eating/feeding disorders, drug addiction, bipolar disorder and Schizophrenia, for example (Cochran, et al., 2013; MacDonald, et al., 2014; McQuaid, et al., 2014; Sarnyai, et al., 2014; Kirsch, et al., 2015; Perez-Rodriguez, et al., 2015; Rice, et al., 2015; Romano, et al., 2015; Zik, et al., 2015; Brambilla, et al., 2016; Bukovskaya, et al., 2016; Lee, et al., 2016; Quintana, et al., 2017).

In specific embodiments, an effective amount of *L. reuteri* is provided to an individual with or at risk for depression. Depression is one of the most common psychiatric disorders. It causes severe symptoms that affect how one feels, thinks, and handles daily activities, such as sleeping, eating, or working. Interestingly, decreased oxytocin levels might increase the risk of depression, in particular postpartum depression (McQuaid, et al., 2014; Arletti, et al., 1987; Papp, et al., 2000; Matsushita, et al., 2010; Loyens, et al., 2013; Moura, et al., 2016; Amini-Khoei, et al., 2017). Given that *L. reuteri* promotes the production of oxytocin, *L. reuteri* in particular embodiments is useful in the treatment of major depressive disorders.

In particular embodiments, drug addiction, Parkinson's disease, and compulsive disorders with alteration in the reward-dopamine system. The inventors have shown that *L. reuteri* promotes the activity of dopaminergic neurons in a key reward area. In addiction, where there is compulsive behavior that is reinforcing (rewarding) and there is a loss of control in limiting intake, reward dopaminergic pathways are altered. In specific embodiments, *L. reuteri* is useful for the treatment of conditions in which the dopaminergic and reward system are usurped, including drug addiction (Hyman, et al., 2006), obesity and food intake (Kenny, et al., 2011; Blum, et al., 2014), Parkinson's disease and other addictive behaviors, such as gambling (Fenu, et al., 2009; Matsumoto, et al., 2015), for example.

In certain embodiments, the present disclosure improves social cognitive function, such as with neurodegenerative disorders. Social cognitive impairment, which can lead to poor quality of life, mental health problems and loneliness (Kennedy, et al., 2012), can be prominent after acute brain damage (for example), such as traumatic brain injury or stroke, and in specific embodiments represents a core feature of the early stages of some chronic neurological disorders, such as frontotemporal dementia, Alzheimer's disease and Parkinson's disease (Beer, et al., 2006; Henry, et al., 2016). In addition, oxytocin and dopamine are crucial for the formation of social memory (Ferguson, et al., 2000; Gonzalez-Burgos, et al., 2008; Shamay-Tsoory, et al., 2016). Because the inventors determined that *L. reuteri* promotes oxytocin production and dopamine-mediated synaptic plasticity, two systems that are hijacked in disorders exhibiting social cognition problems (Rudelli, et al., 1984; Gibb, et al., 1989; Braak, et al., 1990; Selden, et al., 1994; Burns, et al., 2005; Ross, et al., 2009; Borroni, et al., 2010; Finger, et al., 2011; Tampi, et al., 2017), this bacteria species is useful for the treatment of social memory and cognitive function in neurological and neurodegenerative disorders.

Treatment with *L. reuteri* Rescues Social Behavior in Germ-Free Mice.

The inventors have previously shown that treatment with *L. reuteri* reverses social behavioral deficits in MHFD mice. However, whether one species (*L. reuteri*) alone is directly responsible for restoring the social behavioral phenotype in MHFD offspring or whether the effect of *L. reuteri* is indirect by altering or changing the activity and/or the bacterial ecosystem which are responsible for the resulting biological change in behavior is currently unknown. To distinguish between these two possibilities, the inventors treated germ-free (GF) mice with *L. reuteri*, as we described above. Consistent with our previous results, compared to conventionally colonized mice, GF mice show impaired social behaviors (FIGS. 23A-23B). Interestingly, treatment with *L. reuteri* was sufficient to restore the social behavior deficits in GF mice (FIGS. 23A-23B). Since GF mice by definition are devoid of any bacteria or microbes, our data suggest that the effect of *L. reuteri* on social behavior is direct (not mediated by another bacteria or microbe). Thus, treatment with *L. reuteri* restores social behaviors in both MHFD offspring and GF mice.

Treatment with *L. reuteri* Rescues Social Behaviors in a Genetic Mouse Model of ASD.

To examine whether treatment with *L. reuteri* could restore ASD-like behaviors in genetic models of ASD, the inventors studied mice lacking contactin associated protein-like 2 (CNTNAP2). Mutations in CNTNAP2 have been associated with syndromic forms of ASD (Nascimento et al., 2016; Yoo et al., 2017; Zare et al., 2017; el-Sobky et al., 2004; Alarcon et al., 2008; Sampath et al., 2013; Chiocchetti et al., 2015), thereby serving as a genetic model of autism in mice. Second, mice lacking Cntnap2 show ASD-like behaviors (Penagarikano et al., 2015). Third, oxytocin rescues the social behavioral abnormalities in mice lacking Cntnap2 (Penagarikano et al., 2015; Penagarikano et al., 2011). As previously described (Penagarikano et al., 2015; Penagarikano et al., 2011), mice lacking CNTNAP2 show deficit social behavior, as demonstrated by the impaired sociability and social novelty (FIGS. 24A-24B). Remarkably, treatment with *L. reuteri* reverses the social behavior abnormalities in Cntnap2-deficient mice (FIGS. 24C-24D).

In summary, we have shown that a) oxytocin restores social behavior in Cntnap2-deficient mice and b) *L. reuteri* promotes oxytocin production in the PVN and rescues social behaviors in MHFD offspring, and c) *L. reuteri* reverses the social behaviors in a genetic mouse model of ASD. Taken together, our data support the notion that treatment with *L. reuteri* rescues social behaviors in environmental (MHFD offspring and GF mice) and genetic (Cntnap2-deficient mice) models of ASD, and taken together with our previous descriptions of the relationships between social dysfunction, oxytocin levels and many other neurological conditions, the use of *L. reuteri* therapy may be considered a more general therapeutic approach if dosed and delivered (live bacteria or specially prepared extracts or lysates) in an effective manner.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

Alarcon, M., et al., Linkage, association, and gene-expression analyses identify CNTNAP2 as an autism-susceptibility gene. Am J Hum Genet, 2008. 82(1): p. 150-9.

Amini-Khoei, H., et al., Oxytocin mitigated the depressive-like behaviors of maternal separation stress through modulating mitochondrial function and neuroinflammation. Prog Neuropsychopharmacol Biol Psychiatry, 2017. 76: p. 169-178.

Argilli, E., Sibley, D. R., Malenka, R. C., England, P. M., and Bonci, A. (2008). Mechanism and time course of cocaine-induced long-term potentiation in the ventral tegmental area. The Journal of neuroscience: the official journal of the Society for Neuroscience 28, 9092-9100.

Arletti, R. and A. Bertolini, Oxytocin acts as an antidepressant in two animal models of depression. Life Sci, 1987. 41(14): p. 1725-30.

Aye, I. L., Rosario, F. J., Powell, T. L., and Jansson, T. (2015). Adiponectin supplementation in pregnant mice prevents the adverse effects of maternal obesity on placental function and fetal growth. Proceedings of the National Academy of Sciences of the United States of America 112, 12858-12863.

Beer, J. S. and K. N. Ochsner, Social cognition: a multi level analysis. Brain Res, 2006. 1079(1): p. 98-105.

Benjamini, Y., Drai, D., Elmer, G., Kafkafi, N., and Golani, I. (2001). Controlling the false discovery rate in behavior genetics research. Behavioural brain research 125, 279-284.

Bilder, D. A., Bakian, A. V., Viskochil, J., Clark, E. A., Botts, E. L., Smith, K. R., Pimentel, R., McMahon, W. M., and Coon, H. (2013). Maternal prenatal weight gain and autism spectrum disorders. Pediatrics 132, e1276-1283.

Blum, K., P. K. Thanos, and M. S. Gold, Dopamine and glucose, obesity, and reward deficiency syndrome. Front Psychol, 2014. 5: p. 919.

Bolton, J. L., and Bilbo, S. D. (2014). Developmental programming of brain and behavior by perinatal diet: focus on inflammatory mechanisms. Dialogues in clinical neuroscience 16, 307-320.

Borroni, B., C. Costanzi, and A. Padovani, Genetic susceptibility to behavioural and psychological symptoms in Alzheimer disease. Curr Alzheimer Res, 2010. 7(2): p. 158-64.

Braak, H. and E. Braak, Alzheimer's disease: striatal amyloid deposits and neurofibrillary changes. J Neuropathol Exp Neurol, 1990. 49(3): p. 215-24.

Brambilla, M., et al., Effects of Intranasal Oxytocin on Long-Term Memory in Healthy Humans: A Systematic Review. Drug Dev Res, 2016. 77(8): p. 479-488.

Bravo, J. A., Forsythe, P., Chew, M. V., Escaravage, E., Savignac, H. M., Dinan, T. G., Bienenstock, J., and Cryan, J. F. (2011). Ingestion of *Lactobacillus* strain regulates emotional behavior and central GABA receptor expression in a mouse via the vagus nerve. Proceedings of the National Academy of Sciences of the United States of America 108, 16050-16055.

Bukovskaya, O. and A. Shmukler, Oxytocin and Social Cognitions in Schizophrenia: A Systematic Review. Psychiatr Q, 2016. 87(3): p. 521-43.

Burns, J. M., et al., White matter lesions are prevalent but differentially related with cognition in aging and early Alzheimer disease. Arch Neurol, 2005. 62(12): p. 1870-6.

Caporaso, J. G., Lauber, C. L., Walters, W. A., Berg-Lyons, D., Huntley, J., Fierer, N., Owens, S. M., Betley, J., Fraser, L., Bauer, M., et al. (2012). Ultra-high-throughput microbial community analysis on the Illumina HiSeq and MiSeq platforms. The ISME journal 6, 1621-1624.

Chiocchetti, A. G., et al., Variants of the CNTNAP2 5' promoter as risk factors for autism spectrum disorders: a genetic and functional approach. Mol Psychiatry, 2015. 20(7): p. 839-49.

Chung, W., Choi, S. Y., Lee, E., Park, H., Kang, J., Park, H., Choi, Y., Lee, D., Park, S. G., Kim, R., et al. (2015). Social deficits in IRSp53 mutant mice improved by NMDAR and mGluR5 suppression. Nature neuroscience 18, 435-443.

Cochran, D. M., et al., The role of oxytocin in psychiatric disorders: a review of biological and therapeutic research findings. Harv Rev Psychiatry, 2013. 21(5): p. 219-47.

Connolly, N., Anixt, J., Manning, P., Ping, I. L. D., Marsolo, K. A., and Bowers, K. (2016). Maternal metabolic risk factors for autism spectrum disorder—An analysis of electronic medical records and linked birth data. Autism research: official journal of the International Society for Autism Research.

Cryan, J. F., and Dinan, T. G. (2012). Mind-altering microorganisms: the impact of the gut microbiota on brain and behaviour. Nature reviews Neuroscience 13, 701-712.

Davari, S., Talaei, S. A., Alaei, H., and Salami, M. (2013). Probiotics treatment improves diabetes-induced impairment of synaptic activity and cognitive function: behavioral and electrophysiological proofs for microbiome-gut-brain axis. Neuroscience 240, 287-296.

Dodds, L., Fell, D. B., Shea, S., Armson, B. A., Allen, A. C., and Bryson, S. (2011). The role of prenatal, obstetric and neonatal factors in the development of autism. Journal of autism and developmental disorders 41, 891-902.

Dolen, G., Darvishzadeh, A., Huang, K. W., and Malenka, R. C. (2013). Social reward requires coordinated activity of nucleus accumbens oxytocin and serotonin. Nature 501, 179-184.

Donaldson, Z. R., and Young, L. J. (2008). Oxytocin, vasopressin, and the neurogenetics of sociality. Science 322, 900-904.

Edgar, R. C. (2010). Search and clustering orders of magnitude faster than BLAST. Bioinformatics 26, 2460-2461.

Edgar, R. C. (2013). UPARSE: highly accurate OTU sequences from microbial amplicon reads. Nature methods 10, 996-998.

el-Sobky, E., et al., Molecular cytogentic profiles of hepatitis C infection in patients at Sharkia Governorate, Egypt. J Egypt Soc Parasitol, 2004. 34(1 Suppl): p. 401-15.

Fenu, S., J. Wardas, and M. Morelli, Impulse control disorders and dopamine dysregulation syndrome associated with dopamine agonist therapy in Parkinson's disease. Behav Pharmacol, 2009. 20(5-6): p. 363-79.

Ferguson, J. N., et al., Social amnesia in mice lacking the oxytocin gene. Nat Genet, 2000. 25(3): p. 284-8.

Finger, E. C., New potential therapeutic approaches in frontotemporal dementia: oxytocin, vasopressin, and social cognition. J Mol Neurosci, 2011. 45(3): p. 696-701.

Foster, J. A., and McVey Neufeld, K. A. (2013). Gut-brain axis: how the microbiome influences anxiety and depression. Trends in neurosciences 36, 305-312.

Francis, S. M., et al., Oxytocin and vasopressin systems in genetic syndromes and neurodevelopmental disorders. Brain Res, 2014. 1580: p. 199-218.

Frese, S. A, et al., The evolution of host specialization in the vertebrate gut symbiont Lactobacillus reuteri. PLoS Genet. 2011 February; 7(2):e1001314. doi: 10.1371/journal.pgen.1001314.

Galley, J. D., Bailey, M., Kamp Dush, C., Schoppe-Sullivan, S., and Christian, L. M. (2014). Maternal obesity is associated with alterations in the gut microbiome in toddlers. PloS one 9, e113026.

Gibb, W. R., et al., The substantia nigra and ventral tegmental area in Alzheimer's disease and Down's syndrome. J Neurol Neurosurg Psychiatry, 1989. 52(2): p. 193-200.

Gkogkas, C. G., Khoutorsky, A., Ran, I., Rampakakis, E., Nevarko, T., Weatherill, D. B., Vasuta, C., Yee, S., Truitt, M., Dallaire, P., et al. (2013). Autism-related deficits via dysregulated eIF4E-dependent translational control. Nature 493, 371-377.

Gonzalez-Burgos, I. and A. Feria-Velasco, Serotonin/dopamine interaction in memory formation. Prog Brain Res, 2008. 172: p. 603-23.

Gregory, R., Cheng, H., Rupp, H. A., Sengelaub, D. R., and Heiman, J. R. (2015). Oxytocin increases VTA activation to infant and sexual stimuli in nulliparous and postpartum women. Hormones and behavior 69, 82-88.

Groppe, S. E., Gossen, A., Rademacher, L., Hahn, A., Westphal, L., Grunder, G., and Spreckelmeyer, K. N. (2013). Oxytocin influences processing of socially relevant cues in the ventral tegmental area of the human brain. Biological psychiatry 74, 172-179.

Gunaydin, L. A., Grosenick, L., Finkelstein, J. C., Kauvar, I. V., Fenno, L. E., Adhikari, A., Lammel, S., Mirzabekov, J. J., Airan, R. D., Zalocusky, K. A., et al. (2014). Natural neural projection dynamics underlying social behavior. Cell 157, 1535-1551.

Hallmayer, J., Cleveland, S., Torres, A., Phillips, J., Cohen, B., Torigoe, T., Miller, J., Fedele, A., Collins, J., Smith, K., et al. (2011). Genetic heritability and shared environmental factors among twin pairs with autism. Archives of general psychiatry 68, 1095-1102.

Henry, J. D., et al., Clinical assessment of social cognitive function in neurological disorders. Nat Rev Neurol, 2016. 12(1): p. 28-39.

Hsiao, E. Y., McBride, S. W., Hsien, S., Sharon, G., Hyde, E. R., McCue, T., Codelli, J. A., Chow, J., Reisman, S. E., Petrosino, J. F., et al. (2013). Microbiota modulate behavioral and physiological abnormalities associated with neurodevelopmental disorders. Cell 155, 1451-1463.

Huang, Y. C., and Hessler, N. A. (2008). Social modulation during songbird courtship potentiates midbrain dopaminergic neurons. PloS one 3, e3281.

Human Microbiome Project, C. (2012a). A framework for human microbiome research. Nature 486, 215-221.

Human Microbiome Project, C. (2012b). Structure, function and diversity of the healthy human microbiome. Nature 486, 207-214.

Hyman, S. E., R. C. Malenka, and E. J. Nestler, Neural mechanisms of addiction: the role of reward-related learning and memory. Annu Rev Neurosci, 2006. 29: p. 565-98.

Insel, T. R. (2010). The challenge of translation in social neuroscience: a review of oxytocin, vasopressin, and affiliative behavior. Neuron 65, 768-779.

Kennedy, D. P. and R. Adolphs, The social brain in psychiatric and neurological disorders. Trends Cogn Sci, 2012. 16(11): p. 559-72.

Kenny, P. J., Common cellular and molecular mechanisms in obesity and drug addiction. Nat Rev Neurosci, 2011. 12(11): p. 638-51.

King, J. C. (2006). Maternal obesity, metabolism, and pregnancy outcomes. Annual review of nutrition 26, 271-291.

Kirsch, P., Oxytocin in the socioemotional brain: implications for psychiatric disorders. Dialogues Clin Neurosci, 2015. 17(4): p. 463-76.

Kohane, I. S., McMurry, A., Weber, G., MacFadden, D., Rappaport, L., Kunkel, L., Bickel, J., Wattanasin, N., Spence, S., Murphy, S., et al. (2012). The co-morbidity burden of children and young adults with autism spectrum disorders. PloS one 7, e33224.

Krakowiak, P., Walker, C. K., Bremer, A. A., Baker, A. S., Ozonoff, S., Hansen, R. L., and Hertz-Picciotto, I. (2012). Maternal metabolic conditions and risk for autism and other neurodevelopmental disorders. Pediatrics 129, e1121-1128.

Krueger, F. (2014). Trim Galore. v.0.3.7. http://wwwbioinformaticsbabrahamacuk/projects/trim_galore/.

Langmead, B., and Salzberg, S. L. (2012). Fast gapped-read alignment with Bowtie 2. Nature methods 9, 357-359.

Lee, M. R., et al., Targeting the Oxytocin System to Treat Addictive Disorders: Rationale and Progress to Date. CNS Drugs, 2016. 30(2): p. 109-23.

Lerer, E., Levi, S., Salomon, S., Darvasi, A., Yirmiya, N., and Ebstein, R. P. (2008). Association between the oxytocin receptor (OXTR) gene and autism: relationship to Vineland Adaptive Behavior Scales and cognition. Molecular psychiatry 13, 980-988.

Loyens, E., et al., Antidepressant-like effects of oxytocin in mice are dependent on the presence of insulin-regulated aminopeptidase. Int J Neuropsychopharmacol, 2013. 16(5): p. 1153-63.

Lozupone, C., and Knight, R. (2005). UniFrac: a new phylogenetic method for comparing microbial communities. Applied and environmental microbiology 71, 8228-8235.

Ma, J., Prince, A. L., Bader, D., Hu, M., Ganu, R., Baquero, K., Blundell, P., Alan Harris, R., Frias, A. E., Grove, K. L., et al. (2014). High-fat maternal diet during pregnancy persistently alters the offspring microbiome in a primate model. Nature communications 5, 3889.

MacDonald, K. and D. Feifel, Oxytocin's role in anxiety: a critical appraisal. Brain Res, 2014. 1580: p. 22-56.

Martin, M. (2011). Cutadapt removes adaptor sequences from high-throughput sequencing reads. EMBnetjournal 17, 10-12.

Mathers, J. C., and McKay, J. A. (2009). Epigenetics—potential contribution to fetal programming. Advances in experimental medicine and biology 646, 119-123.

Matsumoto, M., Dopamine signals and physiological origin of cognitive dysfunction in Parkinson's disease. Mov Disord, 2015. 30(4): p. 472-83.

Matsushita, H., et al., Oxytocin mediates the antidepressant effects of mating behavior in male mice. Neurosci Res, 2010. 68(2): p. 151-3.

Matsuzaki, M., et al., Oxytocin: a therapeutic target for mental disorders. J Physiol Sci, 2012. 62(6): p. 441-4.

Mayer, E. A., Padua, D., and Tillisch, K. (2014). Altered brain-gut axis in autism: comorbidity or causative mechanisms? BioEssays: news and reviews in molecular, cellular and developmental biology 36, 933-939.

Mayer, E. A., Tillisch, K., and Gupta, A. (2015). Gut/brain axis and the microbiota. The Journal of clinical investigation 125, 926-938.

McMurdie, P. J., and Holmes, S. (2013). phyloseq: an R package for reproducible interactive analysis and graphics of microbiome census data. PloS one 8, e61217.

McQuaid, R. J., et al., Making room for oxytocin in understanding depression. Neurosci Biobehav Rev, 2014. 45: p. 305-22.

Mefford, H. C., Batshaw, M. L., and Hoffman, E. P. (2012). Genomics, intellectual disability, and autism. N Engl J Med 366, 733-743.

Melis, M. R., Melis, T., Cocco, C., Succu, S., Sanna, F., Pillolla, G., Boi, A., Ferri, G. L., and Argiolas, A. (2007). Oxytocin injected into the ventral tegmental area induces penile erection and increases extracellular dopamine in the nucleus accumbens and paraventricular nucleus of the hypothalamus of male rats. The European journal of neuroscience 26, 1026-1035.

Modi, M. E., and Young, L. J. (2012). The oxytocin system in drug discovery for autism: animal models and novel therapeutic strategies. Hormones and behavior 61, 340-350.

Moss, B. G., and Chugani, D. C. (2014). Increased risk of very low birth weight, rapid postnatal growth, and autism in underweight and obese mothers. American journal of health promotion: AJHP 28, 181-188.

Moura, D., M. C. Canavarro, and M. Figueiredo-Braga, Oxytocin and depression in the perinatal period—a systematic review. Arch Womens Ment Health, 2016. 19(4): p. 561-70.

Nascimento, P. P., et al., Single nucleotide polymorphisms in the CNTNAP2 gene in Brazilian patients with autistic spectrum disorder. Genet Mol Res, 2016. 15(1).

Ogden, C. L., Carroll, M. D., Kit, B. K., and Flegal, K. M. (2014). Prevalence of childhood and adult obesity in the United States, 2011-2012. JAMA: the journal of the American Medical Association 311, 806-814.

Oh P. L et al., Diversification of the gut symbiont *Lactobacillus reuteri* as a result of host-driven evolution. ISME J. 2010 March; 4(3):377-87.

Papp, M. and J. Wieronska, Antidepressant-like activity of amisulpride in two animal models of depression. J Psychopharmacol, 2000. 14(1): p. 46-52.

Parracho, H. M., Bingham, M. O., Gibson, G. R., and McCartney, A. L. (2005). Differences between the gut microflora of children with autistic spectrum disorders and that of healthy children. Journal of medical microbiology 54, 987-991.

Pedersen, C. A., Caldwell, J. D., Walker, C., Ayers, G., and Mason, G. A. (1994). Oxytocin activates the postpartum onset of rat maternal behavior in the ventral tegmental and medial preoptic areas. Behavioral neuroscience 108, 1163-1171.

Penagarikano, O., et al., Absence of CNTNAP2 leads to epilepsy, neuronal migration abnormalities, and core autism-related deficits. Cell, 2011. 147(1): p. 235-46.

Penagarikano, O., et al., Exogenous and evoked oxytocin restores social behavior in the Cntnap2 mouse model of autism. Sci Transl Med, 2015. 7(271): p. 271ra8.

Perez-Rodriguez, M., et al., Oxytocin and social cognition in affective and psychotic disorders. Eur Neuropsychopharmacol, 2015. 25(2): p. 265-82.

Poutahidis, T., Kearney, S. M., Levkovich, T., Qi, P., Varian, B. J., Lakritz, J. R., Ibrahim, Y. M., Chatzigiagkos, A., Alm, E. J., and Erdman, S. E. (2013). Microbial symbionts accelerate wound healing via the neuropeptide hormone oxytocin. PloS one 8, e78898.

Quast, C., Pruesse, E., Yilmaz, P., Gerken, J., Schweer, T., Yarza, P., Peplies, J., and Glockner, F. O. (2013). The SILVA ribosomal RNA gene database project: improved data processing and web-based tools. Nucleic acids research 41, D590-596.

Quintana, D. S., et al., Oxytocin system dysfunction as a common mechanism underlying metabolic syndrome and psychiatric symptoms in schizophrenia and bipolar disorders. Front Neuroendocrinol, 2017.

Rice, L. J. and S. L. Einfeld, Cognitive and behavioural aspects of Prader-Willi syndrome. Curr Opin Psychiatry, 2015. 28(2): p. 102-6.

Ridaura, V. K., Faith, J. J., Rey, F. E., Cheng, J., Duncan, A. E., Kau, A. L., Griffin, N. W., Lombard, V., Henrissat, B., Bain, J. R., et al. (2013). Gut microbiota from twins discordant for obesity modulate metabolism in mice. Science 341, 1241214.

Romano, A., et al., From Autism to Eating Disorders and More: The Role of Oxytocin in Neuropsychiatric Disorders. Front Neurosci, 2015. 9: p. 497.

Ross, H. E. and L. J. Young, Oxytocin and the neural mechanisms regulating social cognition and affiliative behavior. Front Neuroendocrinol, 2009. 30(4): p. 534-47.

Rudelli, R. D., M. W. Ambler, and H. M. Wisniewski, Morphology and distribution of Alzheimer neuritic (senile) and amyloid plaques in striatum and diencephalon. Acta Neuropathol, 1984. 64(4): p. 273-81.

Sabatier, N., Leng, G., and Menzies, J. (2013). Oxytocin, feeding, and satiety. Frontiers in endocrinology 4, 35.

Sampath, S., et al., Defining the contribution of CNTNAP2 to autism susceptibility. PLoS One, 2013. 8(10): p. e77906.

Sarnyai, Z. and G. L. Kovacs, Oxytocin in learning and addiction: From early discoveries to the present. Pharmacol Biochem Behav, 2014. 119: p. 3-9.

Schloss, P. D., Westcott, S. L., Ryabin, T., Hall, J. R., Hartmann, M., Hollister, E. B., Lesniewski, R. A., Oakley, B. B., Parks, D. H., Robinson, C. J., et al. (2009). Introducing mothur: open-source, platform-independent, community-supported software for describing and comparing microbial communities. Applied and environmental microbiology 75, 7537-7541.

Schmieder, R., and Edwards, R. (2011). Quality control and preprocessing of metagenomic datasets. Bioinformatics 27, 863-864.

Segata, N., Waldron, L., Ballarini, A., Narasimhan, V., Jousson, O., and Huttenhower, C. (2012). Metagenomic microbial community profiling using unique clade-specific marker genes. Nature methods 9, 811-814.

Selden, N., M. M. Mesulam, and C. Geula, Human striatum: the distribution of neurofibrillary tangles in Alzheimer's disease. Brain Res, 1994. 648(2): p. 327-31.

Shamay-Tsoory, S. G. and A. Abu-Akel, The Social Salience Hypothesis of Oxytocin. Biol Psychiatry, 2016. 79(3): p. 194-202.

Silverman, J. L., Yang, M., Lord, C., and Crawley, J. N. (2010). Behavioural phenotyping assays for mouse models of autism. Nature reviews Neuroscience 11, 490-502.

Skinner, A. C., and Skelton, J. A. (2014). Prevalence and trends in obesity and severe obesity among children in the United States, 1999-2012. JAMA pediatrics 168, 561-566.

Song, S. J., Lauber, C., Costello, E. K., Lozupone, C. A., Humphrey, G., Berg-Lyons, D., Caporaso, J. G., Knights, D., Clemente, J. C., Nakielny, S., et al. (2013). Cohabiting family members share microbiota with one another and with their dogs. eLife 2, e00458.

Spinler, J. K., et al. From prediction to function using evolutionary genomics: human-specific ecotypes of *Lactobacillus reuteri* have diverse probiotic functions. Genome Biol Evol. 2014 Jun. 19; 6(7):1772-89. doi: 10.1093/gbe/evu137.

Sullivan, E. L., Nousen, E. K., and Chamlou, K. A. (2014). Maternal high fat diet consumption during the perinatal period programs offspring behavior. Physiology & behavior 123, 236-242.

Tampi, R. R., et al., Oxytocin for frontotemporal dementia: a systematic review. Ther Adv Psychopharmacol, 2017. 7(1): p. 48-53.

Tang, Y., Chen, Z., Tao, H., Li, C., Zhang, X., Tang, A., and Liu, Y. (2014). Oxytocin activation of neurons in ventral tegmental area and interfascicular nucleus of mouse midbrain. Neuropharmacology 77, 277-284.

Thomas, A., Burant, A., Bui, N., Graham, D., Yuva-Paylor, L. A., and Paylor, R. (2009). Marble burying reflects a repetitive and perseverative behavior more than novelty-induced anxiety. Psychopharmacology 204, 361-373.

Tremaroli, V., and Backhed, F. (2012). Functional interactions between the gut microbiota and host metabolism. Nature 489, 242-249.

Turnbaugh, P. J., Ley, R. E., Mahowald, M. A., Magrini, V., Mardis, E. R., and Gordon, J. I. (2006). An obesity-associated gut microbiome with increased capacity for energy harvest. Nature 444, 1027-1031.

Ungless, M. A., Whistler, J. L., Malenka, R. C., and Bonci, A. (2001). Single cocaine exposure in vivo induces long-term potentiation in dopamine neurons. Nature 411, 583-587.

Uvnas-Moberg, K., Handlin, L., and Petersson, M. (2014). Self-soothing behaviors with particular reference to oxytocin release induced by non-noxious sensory stimulation. Frontiers in psychology 5, 1529.

Varian, B. J. et al., Microbial lysate upregulates host oxytocin. Brain Behavior Immun., 2017. 61(0): p. 36-49.

Wang, B., Mao, Y. K., Diorio, C., Pasyk, M., Wu, R. Y., Bienenstock, J., and Kunze, W. A. (2010). Luminal administration ex vivo of a live *Lactobacillus* species moderates mouse jejunal motility within minutes. FASEB journal: official publication of the Federation of American Societies for Experimental Biology 24, 4078-4088.

Wang, X., Wang, B. R., Zhang, X. J., Xu, Z., Ding, Y. Q., and Ju, G. (2002). Evidences for vagus nerve in maintenance of immune balance and transmission of immune information from gut to brain in STM-infected rats. World journal of gastroenterology 8, 540-545.

Wu, S., Jia, M., Ruan, Y., Liu, J., Guo, Y., Shuang, M., Gong, X., Zhang, Y., Yang, X., and Zhang, D. (2005). Positive association of the oxytocin receptor gene (OXTR) with autism in the Chinese Han population. Biological psychiatry 58, 74-77.

Yatsunenko, T., Rey, F. E., Manary, M. J., Trehan, I., Dominguez-Bello, M. G., Contreras, M., Magris, M., Hidalgo, G., Baldassano, R. N., Anokhin, A. P., et al. (2012). Human gut microbiome viewed across age and geography. Nature 486, 222-227.

Yoo, H. J., et al., Family-based genetic association study of CNTNAP2 polymorphisms and sociality endophenotypes in Korean patients with autism spectrum disorders. Psychiatr Genet, 2017. 27(1): p. 38-39.

Zablotsky, B., Black, L. I., Maenner, M. J., Schieve, L. A., and Blumberg, S. J. (2015). Estimated Prevalence of Autism and Other Developmental Disabilities Following Questionnaire Changes in the 2014 National Health Interview Survey. National Health Statistics Reports 1-20.

Zare, S., F. Mashayekhi, and E. Bidabadi, The association of CNTNAP2 rs7794745 gene polymorphism and autism in Iranian population. J Clin Neurosci, 2017. 39: p. 189-192.

Zhu, P. J., Huang, W., Kalikulov, D., Yoo, J. W., Placzek, A. N., Stoica, L., Zhou, H., Bell, J. C., Friedlander, M. J., Krnjevic, K., et al. (2011). Suppression of PKR promotes network excitability and enhanced cognition by interferon-gamma-mediated disinhibition. Cell 147, 1384-1396.

Zik, J. B. and D. L. Roberts, The many faces of oxytocin: implications for psychiatry. Psychiatry Res, 2015. 226(1): p. 31-7.

What is claimed is:

1. A method of treating a social behavioral deficiency in a subject, comprising administering to the subject a therapeutically effective amount of a formulation comprising:

*Lactobacillus reuteri* MM4-1A (ATCC-PTA-6475), wherein the social behavioral deficiency is autism or autism spectrum disorder.

2. The method of claim 1, wherein the autism or autism spectrum disorder comprises impaired sociability, preference for social novelty, difficulty in social use of verbal and nonverbal communication, or a combination thereof.

3. The method claim 1, wherein the subject has or is at risk of having one or more of William Syndrome, Prader-Willi syndrome, Fragile X syndrome, bipolar disorder, Schizophrenia, Depression, Postpartum depression, anxiety, Parkinson's disease, Social cognitive impairment, and/or Alzheimer's Disease.

4. The method of claim 1, wherein the formulation further comprises an additional bacteria species or nutrient(s).

5. The method of claim 1, wherein the formulation is delivered via a pill or suppository comprising the formulation.

6. The method of claim 1, wherein the formulation is included in a food, beverage, yogurt, dry powder, or the dry powder mixed in water or a beverage.

7. The method of claim 1, further comprising administration of one or more prebiotics or other nutrients.

8. The method of claim 1, wherein, during gestation of the subject, the mother was obese, overweight, or followed a high-fat diet.

* * * * *